US011946056B2

(12) United States Patent
Decrulle et al.

(10) Patent No.: US 11,946,056 B2
(45) Date of Patent: *Apr. 2, 2024

(54) OPTIMIZED VECTOR FOR DELIVERY IN MICROBIAL POPULATIONS

(71) Applicants: Eligo Bioscience, Paris (FR); Institut Pasteur, Paris (FR)

(72) Inventors: Antoine Decrulle, Paris (FR); Jesus Fernandez Rodriguez, Paris (FR); Xavier Duportet, Paris (FR); David Bikard, Paris (FR)

(73) Assignees: ELIGO BIOSCIENCE, Paris (FR); INSTITUT PASTEUR, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/356,079

(22) Filed: Jun. 23, 2021

(65) Prior Publication Data

US 2021/0380993 A1    Dec. 9, 2021

Related U.S. Application Data

(63) Continuation of application No. 17/017,111, filed on Sep. 10, 2020, now Pat. No. 11,078,490, which is a
(Continued)

(30) Foreign Application Priority Data

Feb. 3, 2017   (EP) .................................... 17305126

(51) Int. Cl.
*C12N 15/73* (2006.01)
*A61K 35/76* (2015.01)
(Continued)

(52) U.S. Cl.
CPC .............. *C12N 15/73* (2013.01); *A61K 35/76* (2013.01); *A61P 31/04* (2018.01); *C12N 7/00* (2013.01);
(Continued)

(58) Field of Classification Search
None
See application file for complete search history.

(56) References Cited

U.S. PATENT DOCUMENTS 5,702,931 A * 12/1997 Andrews ................ C12N 15/85
435/91.42
10,808,254 B2   10/2020 Decrulle et al.
(Continued)

FOREIGN PATENT DOCUMENTS

WO   2014124226 A1   8/2014
WO   2015034872 A2   3/2015

OTHER PUBLICATIONS

Kasarjian JK, Kodama Y, Iida M, Matsuda K, Ryu J. Four new type I restriction enzymes identified in *Escherichia coli* clinical isolates. Nucleic Acids Res. Jul. 21, 2005;33(13):e114. doi: 10.1093/nar/gni114. PMID: 16040596; PMCID: PMC1178010. (Year: 2005).*
(Continued)

*Primary Examiner* — Michelle S Horning
(74) *Attorney, Agent, or Firm* — Carter, DeLuca & Farrell LLP; Carmella L. Stephens

(57) ABSTRACT

The present invention relates to a vector, preferably included in a delivery vehicle, comprising no more than 100, preferably no more than 10, restriction sites recognized by the restriction enzymes encoded by each bacterium of a group of bacteria of interest. The invention also relates to the use of said vector, preferably included in a delivery vehicle, as a drug, especially in the treatment of a disease in a patient in need thereof.

15 Claims, 4 Drawing Sheets

Specification includes a Sequence Listing.

Related U.S. Application Data continuation of application No. 16/527,762, filed on Jul. 31, 2019, now Pat. No. 10,808,254, which is a continuation of application No. PCT/EP2018/052662, filed on Feb. 2, 2018.

(51) Int. Cl.
*A61P 31/04* (2006.01)
*C12N 7/00* (2006.01)
*C12N 15/74* (2006.01)

(52) U.S. Cl.
CPC .... *C12N 15/74* (2013.01); *C12N 2795/10332* (2013.01); *C12N 2800/10* (2013.01); *C12N 2800/101* (2013.01)

(56) References Cited

U.S. PATENT DOCUMENTS

| | | | |
|---|---|---|---|
| 11,078,490 B2 | 8/2021 | Decrulle et al. | |
| 2018/0273910 A1* | 9/2018 | Rohwer | C12N 7/00 |
| 2020/0248192 A1* | 8/2020 | Decrulle | A61P 31/04 |

OTHER PUBLICATIONS

Murray NE, Murray K. Manipulation of restriction targets in phage lambda to form receptor chromosomes for DNA fragments. Nature. Oct. 11, 1974;251(5475):476-81. doi: 10.1038/251476a0. PMID: 4608939. (Year: 1974).*
Chatterjee and Rothenberg. Interaction of bacteriophage I with its *E. coli* receptor, LamB. Viruses. Nov. 15, 2012;4(11):3162-78. (Year: 2012).
Mead et al., "Chimeric Single-Stranded DNA Phage-Plasmid Cloning Vectors," Vectors, A Survey of Molecular Cloning Vectors and their Uses, (1988); Chapter 4 pp. 85-102.
Westwater et al., "Development of a P1 phagemid system for the delivery of DNA into Gram-negative bacteria," Microbiology (2002), vol. 148; pp. 943-950.
Wang et al., "Programming cells by multiplex genome engineering and accelerated evolution," Nature, Aug. 13, 2009, vol. 460, No. 7257; pp. 894-898.
Torsten Seeman, "Prokka: rapid prokaryotic genome annotation," Bioinformatics, vol. 30, No. 14 (2014); pp. 2068-2069.
Roberts et al., "Rebase—a database for DNA restriction and modication: enzymes, genes and genomes," Nucleic Acids Research, vol. 43, (2015); pp. D298-D299.
Roberts et al., "A nomenclature for restriction enzymes, DNA methyltransferases, homing endonucleases and their genes ," Nucleic Acids Research, vol. 31, No. 7, (2003); pp. 1805-1812.
Pires et al., "Genetically Engineered Phages: A Review of Advances over the Last Decade," American Society for Microbiology, Microbiology and Molecular Biology Reviews, vol. 80, No. 3, (2016); pp. 523-543.
Mutalik et al., "Precise and reliable gene expression via standard transcription and translation initiation elements," Nature Methods, vol. 10, (2013); pp. 354-360.
Kenan C. Murphy, "Use of Bacteriophage .lamda. Recombination Functions to Promote Gene Replacement in *Escherichia coli*," Journal of Bacteriology, vol. 180, No. 8, Apr. 1998; pp. 2063-2071.

Kittleson et al., "Scalable Plasmid Transfer using Engineered P1-based Phagemids," ACS Synthetic Biology, (2012); pp. 583-589.
Joska et al., A universal cloning method based on yeast homologous recombination that is simple, efficient, and versatile, J. Microbiol Methods, May 2014, vol. 100; pp. 46-51.
Jiang et al., "Multigene Editing in the *Escherichia coli* Genome via the CRISPR-Cas9 System," Applied and Environmental Microbiology, vol. 81, No. 7; Apr. 2015; pp. 2506-2514.
Hughes et al., "Synthetic DNA Synthesis and Assembly: Putting the Synthetic in Synthetic Biology," Cold SPring Harbor Laboratory Press, vol. 9, No. 1, Jan. 2017; pp. 1-17.
Henkel et al., Toxins from Bacteria, National Institutes of Health, vol. 100, EXS (2010); pp. 1-29.
Sanger et al., Nudeotide sequence of bacteriophage .PHI. X174 DNA, Nature, vol. 265, Feb. 24, 1977, pp. 687-695.
Citorik et al., "Sequence-specific antimicrobials using efficiently delivered RNA-guided nucleases," National Institutes of Health, vol. 32, No. 11, Nov. 2014; pp. 1141-1145.
Chen et al., Characterization of 582 natural and synthetic terminators and quantification of their design constraints, Nature Methods, vol. 10, No. 7, Jul. 2013; pp. 659-666.
Cambray et al., "Measurement and modeling of intrinsic transcription terminators," Nucleic Acids Research, vol. 41, No. 9, (2013); pp. 5139-5148.
Brettin et al., RASTtk: A modular and extensible implementation of the RAST algorithm for building custom annotation pipelines and annotating batches of genomes, Scientific Reports, 5: 8365, Feb. 10, 2015; pp. 1-6.
Bikard et al., "Exploiting CRISPR-Cas nucleases to produce sequence-specific antimicrobials," Nature Biotechnology, vol. 32, No. 11, Nov. 2014; pp. 1146-1151.
Bankevich et al., "SPAdes: A New Genome Assembly Algorithm and Its Applications to Single-Cell Sequencing," Journal of Computational Biology, vol. 19, No. 5, (2012); pp. 455-477.
Tock and Dryden. The biology of restriction and anti-restriction. Curr Opin Microbiol Aug. 2005;8(4):466-72. doi: 10.1016/j.mib. 2005.06.003. (Year: 2005).
Enterobacteria phase phiX174 sensu lato, complete genome, NCBI, 2015; 7 total pages.
Steven S. Skiena, "Designing better phages," Bioinformatics, vol. 17, Suppl. 1, (2001); pp. S253-S261.
Paul M. Sharp, "Molecular Evolution of Bacteriophages: Evidence of Selection against the Recognition Sites of Host Restriction Enzymes1," Mol. Biol. Evol., vol. 3, No. 1; (1986) pp. 75-83.
Rebase Enz No. 90357, Type I methyltransferase, (2014); 1 page.
Rebase Enz No. 90384, Type II restriction enzyme and methyltransferase, (2016); 1 page.
Sulakvelidze et al., "Bacteriophage Therapy," Antimicrobial AGents in Chemotherapy, Mar. 1, 2001, vol. 45, No. 3; pp. 649-659.
European Communicatoin dated Sep. 10, 2020, corresponding to counterpart European Application No. 17305126.9; 7 pages.
English translation of Japanese Office Action dated Mar. 7, 2022, corresponding to counterpart Japanese Application No. 2019-563676; 8 pages.
Japanese Office Action for related application No. 2019-563676, dated Sep. 5, 2022, 5 pages.
Campbell, A., "Comparative molecular biology of lambdoid phages," Annual review of microbiology, Jan. 1994, pp. 193-223, 48.

* cited by examiner

FIGURE 1

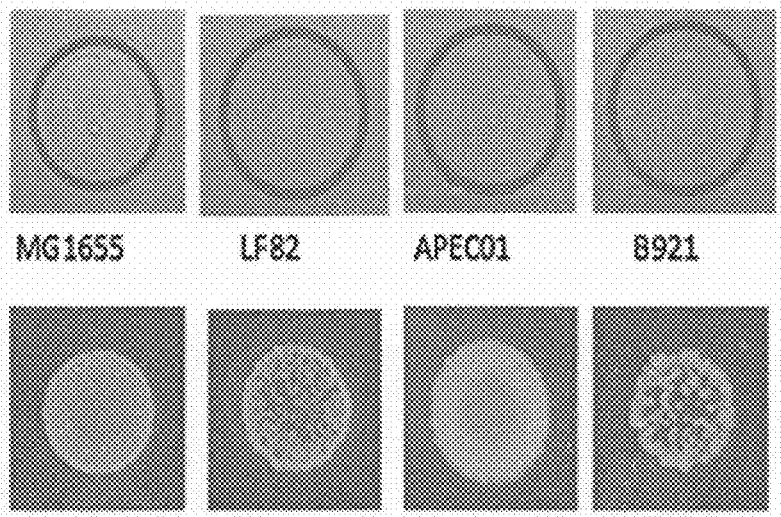
Figure 1 (following)

SEQUENCE LISTING

```
<160> NUMBER OF SEQ ID NOS: 233

<210> SEQ ID NO 1
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(10)
<223> OTHER INFORMATION: n is a, c, g, or t

<400> SEQUENCE: 1
cacnnnnnnn ctgg                                                      14

<210> SEQ ID NO 2
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t

<400> SEQUENCE: 2
aacnnnnnng tgc                                                       13

<210> SEQ ID NO 3
<211> LENGTH: 11
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(7)
<223> OTHER INFORMATION: n is a, c, g, or t
<220> FEATURE:
<221> NAME/KEY: misc_feature
<222> LOCATION: (11)..(11)

<400> SEQUENCE: 3
cacnnnngta y                                                         11

<210> SEQ ID NO 4
<211> LENGTH: 11
<212> TYPE: DNA
<213> ORGANISM: Artificial Sequence
<220> FEATURE:
<223> OTHER INFORMATION: Restricition site
<220> FEATURE:
<221> NAME/KEY: misc_feature
<222> LOCATION: (4)..(7)
<223> OTHER INFORMATION: n is a, c, g, or t

<400> SEQUENCE: 4
aacnnnnctt t                                                         11

<210> SEQ ID NO 5
<211> LENGTH: 14
<212> TYPE: DNA
<213> ORGANISM: Artificial Sequence
<220> FEATURE:
<223> OTHER INFORMATION: Restricition site
<220> FEATURE:
<221> NAME/KEY: misc_feature
<222> LOCATION: (4)..(10)
```

```
<223> OTHER INFORMATION: n is a, c, g, or t

<400> SEQUENCE: 5
ccannnnnnn cttc                                                            14

<210> SEQ ID NO 6
<211> LENGTH: 15
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (11)..(11)
<223> OTHER INFORMATION: r is A or G
<220> FEATURE:
<221> NAME/KEY: misc_feature
<222> LOCATION: (13)..(13)
<223> OTHER INFORMATION: r is A or G

<400> SEQUENCE: 6
tacnnnnnnn rtrtc                                                           15

<210> SEQ ID NO 7
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(10)
<223> OTHER INFORMATION: n is a, c, g, or t

<400> SEQUENCE: 7
gagnnnnnnn gtca                                                            14

<210> SEQ ID NO 8
<211> LENGTH: 15
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(11)
<223> OTHER INFORMATION: n is a, c, g, or t

<400> SEQUENCE: 8
tgannnnnnn ntgct                                                           15

<210> SEQ ID NO 9
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(10)
<223> OTHER INFORMATION: n is a, c, g, or t

<400> SEQUENCE: 9
agcannnnnn tga                                                             13
```

```
<210> SEQ ID NO 10
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t

<400> SEQUENCE: 10
tgannnnnnc ttc                                                        13

<210> SEQ ID NO 11
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t
<220> FEATURE:
<221> NAME/KEY: misc_feature
<222> LOCATION: (11)..(11)
<223> OTHER INFORMATION: y is c or t

<400> SEQUENCE: 11
gagnnnnngt ty                                                         12

<210> SEQ ID NO 12
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(10)
<223> OTHER INFORMATION: n is a, c, g, or t

<400> SEQUENCE: 12
gatgnnnnnn tac                                                        13

<210> SEQ ID NO 13
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t
<220> FEATURE:
<221> NAME/KEY: misc_feature
<222> LOCATION: (10)..(10)
<223> OTHER INFORMATION: r is a or g

<400> SEQUENCE: 13
gaannnnnnr tcg                                                        13

<210> SEQ ID NO 14
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
```

```
<221> NAME/KEY: misc_feature
<222> LOCATION: (1)..(1)
<223> OTHER INFORMATION: r is a or g
<220> FEATURE:
<221> NAME/KEY: misc_feature
<222> LOCATION: (5)..(10)
<223> OTHER INFORMATION: n is a, c, g, or t

<400> SEQUENCE: 14
rtcannnnnn ctc                                                          13

<210> SEQ ID NO 15
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(8)
<223> OTHER INFORMATION: n is a, c, g, or t
<220> FEATURE:
<221> NAME/KEY: misc_feature
<222> LOCATION: (9)..(9)
<223> OTHER INFORMATION: r is a or g
<220> FEATURE:
<221> NAME/KEY: misc_feature
<222> LOCATION: (11)..(11)
<223> OTHER INFORMATION: d is a, g or t

<400> SEQUENCE: 15
gnagnnnnrt dca                                                          13

<210> SEQ ID NO 16
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (11)..(11)
<223> OTHER INFORMATION: r is a or g

<400> SEQUENCE: 16
gaannnnnnn rtcg                                                         14

<210> SEQ ID NO 17
<211> LENGTH: 15
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(11)
<223> OTHER INFORMATION: n is a, c, g, or t

<400> SEQUENCE: 17 ggannnnnnnn natgc                                                       15

<210> SEQ ID NO 18
<211> LENGTH: 11
```

```
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t

<400> SEQUENCE: 18
gagnnnnntc c                                                     11

<210> SEQ ID NO 19
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(10)
<223> OTHER INFORMATION: n is a, c, g, or t

<400> SEQUENCE: 19
cacnnnnnnn gttg                                                  14

<210> SEQ ID NO 20
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (1)..(1)
<223> OTHER INFORMATION: y is c or t
<220> FEATURE:
<221> NAME/KEY: misc_feature
<222> LOCATION: (5)..(10)
<223> OTHER INFORMATION: n is a, c, g, or t
<220> FEATURE:
<221> NAME/KEY: misc_feature
<222> LOCATION: (14)..(14)
<223> OTHER INFORMATION: y is c or t

<400> SEQUENCE: 20
ytcannnnnn gtty                                                  14

<210> SEQ ID NO 21
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(9)
<223> OTHER INFORMATION: n is a, c, g, or t

<400> SEQUENCE: 21
gatgnnnnnc tg                                                    12

<210> SEQ ID NO 22
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(4)
```

<223> OTHER INFORMATION: y is c or t
<220> FEATURE:
<221> NAME/KEY: misc_feature
<222> LOCATION: (5)..(9)
<223> OTHER INFORMATION: n is a, c, g, or t
<220> FEATURE:
<221> NAME/KEY: misc_feature
<222> LOCATION: (13)..(13)
<223> OTHER INFORMATION: y is c or t

<400> SEQUENCE: 22
ccaynnnnng tty                                                          13

<210> SEQ ID NO 23
<211> LENGTH: 16
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (1)..(1)
<223> OTHER INFORMATION: r is a or g
<220> FEATURE:
<221> NAME/KEY: misc_feature
<222> LOCATION: (5)..(12)
<223> OTHER INFORMATION: n is a, c, g, or t

<400> SEQUENCE: 23
rtcannnnnn nngtgg                                                       16

<210> SEQ ID NO 24
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(10)
<223> OTHER INFORMATION: n is a, c, g, or t

<400> SEQUENCE: 24
gaannnnnnn taaa                                                         14

<210> SEQ ID NO 25
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (11)..(11)
<223> OTHER INFORMATION: r is a or g

<400> SEQUENCE: 25
tcannnnnnn rttc                                                         14

<210> SEQ ID NO 26
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature

```
<222> LOCATION: (4)..(9)
<223> OTHER INFORMATION: n is a, c, g, or t

<400> SEQUENCE: 26
gacnnnnnng tc                                                         12

<210> SEQ ID NO 27
<211> LENGTH: 16
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(12)
<223> OTHER INFORMATION: n is a, c, g, or t

<400> SEQUENCE: 27
ttcannnnnn nnctgg                                                     16

<210> SEQ ID NO 28
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (14)..(14)
<223> OTHER INFORMATION: y is c or t

<400> SEQUENCE: 28
ttannnnnnn gtcy                                                       14

<210> SEQ ID NO 29
<211> LENGTH: 14
<212> TYPE: DNA
<213> ORGANISM: Artificial Sequence
<220> FEATURE:
<223> OTHER INFORMATION: Resztriction site
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (11)..(11)
<223> OTHER INFORMATION: r is a or g

<400> SEQUENCE: 29
ccannnnnnn rtgc                                                       14

<210> SEQ ID NO 30
<211> LENGTH: 15
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(11)
<223> OTHER INFORMATION: n is a, c, g, or t

<400> SEQUENCE: 30
ccannnnnnn ntgaa                                                      15
```

```
<210> SEQ ID NO 31
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(10)
<223> OTHER INFORMATION: n is a, c, g, or t

<400> SEQUENCE: 31
gagnnnnnnn atgc                                                          14

<210> SEQ ID NO 32
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t

<400> SEQUENCE: 32
cagnnnnnnc gt                                                            12

<210> SEQ ID NO 33
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(9)
<223> OTHER INFORMATION: n is a, c, g, or t

<400> SEQUENCE: 33
gatgnnnnng gc                                                            12

<210> SEQ ID NO 34
<211> LENGTH: 7
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(5)
<223> OTHER INFORMATION: b is c, g or t

<400> SEQUENCE: 34 gaaabcc                                                                   7

<210> SEQ ID NO 35
<211> LENGTH: 5
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (3)..(3)
<223> OTHER INFORMATION: w is a or t

<400> SEQUENCE: 35 ccwgg                                                                     5
```

```
<210> SEQ ID NO 36
<211> LENGTH: 6
<212> TYPE: DNA
<213> ORGANISM: Artificial Sequence
<220> FEATURE:
<223> OTHER INFORMATION: Synthetic: Restriction site

<400> SEQUENCE: 36 ggtctc                                                                       6

<210> SEQ ID NO 37
<211> LENGTH: 6
<212> TYPE: DNA
<213> ORGANISM: Artificial Sequence
<220> FEATURE:
<223> OTHER INFORMATION: Synthetic: Restriction site

<400> SEQUENCE: 37 ctgcag                                                                       6

<210> SEQ ID NO 38
<211> LENGTH: 6
<212> TYPE: DNA
<213> ORGANISM: Artificial Sequence
<220> FEATURE:
<223> OTHER INFORMATION: Synthetic: Restriction site

<400> SEQUENCE: 38 gccggc                                                                       6

<210> SEQ ID NO 39
<211> LENGTH: 7
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (1)..(1)
<223> OTHER INFORMATION: r is a or g
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (7)..(7)
<223> OTHER INFORMATION: y is c or t

<400> SEQUENCE: 39 rggnccy                                                                      7

<210> SEQ ID NO 40
<211> LENGTH: 6
<212> TYPE: DNA
<213> ORGANISM: Artificial Sequence
<220> FEATURE:
<223> OTHER INFORMATION: Synthetic: Restriction site

<400> SEQUENCE: 40 gtcgac                                                                       6

<210> SEQ ID NO 41
<211> LENGTH: 6
<212> TYPE: DNA
<213> ORGANISM: Artificial Sequence
<220> FEATURE:
```

```
<223> OTHER INFORMATION: Synthetic: Restriction site

<400> SEQUENCE: 41 gcgcgc                                                                  6

<210> SEQ ID NO 42
<211> LENGTH: 6
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (1)..(1)
<223> OTHER INFORMATION: r is a or g
<220> FEATURE:
<221> NAME/KEY: misc_feature
<222> LOCATION: (6)..(6)
<223> OTHER INFORMATION: y is c or T

<400> SEQUENCE: 42 rccggy                                                                  6

<210> SEQ ID NO 43
<211> LENGTH: 5
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (3)..(3)
<223> OTHER INFORMATION: n is a, c, g, or t

<400> SEQUENCE: 43 ccngg                                                                   5

<210> SEQ ID NO 44
<211> LENGTH: 6
<212> TYPE: DNA
<213> ORGANISM: Artificial Sequence
<220> FEATURE:
<223> OTHER INFORMATION: Synthetic: Restriction site

<400> SEQUENCE: 44 aagctt                                                                  6

<210> SEQ ID NO 45
<211> LENGTH: 7
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (3)..(3)
<223> OTHER INFORMATION: n is a, c, g, or t

<400> SEQUENCE: 45 cancatc                                                                 7

<210> SEQ ID NO 46
<211> LENGTH: 6
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
```

```
<222> LOCATION: (2)..(2)
<223> OTHER INFORMATION: r is a or g
<220> FEATURE:
<221> NAME/KEY: misc_feature
<222> LOCATION: (5)..(5)
<223> OTHER INFORMATION: y is c or t

<400> SEQUENCE: 46 grcgyc                                                                    6

<210> SEQ ID NO 47
<211> LENGTH: 6
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (2)..(2)
<223> OTHER INFORMATION: y is c or t
<220> FEATURE:
<221> NAME/KEY: misc_feature
<222> LOCATION: (5)..(5)
<223> OTHER INFORMATION: r is a or g

<400> SEQUENCE: 47 cycgrg                                                                    6

<210> SEQ ID NO 48
<211> LENGTH: 5
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (3)..(3)
<223> OTHER INFORMATION: n is a, c, g, or t

<400> SEQUENCE: 48 gcngc                                                                     5

<210> SEQ ID NO 49
<211> LENGTH: 6
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (1)..(1)
<223> OTHER INFORMATION: y is c or t
<220> FEATURE:
<221> NAME/KEY: misc_feature
<222> LOCATION: (6)..(6)
<223> OTHER INFORMATION: r is a or g

<400> SEQUENCE: 49 yggccr                                                                    6

<210> SEQ ID NO 50
<211> LENGTH: 6
<212> TYPE: DNA
<213> ORGANISM: Artificial Sequence
<220> FEATURE:
<223> OTHER INFORMATION: Synthetic: Restriction Site

<400> SEQUENCE: 50 ccgcgg                                                                    6
```

```
<210> SEQ ID NO 51
<211> LENGTH: 6
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (2)..(2)
<223> OTHER INFORMATION: r is a or g
<220> FEATURE:
<221> NAME/KEY: misc_feature
<222> LOCATION: (5)..(5)
<223> OTHER INFORMATION: y is c or t

<400> SEQUENCE: 51 grgcyc                                                                   6

<210> SEQ ID NO 52
<211> LENGTH: 6
<212> TYPE: DNA
<213> ORGANISM: Artificial Sequence
<220> FEATURE:
<223> OTHER INFORMATION: Synthetic: Restriction site

<400> SEQUENCE: 52 ctgaag                                                                   6

<210> SEQ ID NO 53
<211> LENGTH: 5
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (3)..(3)
<223> OTHER INFORMATION: w is a or t

<400> SEQUENCE: 53 ggwcc                                                                    5

<210> SEQ ID NO 54
<211> LENGTH: 6
<212> TYPE: DNA
<213> ORGANISM: Artificial Sequence
<220> FEATURE:
<223> OTHER INFORMATION: Synthetic: Restriction site

<400> SEQUENCE: 54 tggcca                                                                   6

<210> SEQ ID NO 55
<211> LENGTH: 6
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (3)..(4)
<223> OTHER INFORMATION: w is a or t

<400> SEQUENCE: 55 ccwwgg                                                                   6

<210> SEQ ID NO 56
<211> LENGTH: 5
```

```
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (3)..(3)
<223> OTHER INFORMATION: n is a, c, g, or t

<400> SEQUENCE: 56 ggncc                                                                  5

<210> SEQ ID NO 57
<211> LENGTH: 6
<212> TYPE: DNA
<213> ORGANISM: Artificial Sequence
<220> FEATURE:
<223> OTHER INFORMATION: Synthetic: Restriction site

<400> SEQUENCE: 57 gagctc                                                                 6

<210> SEQ ID NO 58
<211> LENGTH: 6
<212> TYPE: DNA
<213> ORGANISM: Artificial Sequence
<220> FEATURE:
<223> OTHER INFORMATION: Synthetic: Restriction site

<400> SEQUENCE: 58 ggtacc                                                                 6

<210> SEQ ID NO 59
<211> LENGTH: 6
<212> TYPE: DNA
<213> ORGANISM: Artificial Sequence
<220> FEATURE:
<223> OTHER INFORMATION: Synthetic: Restriction site

<400> SEQUENCE: 59 ggcgcc                                                                 6

<210> SEQ ID NO 60
<211> LENGTH: 6
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(4)
<223> OTHER INFORMATION: y is c or t

<400> SEQUENCE: 60 accyac                                                                 6

<210> SEQ ID NO 61
<211> LENGTH: 6
<212> TYPE: DNA
<213> ORGANISM: Artificial Sequence
<220> FEATURE:
<223> OTHER INFORMATION: Synthetic: Restriction site

<400> SEQUENCE: 61 gaattc                                                                 6

<210> SEQ ID NO 62
```

```
<211> LENGTH: 6
<212> TYPE: DNA
<213> ORGANISM: Artificial Sequence
<220> FEATURE:
<223> OTHER INFORMATION: Synthetic: Restriction site

<400> SEQUENCE: 62 gatatc                                                                    6

<210> SEQ ID NO 63
<211> LENGTH: 7
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(4)
<223> OTHER INFORMATION: n is a, c, g, or t

<400> SEQUENCE: 63 cctnagg                                                                   7

<210> SEQ ID NO 64
<211> LENGTH: 7
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(4)
<223> OTHER INFORMATION: n is a, c, g, or t

<400> SEQUENCE: 64 ggtnacc                                                                   7

<210> SEQ ID NO 65
<211> LENGTH: 6
<212> TYPE: DNA
<213> ORGANISM: Artificial Sequence
<220> FEATURE:
<223> OTHER INFORMATION: Synthetic: Restriction site

<400> SEQUENCE: 65 atgcat                                                                    6

<210> SEQ ID NO 66
<211> LENGTH: 6
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (3)..(3)
<223> OTHER INFORMATION: y is c or t
<220> FEATURE:
<221> NAME/KEY: misc_feature
<222> LOCATION: (4)..(4)
<223> OTHER INFORMATION: r is a or g

<400> SEQUENCE: 66 ggyrcc                                                                    6

<210> SEQ ID NO 67
<211> LENGTH: 6
<212> TYPE: DNA
<213> ORGANISM: Artificial Sequence
```

```
<220> FEATURE:
<223> OTHER INFORMATION: Synthetic: Restriction site

<400> SEQUENCE: 67 aggcct                                                                6

<210> SEQ ID NO 68
<211> LENGTH: 6
<212> TYPE: DNA
<213> ORGANISM: Artificial Sequence
<220> FEATURE:
<223> OTHER INFORMATION: Synthetic: Restriction site

<400> SEQUENCE: 68 ctcaat                                                                6

<210> SEQ ID NO 69
<211> LENGTH: 5
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (3)..(3)
<223> OTHER INFORMATION: w is a or t

<400> SEQUENCE: 69 gcwgc                                                                 5

<210> SEQ ID NO 70
<211> LENGTH: 6
<212> TYPE: DNA
<213> ORGANISM: Artificial Sequence
<220> FEATURE:
<223> OTHER INFORMATION: Synthetic: Restriction site

<400> SEQUENCE: 70 tcgcga                                                                6

<210> SEQ ID NO 71
<211> LENGTH: 11
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t

<400> SEQUENCE: 71
cctnnnnnag g                                                         11

<210> SEQ ID NO 72
<211> LENGTH: 6
<212> TYPE: DNA
<213> ORGANISM: Artificial Sequence
<220> FEATURE:
<223> OTHER INFORMATION: Synthetic: Restriction site

<400> SEQUENCE: 72 accacc                                                                6

<210> SEQ ID NO 73
<211> LENGTH: 5
<212> TYPE: DNA
```

```
<213> ORGANISM: Artificial Sequence
<220> FEATURE:
<223> OTHER INFORMATION: Synthetic: Restriction site

<400> SEQUENCE: 73 cacag                                                                5

<210> SEQ ID NO 74
<211> LENGTH: 5
<212> TYPE: DNA
<213> ORGANISM: Artificial Sequence
<220> FEATURE:
<223> OTHER INFORMATION: Synthetic: Restriction site

<400> SEQUENCE: 74 gaacc                                                                5

<210> SEQ ID NO 75
<211> LENGTH: 5
<212> TYPE: DNA
<213> ORGANISM: Artificial Sequence
<220> FEATURE:
<223> OTHER INFORMATION: Synthetic: Restriction site

<400> SEQUENCE: 75 gagac                                                                5

<210> SEQ ID NO 76
<211> LENGTH: 6
<212> TYPE: DNA
<213> ORGANISM: Artificial Sequence
<220> FEATURE:
<223> OTHER INFORMATION: Synthetic: Restriction site

<400> SEQUENCE: 76 cagcag                                                               6

<210> SEQ ID NO 77
<211> LENGTH: 5
<212> TYPE: DNA
<213> ORGANISM: Artificial Sequence
<220> FEATURE:
<223> OTHER INFORMATION: Synthetic: Restriction enzyme

<400> SEQUENCE: 77 agacc                                                                5

<210> SEQ ID NO 78
<211> LENGTH: 5
<212> TYPE: DNA
<213> ORGANISM: Artificial Sequence
<220> FEATURE:
<223> OTHER INFORMATION: Synthetic: Restriction site

<400> SEQUENCE: 78 ccgag                                                                5

<210> SEQ ID NO 79
<211> LENGTH: 6
<212> TYPE: DNA
<213> ORGANISM: Artificial Sequence
<220> FEATURE:
<223> OTHER INFORMATION: Synthetic: Restriction site

<400> SEQUENCE: 79 gatcag                                                               6
```

```
<210> SEQ ID NO 80
<211> LENGTH: 15
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(11)
<223> OTHER INFORMATION: n is a, c, g, or t

<400> SEQUENCE: 80
ggannnnnnn natgc                                                    15

<210> SEQ ID NO 81
<211> LENGTH: 11
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t

<400> SEQUENCE: 81
gagnnnnnta c                                                        11

<210> SEQ ID NO 82
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(11)
<223> OTHER INFORMATION: n is a, c, g, or t

<400> SEQUENCE: 82
gcannnnnnn ntgc                                                     14

<210> SEQ ID NO 83
<211> LENGTH: 11
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t

<400> SEQUENCE: 83
gacnnnnntg a                                                        11

<210> SEQ ID NO 84
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(10)
<223> OTHER INFORMATION: n is a, c, g, or t

<400> SEQUENCE: 84
```

-continued ggtannnnnn tcg                                                            13

<210> SEQ ID NO 85
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t
<220> FEATURE:
<221> NAME/KEY: misc_feature
<222> LOCATION: (10)..(10)
<223> OTHER INFORMATION: r is g or a
<220> FEATURE:
<221> NAME/KEY: misc_feature
<222> LOCATION: (10)..(10)
<223> OTHER INFORMATION: r is g or a
<220> FEATURE:
<221> NAME/KEY: misc_feature
<222> LOCATION: (13)..(13)
<223> OTHER INFORMATION: y is t or c

<400> SEQUENCE: 85
gagnnnnnnr tayg                                                           14

<210> SEQ ID NO 86
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t
<220> FEATURE:
<221> NAME/KEY: misc_feature
<222> LOCATION: (9)..(9)
<223> OTHER INFORMATION: r is g or a

<400> SEQUENCE: 86
cccnnnnnrt ag                                                             12

<210> SEQ ID NO 87
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (3)..(3)
<223> OTHER INFORMATION: y is t or c
<220> FEATURE:
<221> NAME/KEY: misc_feature
<222> LOCATION: (5)..(10)
<223> OTHER INFORMATION: n is a, c, g, or t

<400> SEQUENCE: 87
ggyannnnnn tcg                                                            13

<210> SEQ ID NO 88
<211> LENGTH: 15
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(11)
<223> OTHER INFORMATION: n is a, c, g, or t

<400> SEQUENCE: 88
ccannnnnnn ntgag             15

<210> SEQ ID NO 89
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t

<400> SEQUENCE: 89
gcannnnnnt taa             13

<210> SEQ ID NO 90
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (2)..(2)
<223> OTHER INFORMATION: r is g or a
<220> FEATURE:
<221> NAME/KEY: misc_feature
<222> LOCATION: (5)..(11)
<223> OTHER INFORMATION: n is a, c, g, or t

<400> SEQUENCE: 90
craannnnnn ntgc             14

<210> SEQ ID NO 91
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(10)
<223> OTHER INFORMATION: n is a, c, g, or t
<220> FEATURE:
<221> NAME/KEY: misc_feature
<222> LOCATION: (11)..(11)
<223> OTHER INFORMATION: r is g or a

<400> SEQUENCE: 91
craannnnnn ntgc             14

<210> SEQ ID NO 92
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t

<400> SEQUENCE: 92
aagnnnnnnc atc             13

```
<210> SEQ ID NO 93
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t

<400> SEQUENCE: 93
cagnnnnnnc gt                                                             12

<210> SEQ ID NO 94
<211> LENGTH: 15
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(4)
<223> OTHER INFORMATION: y is t or c
<220> FEATURE:
<221> NAME/KEY: misc_feature
<222> LOCATION: (5)..(11)
<223> OTHER INFORMATION: n is a, c, g, or t

<400> SEQUENCE: 94 gaaynnnnnnn nctgg                                                         15

<210> SEQ ID NO 95
<211> LENGTH: 15
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(11)
<223> OTHER INFORMATION: n is a, c, g, or t

<400> SEQUENCE: 95 cgannnnnnnn ntgcc                                                         15

<210> SEQ ID NO 96
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t

<400> SEQUENCE: 96
acgnnnnngt tg                                                             12

<210> SEQ ID NO 97
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (2)..(3)
<223> OTHER INFORMATION: y is t or c
```

<220> FEATURE:
<221> NAME/KEY: misc_feature
<222> LOCATION: (5)..(10)
<223> OTHER INFORMATION: n is a, c, g, or t

<400> SEQUENCE: 97
cyyannnnnn cttc                                                              14

<210> SEQ ID NO 98
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (11)..(11)
<223> OTHER INFORMATION: r is g or a

<400> SEQUENCE: 98
cacnnnnnnn rtgt                                                              14

<210> SEQ ID NO 99
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(10)
<223> OTHER INFORMATION: n is a, c, g, or t

<400> SEQUENCE: 99
cccannnnnn tcg                                                               13

<210> SEQ ID NO 100
<211> LENGTH: 11
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t

<400> SEQUENCE: 100
aggnnnnnga t                                                                 11

<210> SEQ ID NO 101
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (3)..(3)
<223> OTHER INFORMATION: y is t or c
<220> FEATURE:
<221> NAME/KEY: misc_feature
<222> LOCATION: (5)..(10)
<223> OTHER INFORMATION: n is a, c, g, or t

<400> SEQUENCE: 101

```
ccaynnnnnn tgt                                                          13
```

```
<210> SEQ ID NO 102
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(4)
<223> OTHER INFORMATION: y is t or c
<220> FEATURE:
<221> NAME/KEY: misc_feature
<222> LOCATION: (5)..(10)
<223> OTHER INFORMATION: n is a, c, g, or t

<400> SEQUENCE: 102
ccaynnnnnn gta                                                          13
```

```
<210> SEQ ID NO 103
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t

<400> SEQUENCE: 103
aagnnnnnnc atc                                                          13
```

```
<210> SEQ ID NO 104
<211> LENGTH: 11
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(6)
<223> OTHER INFORMATION: n is a, c, g, or t
<220> FEATURE:
<221> NAME/KEY: misc_feature
<222> LOCATION: (7)..(7)
<223> OTHER INFORMATION: r is g or a

<400> SEQUENCE: 104 gatnnnrta c                                                             11
```

```
<210> SEQ ID NO 105
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t
<220> FEATURE:
<221> NAME/KEY: misc_feature
<222> LOCATION: (9)..(9)
<223> OTHER INFORMATION: r is g or a

<400> SEQUENCE: 105 gcannnnrt ta                                                            12
```

-continued

```
<210> SEQ ID NO 106
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (1)..(13)
<223> OTHER INFORMATION: r is g or a

<400> SEQUENCE: 106
raacnnnnnn rtta                                                     14

<210> SEQ ID NO 107
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t

<400> SEQUENCE: 107
agtnnnnnnr ttg                                                      13

<210> SEQ ID NO 108
<211> LENGTH: 10
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t

<400> SEQUENCE: 108 gagnnnnngt                                                          10

<210> SEQ ID NO 109
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(4)
<223> OTHER INFORMATION: y is t or c
<220> FEATURE:
<221> NAME/KEY: misc_feature
<222> LOCATION: (5)..(9)
<223> OTHER INFORMATION: n is a, c, g, or t

<400> SEQUENCE: 109
gaaynnnnng tc                                                       12

<210> SEQ ID NO 110
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (3)..(8)
<223> OTHER INFORMATION: n is a, c, g, or t
```

```
<400> SEQUENCE: 110
gannnnnntg cg                                                          12

<210> SEQ ID NO 111
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(10)
<223> OTHER INFORMATION: n is a, c, g, or t

<400> SEQUENCE: 111
ttagnnnnnn ttc                                                         13

<210> SEQ ID NO 112
<211> LENGTH: 11
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(8)
<223> OTHER INFORMATION: n is a, c, g, or t

<400> SEQUENCE: 112
gatgnnnntg t                                                           11

<210> SEQ ID NO 113
<211> LENGTH: 11
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t
<220> FEATURE:
<221> NAME/KEY: misc_feature
<222> LOCATION: (9)..(9)
<223> OTHER INFORMATION: r is g or a

<400> SEQUENCE: 113
gagnnnnnrt g                                                           11

<210> SEQ ID NO 114
<211> LENGTH: 11
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t

<400> SEQUENCE: 114
cacnnnnnta c                                                           11

<210> SEQ ID NO 115
<211> LENGTH: 15
<212> TYPE: DNA
<213> ORGANISM: Artificial Sequence
<220> FEATURE:
<223> OTHER INFORMATION: Synthetic: Restriction site
```

```
<220> FEATURE:
<221> NAME/KEY: misc_feature
<222> LOCATION: (2)..(2)
<223> OTHER INFORMATION: r is g or a
<220> FEATURE:
<221> NAME/KEY: misc_feature
<222> LOCATION: (5)..(12)
<223> OTHER INFORMATION: n is a, c, g, or t

<400> SEQUENCE: 115
craannnnnn nnctt                                                     15

<210> SEQ ID NO 116
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(10)
<223> OTHER INFORMATION: n is a, c, g, or t

<400> SEQUENCE: 116
tgannnnnnn tatc                                                      14

<210> SEQ ID NO 117
<211> LENGTH: 16
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (2)..(2)
<223> OTHER INFORMATION: r is g or a
<220> FEATURE:
<221> NAME/KEY: misc_feature
<222> LOCATION: (5)..(13)
<223> OTHER INFORMATION: n is a, c, g, or t

<400> SEQUENCE: 117
craannnnnn nnnttc                                                    16

<210> SEQ ID NO 118
<211> LENGTH: 15
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (2)..(2)
<223> OTHER INFORMATION: r is g or a
<220> FEATURE:
<221> NAME/KEY: misc_feature
<222> LOCATION: (5)..(12)
<223> OTHER INFORMATION: n is a, c, g, or t

<400> SEQUENCE: 118
craannnnnn nnctg                                                     15

<210> SEQ ID NO 119
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(10)
```

<223> OTHER INFORMATION: n is a, c, g, or t

<400> SEQUENCE: 119
cacnnnnnnn ctg                                                              13

<210> SEQ ID NO 120
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(11)
<223> OTHER INFORMATION: n is a, c, g, or t

<400> SEQUENCE: 120
cacnnnnnnn nttc                                                             14

<210> SEQ ID NO 121
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(10)
<223> OTHER INFORMATION: n is a, c, g, or t

<400> SEQUENCE: 121
cacnnnnnnn ctt                                                              13

<210> SEQ ID NO 122
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(11)
<223> OTHER INFORMATION: n is a, c, g, or t

<400> SEQUENCE: 122
tttannnnnn ngtt                                                             14

<210> SEQ ID NO 123
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t
<220> FEATURE:
<221> NAME/KEY: misc_feature
<222> LOCATION: (12)..(12)
<223> OTHER INFORMATION: y is t or c

<400> SEQUENCE: 123
ctannnnngt ty                                                               12

<210> SEQ ID NO 124
<211> LENGTH: 12
<212> TYPE: DNA
<213> ORGANISM: Artificial Sequence

```
<220> FEATURE:
<223> OTHER INFORMATION: Synthetic: Restriction site
<220> FEATURE:
<221> NAME/KEY: misc_feature
<222> LOCATION: (3)..(3)
<223> OTHER INFORMATION: y is t or c
<220> FEATURE:
<221> NAME/KEY: misc_feature
<222> LOCATION: (4)..(9)
<223> OTHER INFORMATION: n is a, c, g, or t

<400> SEQUENCE: 124
gaynnnnnng tt                                                              12

<210> SEQ ID NO 125
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(9)
<223> OTHER INFORMATION: n is a, c, g, or t

<400> SEQUENCE: 125
cccannnnnc tg                                                              12

<210> SEQ ID NO 126
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(10)
<223> OTHER INFORMATION: n is a, c, g, or t

<400> SEQUENCE: 126
tccannnnnn cgt                                                             13

<210> SEQ ID NO 127
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t
<220> FEATURE:
<221> NAME/KEY: misc_feature
<222> LOCATION: (9)..(9)
<223> OTHER INFORMATION: r is g or a

<400> SEQUENCE: 127
acgnnnnnrt gt                                                              12

<210> SEQ ID NO 128
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t
```

```
<400> SEQUENCE: 128
atgnnnnnnc ctc                                                          13

<210> SEQ ID NO 129
<211> LENGTH: 15
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(4)
<223> OTHER INFORMATION: b is g or c or t
<220> FEATURE:
<221> NAME/KEY: misc_feature
<222> LOCATION: (5)..(11)
<223> OTHER INFORMATION: n is a, c, g, or t

<400> SEQUENCE: 129
tcabnnnnnn ntcca                                                        15

<210> SEQ ID NO 130
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t

<400> SEQUENCE: 130
gacnnnnnng atc                                                          13

<210> SEQ ID NO 131
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t

<400> SEQUENCE: 131
aggnnnnntt ca                                                           12

<210> SEQ ID NO 132
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(9)
<223> OTHER INFORMATION: n is a, c, g, or t

<400> SEQUENCE: 132
gaagnnnnnt ac                                                           12

<210> SEQ ID NO 133
<211> LENGTH: 13
<212> TYPE: DNA
<213> ORGANISM: Artificial Sequence
<220> FEATURE:
<223> OTHER INFORMATION: Synthetic: Restriction site
```

```
<220> FEATURE:
<221> NAME/KEY: misc_feature
<222> LOCATION: (4)..(4)
<223> OTHER INFORMATION: y is t or c
<220> FEATURE:
<221> NAME/KEY: misc_feature
<222> LOCATION: (5)..(9)
<223> OTHER INFORMATION: n is a, c, g, or t

<400> SEQUENCE: 133
ccaynnnnnt taa                                                              13

<210> SEQ ID NO 134
<211> LENGTH: 15
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(11)
<223> OTHER INFORMATION: n is a, c, g, or t
<220> FEATURE:
<221> NAME/KEY: misc_feature
<222> LOCATION: (12)..(12)
<223> OTHER INFORMATION: r is g or a

<400> SEQUENCE: 134
cncannnnnn nrtgt                                                            15

<210> SEQ ID NO 135
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t
<220> FEATURE:
<221> NAME/KEY: misc_feature
<222> LOCATION: (10)..(10)
<223> OTHER INFORMATION: r is g or a
<220> FEATURE:
<221> NAME/KEY: misc_feature
<222> LOCATION: (13)..(13)
<223> OTHER INFORMATION: n is a, c, g, or t

<400> SEQUENCE: 135
ccannnnnnr ttnc                                                             14

<210> SEQ ID NO 136
<211> LENGTH: 15
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(4)
<223> OTHER INFORMATION: y is t or c
<220> FEATURE:
<221> NAME/KEY: misc_feature
<222> LOCATION: (5)..(11)
<223> OTHER INFORMATION: n is a, c, g, or t

<400> SEQUENCE: 136
```
acaynnnnnn nttgg                                                    15

<210> SEQ ID NO 137
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(11)
<223> OTHER INFORMATION: n is a, c, g, or t

<400> SEQUENCE: 137
gatannnnnn ntgc                                                     14

<210> SEQ ID NO 138
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t

<400> SEQUENCE: 138
gccnnnnngt tg                                                       12

<210> SEQ ID NO 139
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(10)
<223> OTHER INFORMATION: n is a, c, g, or t

<400> SEQUENCE: 139
catcnnnnnn tcc                                                      13

<210> SEQ ID NO 140
<211> LENGTH: 17
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (1)..(1)
<223> OTHER INFORMATION: r is g or a
<220> FEATURE:
<221> NAME/KEY: misc_feature
<222> LOCATION: (5)..(13)
<223> OTHER INFORMATION: n is a, c, g, or t
<220> FEATURE:
<221> NAME/KEY: misc_feature
<222> LOCATION: (15)..(15)
<223> OTHER INFORMATION: r is g or a

<400> SEQUENCE: 140
rtcannnnnn nnntrgg                                                  17

<210> SEQ ID NO 141
<211> LENGTH: 11
<212> TYPE: DNA
<213> ORGANISM: Artificial Sequence

```
<220> FEATURE:
<223> OTHER INFORMATION: Synthetic: Restriction site
<220> FEATURE:
<221> NAME/KEY: misc_feature
<222> LOCATION: (5)..(8)
<223> OTHER INFORMATION: n is a, c, g, or t

<400> SEQUENCE: 141
attcnnnnct g                                                        11

<210> SEQ ID NO 142
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(11)
<223> OTHER INFORMATION: n is a, c, g, or t

<400> SEQUENCE: 142
taagnnnnnn ntgg                                                     14

<210> SEQ ID NO 143
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t
<220> FEATURE:
<221> NAME/KEY: misc_feature
<222> LOCATION: (10)..(10)
<223> OTHER INFORMATION: r is g or a

<400> SEQUENCE: 143
gagnnnnnnr tgc                                                      13

<210> SEQ ID NO 144
<211> LENGTH: 11
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t

<400> SEQUENCE: 144
cccnnnnnct c                                                        11

<210> SEQ ID NO 145
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t

<400> SEQUENCE: 145
agcnnnnnnt aca                                                      13
```

```
<210> SEQ ID NO 146
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(10)
<223> OTHER INFORMATION: n is a, c, g, or t

<400> SEQUENCE: 146
ccannnnnnn ctta                                                    14

<210> SEQ ID NO 147
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(4)
<223> OTHER INFORMATION: y is t or c
<220> FEATURE:
<221> NAME/KEY: misc_feature
<222> LOCATION: (5)..(10)
<223> OTHER INFORMATION: n is a, c, g, or t

<400> SEQUENCE: 147
gcaynnnnnn ctc                                                     13

<210> SEQ ID NO 148
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (3)..(9)
<223> OTHER INFORMATION: n is a, c, g, or t

<400> SEQUENCE: 148
cannnnnnnt aaag                                                    14

<210> SEQ ID NO 149
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t
<220> FEATURE:
<221> NAME/KEY: misc_feature
<222> LOCATION: (9)..(9)
<223> OTHER INFORMATION: r is g or a

<400> SEQUENCE: 149
tagnnnnnrt gaa                                                     13

<210> SEQ ID NO 150
<211> LENGTH: 13
<212> TYPE: DNA
<213> ORGANISM: Artificial Sequence
<220> FEATURE:
<223> OTHER INFORMATION: Synthetic: Restriction site
```

```
<220> FEATURE:
<221> NAME/KEY: misc_feature
<222> LOCATION: (4)..(4)
<223> OTHER INFORMATION: y is t or c
<220> FEATURE:
<221> NAME/KEY: misc_feature
<222> LOCATION: (5)..(9)
<223> OTHER INFORMATION: n is a, c, g, or t

<400> SEQUENCE: 150
attynnnnnc ttc                                                              13

<210> SEQ ID NO 151
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (2)..(2)
<223> OTHER INFORMATION: y is t or c
<220> FEATURE:
<221> NAME/KEY: misc_feature
<222> LOCATION: (4)..(9)
<223> OTHER INFORMATION: n is a, c, g, or t

<400> SEQUENCE: 151
aygnnnnnnc tg                                                               12

<210> SEQ ID NO 152
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t
<220> FEATURE:
<221> NAME/KEY: misc_feature
<222> LOCATION: (10)..(10)
<223> OTHER INFORMATION: r is g or a

<400> SEQUENCE: 152
gaannnnnnr tgc                                                              13

<210> SEQ ID NO 153
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(4)
<223> OTHER INFORMATION: b is g, c or t
<220> FEATURE:
<221> NAME/KEY: misc_feature
<222> LOCATION: (5)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 153
tacbnnnnnn gtng                                                             14

<210> SEQ ID NO 154
```

```
<211> LENGTH: 11
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(8)
<223> OTHER INFORMATION: n is a, c, g, or t

<400> SEQUENCE: 154
gatgnnnntg t                                                          11

<210> SEQ ID NO 155
<211> LENGTH: 11
<212> TYPE: DNA
<213> ORGANISM: Artificial Sequence sequenec
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t

<400> SEQUENCE: 155
gacnnnnngg t                                                          11

<210> SEQ ID NO 156
<211> LENGTH: 15
<212> TYPE: DNA
<213> ORGANISM: Artificial Sequence sequenec
<220> FEATURE:
<223> OTHER INFORMATION: Synthetic: Restriction site
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (11)..(11)
<223> OTHER INFORMATION: r is g or a

<400> SEQUENCE: 156
ggannnnnnn rtggc                                                      15

<210> SEQ ID NO 157
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(11)
<223> OTHER INFORMATION: n is a, c, g, or t

<400> SEQUENCE: 157
ctannnnnnn ntgt                                                       14

<210> SEQ ID NO 158
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(11)
<223> OTHER INFORMATION: n is a, c, g, or t

<400> SEQUENCE: 158
```

```
acannnnnnn ntag                                                          14

<210> SEQ ID NO 159
<211> LENGTH: 11
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t

<400> SEQUENCE: 159
ccannnnnnt c                                                             11

<210> SEQ ID NO 160
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (3)..(9)
<223> OTHER INFORMATION: n is a, c, g, or t
<220> FEATURE:
<221> NAME/KEY: misc_feature
<222> LOCATION: (13)..(13)
<223> OTHER INFORMATION: y is t or c

<400> SEQUENCE: 160
gannnnnnnt ayg                                                           13

<210> SEQ ID NO 161
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (1)..(1)
<223> OTHER INFORMATION: r is g or a
<220> FEATURE:
<221> NAME/KEY: misc_feature
<222> LOCATION: (4)..(4)
<223> OTHER INFORMATION: y is t or c
<220> FEATURE:
<221> NAME/KEY: misc_feature
<222> LOCATION: (5)..(9)
<223> OTHER INFORMATION: n is a, c, g, or t
<220> FEATURE:
<221> NAME/KEY: misc_feature
<222> LOCATION: (13)..(13)
<223> OTHER INFORMATION: y is t or c

<400> SEQUENCE: 161
rtaynnnnnr tay                                                           13

<210> SEQ ID NO 162
<211> LENGTH: 11
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t
```

<400> SEQUENCE: 162
aagnnnnnct t                                                    11

<210> SEQ ID NO 163
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t

<400> SEQUENCE: 163
aagnnnnnnt aaag                                                 14

<210> SEQ ID NO 164
<211> LENGTH: 12
<212> TYPE: DNA
<213> ORGANISM: Artificial Sequence
<220> FEATURE:
<223> OTHER INFORMATION: restrictioon site
<220> FEATURE:
<221> NAME/KEY: misc_feature
<222> LOCATION: (4)..(9)
<223> OTHER INFORMATION: n is a, c, g, or t

<400> SEQUENCE: 164
ccannnnnnt tt                                                   12

<210> SEQ ID NO 165
<211> LENGTH: 11
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t

<400> SEQUENCE: 165
cagnnnnnga t                                                    11

<210> SEQ ID NO 166
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t

<400> SEQUENCE: 166
aagnnnnnct cc                                                   12

<210> SEQ ID NO 167
<211> LENGTH: 11
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(7)
<223> OTHER INFORMATION: n is a, c, g, or t

```
<220> FEATURE:
<221> NAME/KEY: misc_feature
<222> LOCATION: (8)..(8)
<223> OTHER INFORMATION: r is g or a

<400> SEQUENCE: 167
gagnnnnrta a                                                              11

<210> SEQ ID NO 168
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t

<400> SEQUENCE: 168
ggannnnnnc ttt                                                            13

<210> SEQ ID NO 169
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (14)..(14)
<223> OTHER INFORMATION: y is t or c

<400> SEQUENCE: 169
ttannnnnnn gtcy                                                           14

<210> SEQ ID NO 170
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(11)
<223> OTHER INFORMATION: n is a, c, g, or t

<400> SEQUENCE: 170
gaagnnnnnn ntcc                                                           14

<210> SEQ ID NO 171
<211> LENGTH: 10
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(7)
<223> OTHER INFORMATION: n is a, c, g, or t

<400> SEQUENCE: 171 cagnnnnctg                                                                10

<210> SEQ ID NO 172
```

```
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t
<220> FEATURE:
<221> NAME/KEY: misc_feature
<222> LOCATION: (10)..(10)
<223> OTHER INFORMATION: r is g or a

<400> SEQUENCE: 172
acannnnnnr tgg                                                    13

<210> SEQ ID NO 173
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(4)
<223> OTHER INFORMATION: y is t or c
<220> FEATURE:
<221> NAME/KEY: misc_feature
<222> LOCATION: (5)..(10)
<223> OTHER INFORMATION: n is a, c, g, or t

<400> SEQUENCE: 173
gcaynnnnnn catc                                                   14

<210> SEQ ID NO 174
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(4)
<223> OTHER INFORMATION: y is t or c
<220> FEATURE:
<221> NAME/KEY: misc_feature
<222> LOCATION: (5)..(9)
<223> OTHER INFORMATION: n is a, c, g, or t
<220> FEATURE:
<221> NAME/KEY: misc_feature
<222> LOCATION: (13)..(13)
<223> OTHER INFORMATION: y is t or c

<400> SEQUENCE: 174
ataynnnnnc tay                                                    13

<210> SEQ ID NO 175
<211> LENGTH: 13
<212> TYPE: DNA
<213> ORGANISM: Artificial Sequence
<220> FEATURE:
<223> OTHER INFORMATION: restrction site
<220> FEATURE:
<221> NAME/KEY: misc_feature
<222> LOCATION: (4)..(4)
<223> OTHER INFORMATION: y is t or c
<220> FEATURE:
<221> NAME/KEY: misc_feature
<222> LOCATION: (5)..(9)
<223> OTHER INFORMATION: n is a, c, g, or t
<220> FEATURE:
<221> NAME/KEY: misc_feature
```

```
<222> LOCATION: (10)..(10)
<223> OTHER INFORMATION: r is g or a

<400> SEQUENCE: 175
gaaynnnnnr tac                                                          13

<210> SEQ ID NO 176
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t

<400> SEQUENCE: 176
ccannnnnnt tga                                                          13

<210> SEQ ID NO 177
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t
<220> FEATURE:
<221> NAME/KEY: misc_feature
<222> LOCATION: (10)..(10)
<223> OTHER INFORMATION: r is a or g

<400> SEQUENCE: 177
ggannnnnnr taa                                                          13

<210> SEQ ID NO 178
<211> LENGTH: 11
<212> TYPE: DNA
<213> ORGANISM: Artificial Sequence
<220> FEATURE:
<223> OTHER INFORMATION: restrction site
<220> FEATURE:
<221> NAME/KEY: misc_feature
<222> LOCATION: (3)..(3)
<223> OTHER INFORMATION: y is t or c
<220> FEATURE:
<221> NAME/KEY: misc_feature
<222> LOCATION: (4)..(8)
<223> OTHER INFORMATION: n is a, c, g, or t
<220> FEATURE:
<221> NAME/KEY: misc_feature
<222> LOCATION: (9)..(9)
<223> OTHER INFORMATION: r is g or a

<400> SEQUENCE: 178
gaynnnnnrt c                                                            11

<210> SEQ ID NO 179
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(10)
<223> OTHER INFORMATION: n is a, c, g, or t
```

```
<400> SEQUENCE: 179
cggannnnnn ttc                                                      13

<210> SEQ ID NO 180
<211> LENGTH: 11
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t

<400> SEQUENCE: 180
acannnnngt g                                                        11

<210> SEQ ID NO 181
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(10)
<223> OTHER INFORMATION: n is a, c, g, or t

<400> SEQUENCE: 181
gtannnnnnn ctc                                                      13

<210> SEQ ID NO 182
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t

<400> SEQUENCE: 182
gcannnnnnt taa                                                      13

<210> SEQ ID NO 183
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t

<400> SEQUENCE: 183
acgnnnnngt tg                                                       12

<210> SEQ ID NO 184
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t
```

-continued

```
<400> SEQUENCE: 184
aagnnnnngt tc                                                          12

<210> SEQ ID NO 185
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (3)..(3)
<223> OTHER INFORMATION: y is t or c
<220> FEATURE:
<221> NAME/KEY: misc_feature
<222> LOCATION: (4)..(9)
<223> OTHER INFORMATION: n is a, c, g, or t

<400> SEQUENCE: 185
caynnnnnnt ca                                                          12

<210> SEQ ID NO 186
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(4)
<223> OTHER INFORMATION: h is a or c or t
<220> FEATURE:
<221> NAME/KEY: misc_feature
<222> LOCATION: (5)..(10)
<223> OTHER INFORMATION: n is a, c, g, or t

<400> SEQUENCE: 186
caahnnnnnn cttc                                                        14

<210> SEQ ID NO 187
<211> LENGTH: 15
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(11)
<223> OTHER INFORMATION: n is a, c, g, or t

<400> SEQUENCE: 187
gcannnnnnn ngtgg                                                       15

<210> SEQ ID NO 188
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(10)
<223> OTHER INFORMATION: n is a, c, g, or t

<400> SEQUENCE: 188
tcagnnnnnn tgc                                                         13

<210> SEQ ID NO 189
```

```
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(9)
<223> OTHER INFORMATION: n is a, c, g, or t

<400> SEQUENCE: 189
caacnnnnnc tt                                                              12

<210> SEQ ID NO 190
<211> LENGTH: 16
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(4)
<223> OTHER INFORMATION: y is t or c
<220> FEATURE:
<221> NAME/KEY: misc_feature
<222> LOCATION: (5)..(11)
<223> OTHER INFORMATION: n is a, c, g, or t
<220> FEATURE:
<221> NAME/KEY: misc_feature
<222> LOCATION: (12)..(12)
<223> OTHER INFORMATION: r is g ro a
<220> FEATURE:
<221> NAME/KEY: misc_feature
<222> LOCATION: (14)..(14)
<223> OTHER INFORMATION: d is a or g or t

<400> SEQUENCE: 190 gaaynnnnnnn nrtdcc                                                         16

<210> SEQ ID NO 191
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(9)
<223> OTHER INFORMATION: n is a, c, g, or t

<400> SEQUENCE: 191
cgaannnnnt ga                                                              12

<210> SEQ ID NO 192
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t

<400> SEQUENCE: 192
gacnnnnnnc tgg                                                             13

<210> SEQ ID NO 193
<211> LENGTH: 14
<212> TYPE: DNA
<213> ORGANISM: Artificial Sequence
```

```
<220> FEATURE:
<223> OTHER INFORMATION: Synthetic: Restriction site
<220> FEATURE:
<221> NAME/KEY: misc_feature
<222> LOCATION: (4)..(10)
<223> OTHER INFORMATION: n is a, c, g, or t

<400> SEQUENCE: 193
tgannnnnnn tggg                                                          14

<210> SEQ ID NO 194
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t

<400> SEQUENCE: 194
gagnnnnnnt ta                                                            12

<210> SEQ ID NO 195
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t

<400> SEQUENCE: 195
gagnnnnnnt gg                                                            12

<210> SEQ ID NO 196
<211> LENGTH: 16
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (6)..(12)
<223> OTHER INFORMATION: n is a, c, g, or t

<400> SEQUENCE: 196
gnngannnnn nntggg                                                        16

<210> SEQ ID NO 197
<211> LENGTH: 11
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(4)
<223> OTHER INFORMATION: k is g or t
<220> FEATURE:
<221> NAME/KEY: misc_feature
<222> LOCATION: (5)..(8)
<223> OTHER INFORMATION: n is a, c, g, or t
```

```
<400> SEQUENCE: 197
taaknnnngt c                                                              11

<210> SEQ ID NO 198
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(9)
<223> OTHER INFORMATION: n is a, c, g, or t

<400> SEQUENCE: 198
cgcannnnnc tg                                                             12

<210> SEQ ID NO 199
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(10)
<223> OTHER INFORMATION: n is a, c, g, or t

<400> SEQUENCE: 199
ccannnnnnn tggg                                                           14

<210> SEQ ID NO 200
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (3)..(3)
<223> OTHER INFORMATION: y is t or c
<220> FEATURE:
<221> NAME/KEY: misc_feature
<222> LOCATION: (4)..(9)
<223> OTHER INFORMATION: n is a, c, g, or t

<400> SEQUENCE: 200
agynnnnnnc ttc                                                            13

<210> SEQ ID NO 201
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(10)
<223> OTHER INFORMATION: n is a, c, g, or t

<400> SEQUENCE: 201
ccannnnnnn ctc                                                            13

<210> SEQ ID NO 202
<211> LENGTH: 14
<212> TYPE: DNA
<213> ORGANISM: Artificial Sequence
<220> FEATURE:
<223> OTHER INFORMATION: Synthetic: Restriction site
```

```
<220> FEATURE:
<221> NAME/KEY: misc_feature
<222> LOCATION: (4)..(9)
<223> OTHER INFORMATION: n is a, c, g, or t
<220> FEATURE:
<221> NAME/KEY: misc_feature
<222> LOCATION: (10)..(10)
<223> OTHER INFORMATION: Y IS T OR C
<220> FEATURE:
<221> NAME/KEY: misc_feature
<222> LOCATION: (13)..(13)
<223> OTHER INFORMATION: n is a, c, g, or t

<400> SEQUENCE: 202
ccannnnnnr ttnc                                                          14

<210> SEQ ID NO 203
<211> LENGTH: 16
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (1)..(1)
<223> OTHER INFORMATION: r is g or a
<220> FEATURE:
<221> NAME/KEY: misc_feature
<222> LOCATION: (5)..(12)
<223> OTHER INFORMATION: n is a, c, g, or t
<220> FEATURE:
<221> NAME/KEY: misc_feature
<222> LOCATION: (13)..(13)
<223> OTHER INFORMATION: r is g or a

<400> SEQUENCE: 203
rgaannnnnn nnrtga                                                        16

<210> SEQ ID NO 204
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t
<220> FEATURE:
<221> NAME/KEY: misc_feature
<222> LOCATION: (10)..(10)
<223> OTHER INFORMATION: r is g or a

<400> SEQUENCE: 204
agtnnnnnnr tgc                                                           13

<210> SEQ ID NO 205
<211> LENGTH: 15
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (2)..(2)
<223> OTHER INFORMATION: h is a or c or t
<220> FEATURE:
<221> NAME/KEY: misc_feature
<222> LOCATION: (5)..(11)
<223> OTHER INFORMATION: n is a, c, g, or t
<220> FEATURE:
<221> NAME/KEY: misc_feature
<222> LOCATION: (14)..(14)
```

<223> OTHER INFORMATION: d is a or g or t

<400> SEQUENCE: 205
ghtannnnnn ntadc                                                    15

<210> SEQ ID NO 206
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (2)..(2)
<223> OTHER INFORMATION: y is t or c
<220> FEATURE:
<221> NAME/KEY: misc_feature
<222> LOCATION: (4)..(4)
<223> OTHER INFORMATION: y is t or c
<220> FEATURE:
<221> NAME/KEY: misc_feature
<222> LOCATION: (5)..(9)
<223> OTHER INFORMATION: n is a, c, g, or t

<400> SEQUENCE: 206
gyaynnnnnc ttg                                                      13

<210> SEQ ID NO 207
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t
<220> FEATURE:
<221> NAME/KEY: misc_feature
<222> LOCATION: (14)..(14)
<223> OTHER INFORMATION: y is t or c

<400> SEQUENCE: 207
tagnnnnnnc ttgy                                                     14

<210> SEQ ID NO 208
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(4)
<223> OTHER INFORMATION: y is t or c
<220> FEATURE:
<221> NAME/KEY: misc_feature
<222> LOCATION: (5)..(9)
<223> OTHER INFORMATION: n is a, c, g, or t

<400> SEQUENCE: 208
ccaynnnnng ct                                                       12

<210> SEQ ID NO 209
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature

```
<222> LOCATION: (4)..(9)
<223> OTHER INFORMATION: n is a, c, g, or t
<220> FEATURE:
<221> NAME/KEY: misc_feature
<222> LOCATION: (10)..(10)
<223> OTHER INFORMATION: r is g or a

<400> SEQUENCE: 209
ctannnnnnr tgaa                                                         14

<210> SEQ ID NO 210
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(5)
<223> OTHER INFORMATION: y is t or c
<220> FEATURE:
<221> NAME/KEY: misc_feature
<222> LOCATION: (6)..(10)
<223> OTHER INFORMATION: n is a, c, g, or t

<400> SEQUENCE: 210
tttaynnnnn gtg                                                          13

<210> SEQ ID NO 211
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(4)
<223> OTHER INFORMATION: y is t or c
<220> FEATURE:
<221> NAME/KEY: misc_feature
<222> LOCATION: (5)..(10)
<223> OTHER INFORMATION: n is a, c, g, or t
<220> FEATURE:
<221> NAME/KEY: misc_feature
<222> LOCATION: (11)..(11)
<223> OTHER INFORMATION: r is g or a

<400> SEQUENCE: 211
taaynnnnnn rttg                                                         14

<210> SEQ ID NO 212
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t

<400> SEQUENCE: 212
ccannnnnnt tga                                                          13

<210> SEQ ID NO 213
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
```

```
<221> NAME/KEY: misc_feature
<222> LOCATION: (4)..(9)
<223> OTHER INFORMATION: n is a, c, g, or t
<220> FEATURE:
<221> NAME/KEY: misc_feature
<222> LOCATION: (10)..(10)
<223> OTHER INFORMATION: r is g or a

<400> SEQUENCE: 213
ggannnnnnr taa                                                             13

<210> SEQ ID NO 214
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (3)..(9)
<223> OTHER INFORMATION: n is a, c, g, or t
<220> FEATURE:
<221> NAME/KEY: misc_feature
<222> LOCATION: (12)..(12)
<223> OTHER INFORMATION: y is t or c

<400> SEQUENCE: 214
gannnnnnnt ay                                                              12

<210> SEQ ID NO 215
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t
<220> FEATURE:
<221> NAME/KEY: misc_feature
<222> LOCATION: (10)..(10)
<223> OTHER INFORMATION: r is g or a
<220> FEATURE:
<221> NAME/KEY: misc_feature
<222> LOCATION: (13)..(13)
<223> OTHER INFORMATION: y is t or c

<400> SEQUENCE: 215
gagnnnnnnr tayg                                                            14

<210> SEQ ID NO 216
<211> LENGTH: 15
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(11)
<223> OTHER INFORMATION: n is a, c, g, or t

<400> SEQUENCE: 216 gaannnnnnnn ntcgc                                                          15

<210> SEQ ID NO 217
<211> LENGTH: 13
<212> TYPE: DNA
<213> ORGANISM: Artificial Sequence
<220> FEATURE:
<223> OTHER INFORMATION: Synthetic: Restriction site
```

```
<220> FEATURE:
<221> NAME/KEY: misc_feature
<222> LOCATION: (5)..(10)
<223> OTHER INFORMATION: n is a, c, g, or t

<400> SEQUENCE: 217
ggtannnnnn tcg                                                              13

<210> SEQ ID NO 218
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t

<400> SEQUENCE: 218
gccnnnnnnt cg                                                               12

<210> SEQ ID NO 219
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(9)
<223> OTHER INFORMATION: n is a, c, g, or t

<400> SEQUENCE: 219
ggcannnnnc tc                                                               12

<210> SEQ ID NO 220
<211> LENGTH: 15
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(11)
<223> OTHER INFORMATION: n is a, c, g, or t
<220> FEATURE:
<221> NAME/KEY: misc_feature
<222> LOCATION: (15)..(15)
<223> OTHER INFORMATION: y is t or c

<400> SEQUENCE: 220
gtannnnnnn ngtcy                                                            15

<210> SEQ ID NO 221
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(10)
<223> OTHER INFORMATION: n is a, c, g, or t

<400> SEQUENCE: 221
ggcannnnnn tta                                                              13

<210> SEQ ID NO 222
```

```
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (2)..(2)
<223> OTHER INFORMATION: r is g or a
<220> FEATURE:
<221> NAME/KEY: misc_feature
<222> LOCATION: (5)..(10)
<223> OTHER INFORMATION: n is a, c, g, or t

<400> SEQUENCE: 222
craannnnnn ctc                                                           13

<210> SEQ ID NO 223
<211> LENGTH: 15
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(4)
<223> OTHER INFORMATION: y is t or c
<220> FEATURE:
<221> NAME/KEY: misc_feature
<222> LOCATION: (5)..(11)
<223> OTHER INFORMATION: n is a, c, g, or t

<400> SEQUENCE: 223 taaynnnnnnn ntctt                                                        15

<210> SEQ ID NO 224
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(10)
<223> OTHER INFORMATION: n is a, c, g, or t

<400> SEQUENCE: 224
gagnnnnnnn tcc                                                           13

<210> SEQ ID NO 225
<211> LENGTH: 14
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(11)
<223> OTHER INFORMATION: n is a, c, g, or t

<400> SEQUENCE: 225 ccannnnnnnn ntgg                                                         14

<210> SEQ ID NO 226
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
```

```
<222> LOCATION: (2)..(2)
<223> OTHER INFORMATION: y is t or c
<220> FEATURE:
<221> NAME/KEY: misc_feature
<222> LOCATION: (4)..(4)
<223> OTHER INFORMATION: y is t or c
<220> FEATURE:
<221> NAME/KEY: misc_feature
<222> LOCATION: (5)..(8)
<223> OTHER INFORMATION: n is a, c, g, or t
<220> FEATURE:
<221> NAME/KEY: misc_feature
<222> LOCATION: (10)..(10)
<223> OTHER INFORMATION: r is a or g

<400> SEQUENCE: 226
gyaynnnngr tg                                                              12

<210> SEQ ID NO 227
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(10)
<223> OTHER INFORMATION: n is a, c, g, or t

<400> SEQUENCE: 227
ttcannnnnn tcc                                                             13

<210> SEQ ID NO 228
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (1)..(1)
<223> OTHER INFORMATION: y is t or c
<220> FEATURE:
<221> NAME/KEY: misc_feature
<222> LOCATION: (4)..(8)
<223> OTHER INFORMATION: n is a, c, g, or t

<400> SEQUENCE: 228
yacnnnnngt ag                                                              12

<210> SEQ ID NO 229
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(9)
<223> OTHER INFORMATION: n is a, c, g, or t
<220> FEATURE:
<221> NAME/KEY: misc_feature
<222> LOCATION: (10)..(10)
<223> OTHER INFORMATION: r is g or a

<400> SEQUENCE: 229
tagnnnnnnr tgg                                                             13

<210> SEQ ID NO 230
<211> LENGTH: 14
<212> TYPE: DNA
```

-continued

```
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (3)..(3)
<223> OTHER INFORMATION: y is t or c
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (13)..(13)
<223> OTHER INFORMATION: y is t or c

<400> SEQUENCE: 230
gaynnnnnnn tcyc                                                      14

<210> SEQ ID NO 231
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (5)..(8)
<223> OTHER INFORMATION: n is a, c, g, or t
<220> FEATURE:
<221> NAME/KEY: misc_feature
<222> LOCATION: (12)..(12)
<223> OTHER INFORMATION: y is t or c

<400> SEQUENCE: 231
taagnnnnct ay                                                        12

<210> SEQ ID NO 232
<211> LENGTH: 12
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (2)..(2)
<223> OTHER INFORMATION: y is t or c
<220> FEATURE:
<221> NAME/KEY: misc_feature
<222> LOCATION: (5)..(9)
<223> OTHER INFORMATION: n is a, c, g, or t
<220> FEATURE:
<221> NAME/KEY: misc_feature
<222> LOCATION: (10)..(10)
<223> OTHER INFORMATION: r is g or a

<400> SEQUENCE: 232
cytannnnnr tc                                                        12

<210> SEQ ID NO 233
<211> LENGTH: 13
<212> TYPE: DNA
<213> ORGANISM: Artificial Sequence
<220> FEATURE:
<223> OTHER INFORMATION: Synthetic: Restriction site
<220> FEATURE:
<221> NAME/KEY: misc_feature
<222> LOCATION: (4)..(8)
<223> OTHER INFORMATION: n is a, c, g, or t
<220> FEATURE:
<221> NAME/KEY: misc_feature
<222> LOCATION: (9)..(9)
<223> OTHER INFORMATION: r is g or a
```

```
<220> FEATURE:
<221> NAME/KEY: misc_feature
<222> LOCATION: (13)..(13)
<223> OTHER INFORMATION: y is t or c

<400> SEQUENCE: 233
cccnnnnnrt tgy                                                          13
```

OPTIMIZED VECTOR FOR DELIVERY IN MICROBIAL POPULATIONS

CROSS-REFERENCE TO RELATED APPLICATIONS

This application is a continuation of U.S. application Ser. No. 17/017,111, filed Sep. 10, 2020, which is a continuation of U.S. application Ser. No. 16/527,762, filed Jul. 31, 2019, now U.S. Pat. No. 10,808,254, issued on Oct. 20, 2020, which is a continuation of International Application No. PCT/EP2018/052662, filed on Feb. 2, 2018 which claims the benefit of European Application No. 17305126.9, filed Feb. 3, 2017. The entire disclosures of all of the foregoing applications are incorporated by reference herein.

REFERENCE TO SEQUENCE LISTING SUBMITTED VIA EFS-WEB

This application includes an electronically submitted sequence listing in .txt format. The .txt file contains a sequence listing entitled "2643-11 PCT CON_ST25.txt" created on Oct. 15, 2019 and is 71,165 bytes in size. The sequence listing contained in this .txt file is part of the specification and is hereby incorporated by reference herein in its entirety.

FIELD OF THE INVENTION

The present invention relates to the field of medicine, in particular of bacterial infections. It provides new phage treatment strategy.

BACKGROUND OF THE INVENTION

Nowadays, the treatment of bacterial infections relies mainly on the use of antibiotics. However, excessive and inappropriate use of antibiotics has fostered the emergence and spread of antibiotic-resistant microorganisms. Indeed, infections caused by antibiotic-resistant microorganisms also known as "superbugs" often no longer respond to conventional treatments, thereby extending the duration of the disease related to infection and even leading to patient death. Because of the development of this antibiotic resistance phenomenon and the lack of discovery of new antibiotic classes, humanity is now facing the possibility of a future without effective treatment for bacterial infections.

Moreover, with the recent development of the microbiome field, an increasing number of studies have underlined the harmful consequences of antibiotics treatments. Indeed, due to their low specificity, antibiotics reduce bacterial diversity, which is a keystone of the development and conservation of a healthy microbiome.

Bacteriophages are viruses able to infect and reproduce in specific bacterial species leading most of the time to their death. Since their discovery in 1917, they have been used as therapeutic agents against pathogenic bacteria in Eastern Europe where they continue to be a replacement for antibiotics or a complementary therapy. This method is termed "phage therapy".

Unlike classical chemically-based antibiotics that are active against a broad spectrum of bacterial species, each bacteriophage is able to infect and kill only a small number of different closely-related bacteria. This narrow spectrum of bactericidal activity is one of the major bottlenecks for the use of phage therapy. So far, two methods have been used to bypass the problem of specificity.

The first one consists in using a mixture of different naturally occurring phages, also called a phage cocktail, in which each phage targets a different subset of bacterial strains. The major drawback of such a cocktail is the difficulty of fulfilling the criteria for regulatory approval.

The second method is to broaden the host range of a specific phage by mutation/selection cycles or engineering.

In the mutation/selection cycles strategy, a phage goes through cycles of mutation and selection in the presence of the targeted bacteria. However, this method has several drawbacks. Indeed, these mutation/selection cycles have to be repeated for each targeted strain immune to the phage and the selection of mutations that allow replication in one targeted strain can decrease or abolish the possibility to enter into other strains. Moreover the mutational spectrum (the space of accessible mutation) of phages are limited.

In contrast, phage engineering allows for a more rational approach where specific features of the phage, known to be important for infection, are added or modified. Most of the efforts in phage engineering have focused so far on the ability of a phage to recognize the targeted strain through tail fiber proteins. Swapping tail fibers between two phages can in principle allow for the exchange of their recognition characteristics. As an example, swapping the gp17 tail fiber genes of phage T3 and T7 allowed T7 to extend its host range and infect E. coli strains previously immune to T7 but not to T3 (Pires D P et al, 2016, Microbiology and Molecular Biology Reviews, 80(3): 523-543).

However, tail fiber proteins modifications have shown limited success in broadening bacteriophage host-range.

Furthermore, phage engineering can be a tedious task for several reasons including the phage genome size and the difficulties to operate modifications inside a host (especially if dealing with lytic phages). Thus, researchers have recently been using the phage machinery as a nanocarrier in order to inject DNA of interest in the form of a plasmid inside bacteria. For example, these plasmid-phage hybrids, also called phagemids, have been used to inject a genetic circuit coding for the CRISPR Cas9 nuclease that allows for sequence specific killing of bacteria (Bikard D et al, 2014, Nature Biotechnology, 32(11): 1146-1150; Citorik R J et al, 2014, Nature Biotechnology, 32(11): 1141-1145; WO2015/034872). This strategy was efficient to specifically kill a subpopulation of bacteria containing resistance to a given antibiotic.

However, there is no current real broad spectrum alternative treatment to conventional antibiotics on the market. Therefore, there is still a persisting and urgent medical need to develop new broad-spectrum phage or phagemids therapies capable of efficiently overcome global pathogen resistance, in particular, broad spectrum therapies that will target bacterial pathogen strains without impairing microbiome diversity. The present invention seeks to meet these and other needs.

SUMMARY OF THE INVENTION

The inventors have surprisingly discovered that the main impediment for DNA entry from a phage/phagemid into a target bacterial strain is not related to the specificity of the tail fibers, but rather the number of restriction sites present in its genome. Hence, the same bacteriophage scaffold possessing the same tail fiber proteins can deliver its DNA cargo with varying efficiencies (ranging from 0 to 100%) according to the number of restriction sites present in the cargo. These results address the phage/phagemid host range problem in a totally different way and provide an unexplored path for the design of newly engineered, highly efficient phage or phagemid-based particles Indeed, the aim is now to rationally design phagemids or bacteriophage genomes with a reduced number of restriction sites instead of engineering different attachment and entry points for the viral particles as it has previously been done.

Accordingly, the present invention relates to a bacteriophage or packaged phagemid, wherein the bacteriophage or phagemid does not comprise any restriction site of restriction enzymes which are frequently encoded in a group of bacteria of interest.

In particular, a restriction enzyme is frequently encoded in a group of bacteria of interest when at least 10% of the bacteria of the group of interest encode the restriction enzyme.

Preferably, the group of bacteria of interest consists of a group of n bacterial strains, n being a positive integer comprised between 2 and about 100,000, preferably between 10 and about 10,000. Preferably, the bacterial strains are selected from a single species.

Optionally, the bacteria of interest are selected from the group consisting in *Yersinia* spp., *Escherichia* spp., *Klebsiella* spp., *Acinetobacter* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Vibrio* spp., *Bacillus* spp., *Erysipelothrix* spp., *Salmonella* spp., *Streptomyces* spp., *Streptococcus* spp., *Staphylococcus* spp., *Bacteroides* spp., *Prevotella* spp., *Clostridium* spp., *Bifidobacterium* spp., *Clostridium* spp., *Brevibacterium* spp., *Lactococcus* spp., *Leuconostoc* spp., *Actinobacillus* spp., *Selnomonas* spp., *Shigella* spp., *Zymonas* spp., *Mycoplasma* spp., *Treponema* spp., *Leuconostoc* spp., *Corynebacterium* spp., *Enterococcus* spp., *Enterobacter* spp., *Pyrococcus* spp., *Serratia* spp., *Morganella* spp., *Parvimonas* spp., *Fusobacterium* spp., *Actinomyces* spp., *Porphyromonas* spp., *Micrococcus* spp., *Bartonella* spp., *Borrelia* spp., *Brucella* spp., *Campylobacter* spp., *Chlamydophilia* spp., *Cutibacterium* (formerly *Propionibacterium*) spp., *Ehrlichia* spp., *Haemophilus* spp., *Leptospira* spp., *Listeria* spp., *Mycoplasma* spp., *Nocardia* spp., *Rickettsia* spp., *Ureaplasma* spp., and *Lactobacillus* spp, and a mixture thereof, preferably the bacteria of interest are selected from *Escherichia* spp.

Optionally, the bacteria of interest are selected from the group consisting in *Bacteroides thetaiotaomicron, Bacteroides fragilis, Bacteroides distasonis, Bacteroides vulgatus, Clostridium leptum, Clostridium coccoides, Staphylococcus aureus, Bacillus subtilis, Clostridium butyricum, Brevibacterium lactofermentum, Streptococcus agalactiae, Lactococcus lactis, Leuconostoc lactis, Actinobacillus actinobycetemcomitans, cyanobacteria, Escherichia coli, Helicobacter pylori, Selnomonas ruminatium, Shigella sonnei, Zymomonas mobilis, Mycoplasma mycoides, Treponema denticola, Bacillus thuringiensis, Staphilococcus lugdunensis, Leuconostoc oenos, Corynebacterium xerosis, Lactobacillus plantarum, Lactobacillus rhamnosus, Lactobacillus casei, Lactobacillus acidophilus, Enterococcus faecalis, Bacillus coagulans, Bacillus cereus, Bacillus popillae, Synechocystis* strain PCC6803, *Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Streptomyces phaechromogenes, Streptomyces ghanaensis, Klebsiella pneumoniae, Enterobacter cloacae, Enterobacter aerogenes, Serratia marcescens, Morganella morganii, Citrobacter freundii, Pseudomonas aerigunosa, Parvimonas micra, Prevotella intermedia, Fusobacterium nucleatum, Prevotella nigrescens, Actinomyces israelii, Porphyromonas endodontalis, Porphyromonas gingivalis Micrococcus luteus, Bacillus megaterium, Aeromonas hydrophila, Aeromonas caviae, Bacillus anthracis, Bartonella henselae, Bartonella Quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Campylobacter coli, Campylobacter fetus, Chlamydia pneumoniae, Chlamydia trachomatis, Chlamydophila psittaci, Clostridium botulinum, Clostridium difficile, Clostridium perfringens, Clostridium tetani, Corynebacterium diphtheria, Cutibacterium acnes* (formerly *Propionibacterium* acnes), *Ehrlichia canis, Ehrlichia chaffeensis, Enterococcus faecium, Francisella tularensis, Haemophilus influenza, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumonia, Neisseria gonorrhoeae, Neisseria meningitides, Nocardia asteroids, Rickettsia rickettsia, Salmonella enteritidis, Salmonella typhi, Salmonella paratyphi, Salmonella typhimurium, Shigella flexnerii, Shigella dysenteriae, Staphylococcus saprophyticus, Streptococcus pneumoniae, Streptococcus pyogenes, Streptococcus viridans, Treponema pallidum, Ureaplasma urealyticum, Vibrio cholera, Vibrio parahaemolyticus, Yersinia pestis, Yersinia enterocolitica, Yersinia pseudotuberculosis, Actinobacter baumanii, Pseudomonas aerigunosa*, and a mixture thereof, preferably the bacteria of interest are selected from the group consisting of *Escherichia coli, Enterococcus faecium, Staphylococcus aureus, Klebsiella pneumoniae, Acinetobacter baumanii, Pseudomonas aeruginosa, Enterobacter cloacae*, and *Enterobacter aerogenes*, and a mixture thereof, more preferably the bacteria of interest are selected from *Escherichia coli* strains.

In one embodiment, the bacteria of interest are selected from a group of Table 1 or 2 and the bacteriophage or phagemid does not comprise at least one restriction site selected from the list of restriction sites of Table 1 or 2 corresponding to the group of bacteria of interest. Preferably, the bacteriophage or phagemid does not comprise the restriction sites of the list of restriction sites of Table 1 or 2 corresponding to the group of bacteria.

In one embodiment, the bacteria of interest are selected from *Escherichia coli* strains and the bacteriophage or phagemid does not comprise at least one restriction site selected from the group consisting of CACNNNNNNNCTGG (SEQ ID NO: 1); AACNNNNNNGTGC (SEQ ID NO: 2); AACNNNNCTTT (SEQ ID NO: 4); CACNNNNGTAY (SEQ ID NO: 3); GGTCTC (SEQ ID NO: 36); CTGCAG (SEQ ID NO: 37); and, GAAABCC (SEQ ID NO: 34). Preferably, the bacteriophage or phagemid does not comprise the restriction sites CACNN NNNNCTGG (SEQ ID NO: 1); CTGCAG (SEQ ID NO: 37); and, GAAABCC (SEQ ID NO: 34). Optionally, the bacteriophage or phagemid does not comprise the restriction sites CACNNNNNNNCTGG (SEQ ID NO: 1); CTGCAG (SEQ ID NO: 37); and, GAAABCC (SEQ ID NO: 34), preferably the restriction sites CACNNNNNNNCTGG (SEQ ID NO: 1); AACNNNNNNGTGC (SEQ ID NO: 2); AACNNNNCTTT (SEQ ID NO: 4); CACNNNNGTAY (SEQ ID NO: 3); GGTCTC (SEQ ID NO: 36); CTGCAG (SEQ ID NO: 37); and, GAAABCC (SEQ ID NO: 34).

Optionally, the bacteriophage is selected from the group consisting of IKe, CTX-φ, Pf1, Pf2, Pf3, Myoviridae (such as P1-like, P2-like, Mu-like, SPOT-like, and phiH-like bacteriophages); Siphoviridae (such as λ-like, γ-like, T1-like, c2-like, L5-like, psiM1-like, phiC31-like, and N15-like bacteriophages); Podoviridae (such as phi29-like, P22-like, and N4-like bacteriophages); Tectiviridae (such as Tectivirus); Corticoviridae (such as Corticovirus); Lipothrixviridae (such as Alphalipothrixvirus, Betalipothrixvirus, Gammalipothrixvirus, and Deltalipothrixvirus); Plasmaviridae (such as Plasmavirus); Rudiviridae (such as Rudivirus); Fuselloviridae (such as Fusellovirus); Inoviridae (such as Inovirus, Plectrovirus, M13-like and fd-like bacteriophages); Microviridae (such as Microvirus, Spiromicrovirus, Bdellomicrovirus, and Chlamydiamicrovirus); Leviviridae (such as Levivirus, and Allolevivirus), Cystoviridae (such as Cystovirus), coliphages (e.g., infects *Escherichia coli*), B1 (e.g. infects *Bacteroides thetaiotamicron*), ATCC 51477-B1, B40-8, or Bf-1 (e.g. infects *B. fragilis*), phiHSCO1—e.g. infects *B. caccae*), phiHSC02 (e.g. infects *B. ovatus*), phiC2, phiC5, phiC6, phiC8, phiCD119, or phiCD27 (e.g. infects *Clostridium difficile*), KPO1K2, K1 1, Kpn5, KP34, or JDOO1 (e.g. infects *Klebsiella pneumoniae*), phiNM1 or 80alpha (e.g. infects *Staphylococcus aureus*), IME-EF1 (e.g. infects *Enterococcus faecalis*), ENB6 or C33 (e.g. infects *Enterococcus faecium*), and phiKMV, PAK-P1, LKD16, LKA1, delta, sigma-1, J-1 (e.g. infects *Pseudomonas aeruginosa*), T2, T4, T5, T7, RB49, phiX174, R17, PRD1 bacteriophages, or the phagemid is packaged into the capsid of one of these bacteriophages.

Optionally, the phagemid is selected from the group consisting of lambda derived phagemids, P4 derived phagemids, M13-derived phagemids, such as the ones containing the f1 origin for filamentous phage packaging such as, for example, pBluescript II SK (+/−) and KS (+/−) phagemids, pBC SK and KS phagemids, pADL and P1 derived phagemids, preferably phagemids according to the invention are selected from lambda derived phagemids and P4 derived phagemids, more preferably, phagemids according to the invention are selected from lambda derived phagemids, preferably selected from the group consisting of HK022 derived phagemids, mEP237 derived phagemids, HK97 derived phagemids, HK629 derived phagemids, HK630 derived phagemids, mEP043 derived phagemids, mEP213 derived phagemids, mEP234 derived phagemids, mEP390 derived phagemids, mEP460 derived phagemids, mEPx1 derived phagemids, mEPx2 derived phagemids, phi80 derived phagemids, mEP234 derived phagemids.

In a second aspect, the invention concerns the use of a bacteriophage or of a packaged phagemid according to the invention to infect a bacterium, preferably a bacterium selected from said group of bacteria of interest.

In a third aspect, the invention also concerns a pharmaceutical or veterinary composition comprising or consisting essentially of a bacteriophage or a packaged phagemid according to the invention.

The invention yet concerns, in a forth aspect, a bacteriophage or packaged phagemid according to the invention, or the pharmaceutical or veterinary composition according to the invention for use as a drug, especially for improving the general health of a subject, for eradicating pathogenic or virulent bacteria, for improving the effectiveness of drugs, and/or for modifying the composition of the microbiome, in particular for the treatment of infections, inflammatory diseases, auto-immune diseases, cancers, and brain disorders.

Preferably, the infection is a bacterial infection, preferably caused by a bacterium selected among the group of bacteria of interest.

BRIEF DESCRIPTION OF THE DRAWINGS

FIG. 1: Injection efficiency of wild-type Lambda phage and Lambda-based phagemids. A) A set of 89 *E. coli* strains was treated with wild-type Lambda phage particles (48.5 kb genome) and the injection efficiency assessed by plaque formation. White, plaques present; Grey, no plaques; Crossed, strain didn't grow (not analyzed). B) The same strains shown in (A) were treated with a packaged Lambda phagemid carrying a 3.3 kb DNA cargo coding for chloramphenicol resistance and GFP. White, fluorescent colonies present; Grey, no colonies; Crossed, strain was naturally resistant to chloramphenicol (not analyzed). C) Examples of strains from (A) and (B) showing that the 3.3 kb packaged Lambda-based phagemid is able to inject into the target strain (bottom row) while Lambda wild-type bacteriophage is not (top row).

FIG. 3. Growth of 87 different strains of *E. coli* after transductions with Lambda phagemids: 8 kb WT and 8 kb RF (A), 3 kb WT and 3 kb RF (B). Individual strains are indicated by the positions on a 96-well plate. Strains that exhibited growth (more than ten colonies visible per spot plated) are indicated in gray. Positions of the 96-well plate that were not included in the analysis are indicated in black. Position B7 contains the permissive control strain, *E. coli* MG1655, which exhibited growth after transductions with all the phagemids tested. A higher number of strains was transduced with Lambda phagemids 8 kb and 3 kb RF, which are cleaned of the majority of restriction sites recognized by the *E. coli* RM nucleases, compared to the corresponding WT phagemid variants, which have not been depleted of restriction sites.

DETAILED DESCRIPTION OF THE INVENTION

Figure 2:
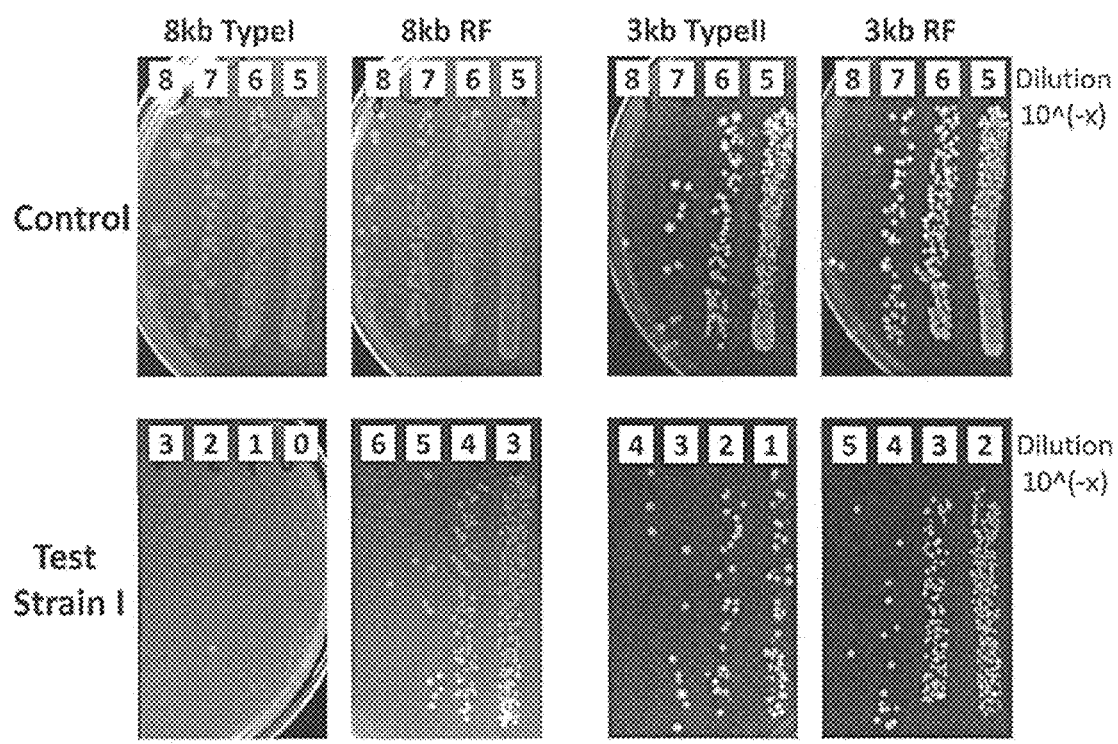
FIG. 2. The efficiencies of transduction of Lambda phagemids: 8 kb TypeI and 8 kb RF (A), 3 kb TypeI and 3 kb RF (B) to Test Strain 1 and the permissive control strain (Control), assessed by CFUs. Lambda phagemids 8 kb and 3 kb RF are cleaned of restriction sites recognized by the RM nucleases of Test Strain 1, whereas Lambda phagemids 8 kb TypeI and 3 kb TypeII contain single restriction sites. The control strain is permissive for both RF and non-restriction-free Lambda phagemids. The dilutions [10^(-given number)] of the phagemids used for transduction are indicated above each streak. The streaks with the phagemid dilutions that gave the highest number of individual countable CFUs were used for calculation of the phagemid titers.

The inventors have surprisingly discovered that the main impediment for DNA delivery from a phage/phagemid into a target bacterial strain is not related to the specificity of bacteriophage, especially its tail fibers, but rather to the number of restriction sites present in its genome. Hence, the same bacteriophage scaffold possessing the same tail fiber proteins can deliver its DNA cargo with varying efficiencies (ranging from 0 to 100%) according to the number of restriction sites present in its genome and recognized by the restriction enzymes of the group of targeted bacteria. The inventors have thus discovered a new strategy for the design of engineered, highly efficient phagemid-based particles that rely on a reduction in the number of restriction sites, thereby improving the spectrum in a group of targeted bacteria.

Definitions

Unless defined otherwise, all technical and scientific terms used herein have the same meaning as commonly understood by one of ordinary skilled in the art to which this invention belongs. Although any methods and materials similar or equivalent to those described herein can be used in the practice or testing of the present invention, the preferred methods and materials are described. All patents and scientific literature cited in this application evidence the level of knowledge in this field and are hereby incorporated by reference. For purposes of clarification, the following terms are defined below.

As used herein, the term "nucleic acid" refers to at least two nucleotides covalently linked together, and in some instances, may contain phosphodiester bonds (e.g., a phosphodiester "backbone"). In some embodiments, a nucleic acid of the present disclosure may be considered to be a nucleic acid analog, which may contain other backbones comprising, for example, phosphoramide, phosphorothioate, phosphorodithioate, O-methylphophoroamidite linkages, and/or peptide nucleic acids. Nucleic acids (e.g., components, or portions, of the nucleic acids) of the present disclosure may be naturally occurring or engineered. Engineered nucleic acids include recombinant nucleic acids and synthetic nucleic acids. "Recombinant nucleic acids" may refer to molecules that are constructed by joining nucleic acid molecules and, in some embodiments, can replicate in a living cell. "Synthetic nucleic acids" may refer to molecules that are chemically or by other means synthesized or amplified, including those that are chemically or otherwise modified but can base pair with naturally occurring nucleic acid molecules. Recombinant and synthetic nucleic acids also include those molecules that result from the replication of either of the foregoing. The nucleic acids may be single-stranded (ss) or double-stranded (ds), as specified, or may contain portions of both single-stranded and double-stranded sequences. The nucleic acid may be DNA, both genomic and cDNA, RNA or a hybrid/chimeric, where the nucleic acid contains any combination of deoxyribo- and ribonucleotides, and any combination of bases, including uracil, adenine, thymine, cytosine, guanine, inosine, xanthine, hypoxanthine, isocytosine, and isoguanine. Preferably, recombinant and synthetic nucleic acid is not naturally occurring, especially it includes two sequences that are not found on the same nucleic acid molecule in nature.

As used herein, the terms "vector" and "DNA cargo" are equivalent and refer to a nucleic acid molecule, typically DNA or RNA that serves to transfer a passenger nucleic acid sequence, i.e. DNA or RNA, into a host cell. A vector may comprise an origin of replication, a selectable marker, and optionally a suitable site for the insertion of a gene such as the multiple cloning site. There are several common types of vectors including plasmids, bacteriophage genomes, phagemids, virus genomes, cosmids, and artificial chromosomes. By "vector" it can be referred to a phagemid or a bacteriophage genome.

As used herein, the term "expression vector" refers to a vector designed for gene expression in cells. An expression vector allows to introduce a specific gene into a target cell, and can commandeer the cell's mechanism for protein synthesis to produce the protein encoded by the gene. An expression vector comprises expression elements including, for example, a promoter, the correct translation initiation sequence such as a ribosomal binding site and a start codon, a termination codon, and a transcription termination sequence. An expression vector may also comprise other regulatory regions such as enhancers, silencers and boundary elements/insulators to direct the level of transcription of a given gene. The expression vector can be a vector for stable or transient expression of a gene.

As used herein, the term "delivery vehicle" refers to a structure or composition that allow the transfer of a vector into a bacterium. There is several common types of delivery vehicle including bacteriophage scaffold, virus scaffold, chemical based delivery vehicle (e.g., cyclodextrin, calcium phosphate, cationic polymers, cationic liposomes), nanoparticle-based delivery vehicles (or platforms), non-chemical-based delivery vehicles (e.g., electroporation, sonoporation, optical transfection), particle-based delivery vehicles (e.g., gene gun, magnetofection, impalefection, particle bombardment, cell-penetrating peptides) or donor bacteria.

As used herein, the term "conjugative plasmid" refers to a plasmid that is transferred from one bacterial cell to another during conjugation and a "donor bacterium", as used herein, is a bacterium that is capable of transferring a conjugative plasmid to another bacterium.

As used herein, the terms "bacteriophage" or "phage" are equivalent and refer to a virus that infects and replicates in a bacterium. Bacteriophages are composed of a bacteriophage scaffold and of a bacteriophage genome. The bacteriophage genome can be wildtype or genetically engineered. In particular, the bacteriophage is an engineered bacteriophage. By "engineered" is intended that the bacteriophage genome has been genetically engineered, especially by removing some restriction sites.

As used herein, the terms "bacteriophage scaffold", "capsid", or "coat proteins" are equivalent and refers to the proteins that encapsulate the bacteriophage genome, phagemid or plasmid. Preferably, they refer to bacteriophage capsids or coat proteins.

The term "bacteriophage genome", as used herein, refers to the DNA or RNA genome that is packaged in a bacteriophage scaffold. The bacteriophage genome can be wildtype or genetically engineered.

The term "lethal bacteriophage", as used herein, refers to a bacteriophage that, following the injection of its genome into the cytoplasm of a bacteria, lead to the death of the bacteria. Lethal bacteriophages according to the invention include but are not limited to bacteriophages having a lytic cycle of replication resulting in bacterial cell lysis.

The term "non-lethal bacteriophage", as used herein, refers to a bacteriophage that, following the injection of its genome into the cytoplasm of a bacteria, will not lead to the death of the bacteria. In particular, non-lethal bacteriophages according to the invention present a non-lytic cycle of replication, which leaves the bacterial cell intact. The bacteriophage of the present invention may be, in some embodiments, a non-lethal bacteriophage.

In a preferred embodiment, the bacteriophage according to the invention is a lethal bacteriophage.

As used herein, the term "phagemid" or "phasmid" are equivalent and refer to a vector that derives from both a plasmid and a bacteriophage genome. A phagemid of the invention comprises a phage packaging site and optionally an origin of replication (ori), in particular a bacterial and/or phage origin of replication. In one embodiment, the phagemid according to the invention does not comprise a bacterial origin of replication and thus cannot replicate by itself once injected into a bacterium. Alternatively, the phagemid according to the invention comprises a plasmid origin of replication, in particular a bacterial and/or phage origin of replication. According to the invention, the term phagemid is not limited to vectors having f1 origin of replication.

As used herein, the term "packaged phagemid" or "engineered particle derived from a phagemid" refers to a phagemid which is encapsidated in a bacteriophage scaffold or capsid. Particularly, it refers to a bacteriophage scaffold or capsid devoid of a bacteriophage genome.

The packaged phagemid according to the invention may be produced with a helper phage strategy, well known from the man skilled in the art. The helper phage comprises all the genes coding for the structural and functional proteins that are indispensable for the phagemid according to the invention to be encapsidated.

The packaged phagemid according to the invention may be produced with a satellite virus strategy, also known from the man skilled in the art. Satellite virus are subviral agent and are composed of nucleic acid that depends on the co-infection of a host cell with a helper virus for all the morphogenetic functions, whereas for all its episomal functions (integration and immunity, multicopy plasmid replication) the satellite is completely autonomous from the helper. In one embodiment, the satellite genes can encode proteins that promote capsid size reduction of the helper phage, as described for the P4 Sid protein that controls the P2 capsid size to fit its smaller genome.

The term "lethal packaged phagemid", as used herein, refers to a packaged phagemid that, following the injection of its genome into the cytoplasm of a bacterium, lead to the death of the bacterium.

The term "non-lethal packaged phagemid", as used herein, refers to a phagemid that, following the injection of its genome into the cytoplasm of a bacterium, will not lead to the death of the bacterium.

In a preferred embodiment, the packaged phagemid according to the invention is a lethal packaged phagemid.

Alternatively, the packaged phagemid according to the invention is a non-lethal packaged phagemid.

As used herein, the terms "promoter" and "transcriptional promoter" are equivalent and refer to a control region of a nucleic acid sequence at which transcription initiation and rate of transcription of the remainder of a nucleic acid sequence are controlled. A promoter may also contain subregions to which regulatory proteins and molecules may bind, such as RNA polymerase and other transcription factors. A promoter drives transcription of the nucleic acid sequence that it regulates. Herein, a promoter is considered to be "operably linked" when it is in a correct functional location and orientation in relation to a nucleic acid sequence it regulates to control ("drive") transcriptional initiation of that sequence.

A promoter may be classified as strong or weak according to its affinity for RNA polymerase (and/or sigma factor); this is related to how closely the promoter sequence resembles the ideal consensus sequence for the polymerase or sigma factor. The strength of a promoter may depend on whether initiation of transcription occurs at that promoter with high or low frequency. Different promoters with different strengths may be used in the present invention leading to different levels of gene/protein expression (e.g. the level of expression initiated from an mRNA originating from a weak promoter is lower than the level of expression initiated from a strong promoter).

A promoter may be one naturally associated with a gene or sequence, as may be obtained by isolating the 5' non-coding sequences located upstream of the coding segment of a given gene or sequence. Such a promoter can be referred to as "endogenous." Similarly, an activator/enhancer may be one naturally associated with a nucleic acid sequence, located either within or downstream or upstream of that sequence.

In some embodiments, a coding nucleic acid segment may be positioned under the control of a recombinant or heterologous promoter, which refers to a promoter that is not normally associated with the encoded nucleic acid sequence in its natural environment. A recombinant or heterologous enhancer refers to an enhancer not normally associated with a nucleic acid sequence in its natural environment.

As used herein, an "inducible promoter" is one that is characterized by initiating or enhancing transcriptional activity when in the presence of, influenced by or contacted by an inducer or inducing agent. An "inducer" or "inducing agent" may be endogenous or a normally exogenous condition, compound or protein that induces transcriptional activity from the inducible promoter. Examples of inducible promoters for use herein include, without limitation, bacteriophage promoters (e.g. Plslcon, T3, T7, SP6, PL) and bacterial promoters (e.g. Pbad, PmgrB, Ptrc2, Plac/ara, Ptac, Pm), or hybrids thereof (e.g. PLlacO, PLtetO).

Examples of bacterial promoters for use in accordance with the present invention include, without limitation, positively regulated E. coli promoters such as positively regulated σ 70 promoters (e.g., inducible pBad/araC promoter, Lux cassette right promoter, modified lamdba Prm promote, plac Or2-62 (positive), pBad/AraC with extra REN sites, pBad, P(Las) TetO, P(Las) CIO, P(Rh1), Pu, FecA, pRE, cadC, hns, pLas, pLux), a "s" promoter (e.g., Pdps), σ 32 promoters (e.g., heat shock) and σ 54 promoters (e.g., glnAp2); negatively regulated E. coli promoters such as negatively regulated σ 70 promoters (e.g., Promoter (PRM+), modified lamdba Prm promoter, TetR-TetR-4C P(Las) TetO, P(Las) CIO, P(Lac) IQ, RecA_DlexO_D-Lac01, dapAp, FecA, Pspac-hy, pel, plux-cl, plux-lac, CinR, CinL, glucose controlled, modifed Pr, modifed Prm+, FecA, Pcya, rec A (SOS), Rec A (SOS), EmrR_regulated, Betl_regulated, pLac_lux, pTet_Lac, pLac/Mnt, pTet/Mnt, LsrA/cI, pLux/cI, Lad, LacIQ, pLacIQ1, pLas/cI, pLas/Lux, pLux/Las, pRecA with LexA binding site, reverse BBa R0011, pLacPara-1, pLacIq, rrnB PI, cadC, hns, PfhuA, pBad/araC, nhaA, OmpF, RcnR), σ S promoters (e.g., Lutz-Bujard LacO with alternative sigma factor σ 38), σ 32 promoters (e.g., Lutz-Bujard LacO with alternative sigma factor σ 32), σ 54 promoters (e.g., glnAp2); negatively regulated B. subtilis promoters such as repressible B. subtilis σ A promoters (e.g., Gram-positive IPTG-inducible, Xyl, hyper-spank), a promoters, and the BioFAB promoters disclosed in Mutalik V K et al (Nature Methods, 2013, 10: 354-360, see in particular the supplementary data) as well as on the BioFAB web site (biofab.synberc.org/data). Other inducible microbial promoters and/or bacterial promoters may be used in accordance with the present invention. An inducible promoter for use in accordance with the present disclosure may be induced by (or repressed by) one or more physiological condition(s), such as changes in pH, temperature, radiation, osmotic pressure, saline gradients, cell surface binding, and the concentration of one or more extrinsic or intrinsic inducing agent(s). The extrinsic inducer or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof.

Particularly preferred bacterial promoters for use in accordance with the present invention may be selected from constitutive promoters regulated by σ 70 such as the promoters of the Anderson collection (parts.igem.org/Promoters/Catalog/Anderson): BBa_J23100, BBa_J23101, BBa_J23102, BBa_J23103, BBa_J23104, BBa_J23105, BBa_J23106, BBa_J23107, BBa_J23108, BBa_J23109, BBa_J23110, BBa_J23111, BBa_J23112, BBa_J23113, BBa_J23114, BBa_J23115, BBa_J23116, BBa_J23117, BBa_J23118, and BBa_J23119.

In some embodiments of the present invention, a promoter may or may not be used in conjunction with an "enhancer," which refers to a ds-acting regulatory sequence involved in the transcriptional activation of a nucleic acid sequence downstream of the promoter. The enhancer may be located at any functional location before or after the promoter.

In some embodiments, a vector of the invention may comprise a terminator sequence, or terminator. A "terminator," as used herein, is a nucleic acid sequence that causes transcription to stop. A terminator may be unidirectional or bidirectional. It is comprised of a DNA sequence involved in specific termination of an RNA transcript by an RNA polymerase. A terminator sequence prevents transcriptional activation of downstream nucleic acid sequences by upstream promoters. Thus, in certain embodiments, a terminator that ends the production of an RNA transcript is contemplated. A terminator may be necessary in vivo to achieve desirable gene/protein expression levels.

The most commonly used type of terminator is a forward terminator. When placed downstream of a nucleic acid sequence that is usually transcribed, a forward transcriptional terminator will cause transcription to abort. In some embodiments, bidirectional transcriptional terminators are provided, which usually cause transcription to terminate on both the forward and reverse strand. In some embodiments, reverse transcriptional terminators are provided, which usually terminate transcription on the reverse strand only. In prokaryotic systems, terminators usually fall into two categories (1) rho-independent terminators and (2) rho-dependent terminators. Rho-independent terminators are generally composed of palindromic sequence that forms a stem loop rich in G-C base pairs followed by a string of uracil bases.

Terminators for use in accordance with the present invention include any terminator of transcription described herein or known to one of ordinary skill in the art. Examples of terminators include, without limitation, the termination sequences of genes such as, for example, the bovine growth hormone terminator, and viral termination sequences such as, for example, the TO terminator, the TE terminator, Lambda T1 and the T1T2 terminator found in bacterial systems. In some embodiments, the termination signal may be a sequence that cannot be transcribed or translated, such as those resulting from a sequence truncation.

Terminators for use in accordance with the present invention also include terminators disclosed in Chen Y J et al (2013, Nature Methods, 10: 659-664), and the BioFAB terminators disclosed in Cambray G et al (Nucl Acids Res, 2013, 41(9): 5139-5148).

Other genetic elements are known in the art and may be used in accordance with the present disclosure.

As used herein, the term "codon usage table" refers to a database giving the codons, the amino acid encoded by each codon, and the frequency at which these codons are found for a defined type of amino acid.

As used herein, the term "meet the codon usage" refers to an optimization of the codon frequencies in a nucleic acid in order to be the closest as possible to the codon frequencies in the codon usage table for a considered host or group of hosts.

As used herein, the term "modification", "change", and "mutation" are used interchangeably and refer to a change in an amino acid or nucleic acid sequence such as a substitution, an insertion, and/or a deletion.

By "substitution" herein is meant the replacement of a nucleotide or an amino acid at a particular position in a parent nucleic acid or amino acid sequence with another nucleotide or amino acid.

By "insertion" is meant the addition of a nucleic acid or amino acid at a particular position in a parent nucleic acid or amino acid sequence.

By "deletion" is meant the removal of a nucleotide or amino acid at a particular position in a parent acid nucleic or amino acid sequence.

The nucleotide substitution may be neutral. A neutral nucleotide substitution is the replacement of a given nucleotide by another nucleotide, resulting in a codon that codes for the same amino acid. Codons that code for the same amino acid are given by a codon usage table.

As used herein, the term "parent sequence" refers to a nucleic acid or amino acid sequence that is subsequently modified to generate a variant. This term also refer to a sequence of reference that can be a naturally occurring sequence or an engineered sequence in which the mutation(s) or modification(s) will be made to generate a variant. The "parent sequence" may refer to a vector sequence such as a phagemid sequence.

As used herein, the terms "variant sequence" or "variant" are equivalent and refer to a nucleic acid sequence or an amino acid sequence that differs from that of a parent sequence by virtue of at least one modification. The variants may comprise one or several substitutions, and/or, one or several insertions, and/or one or several deletions. In some embodiments, the nucleic acid variant may comprise one or several neutral substitutions. In some other embodiments, the amino acid variant may comprise one or several conservative substitutions.

As used herein, the terms "restriction site" and "restriction enzyme site" are equivalent and refer to locations on a nucleic acid containing specific sequences of nucleotides, which are recognized by restriction enzymes. In particular, the nucleic acid comprises specific sequences which are bound and cleaved by restriction enzymes. Restriction sites are generally palindromic sequences of 4-8 base pairs in length. More precisely, the restriction site refers to a particular sequence and a modification state, so as to be bound and cleaved by restriction enzymes. In particular, it refers to a particular unmodified sequence, so as to be bound and cleaved by restriction enzymes. Especially the sequence is not methylated, hydroxymethylated and glucosyl-hydroxymethylated. In this context, the restriction enzyme is of type I, II or III. Alternatively, it may refer to a particular modified sequence, so as to be bound and cleaved by restriction enzymes, for instance a methylated, hydroxymethylated and glucosyl-hydroxymethylated DNA. In this context, the restriction enzyme is of type IV.

As used herein, "recognized by" with respect to a restriction site and a restriction enzyme means that the restriction site is cleaved by the restriction enzyme.

In a restriction site sequence N means that the nucleotide can be A, C, G or T; B means that the nucleotide can be C, G or T; Y means that the nucleotide can be C or T; W means that the nucleotide can be A or T; R means that the nucleotide can be A or G; and D means A, G or T.

As used herein, the terms "restriction enzyme" and "restriction endonuclease" are equivalent and refer to an enzyme that cuts nucleic acids at or near restriction sites. Restriction enzymes are commonly classified into four types (types I to type IV). The REBASE database allow to list the restriction sites that a given bacterium can recognize according to the restriction enzymes that it expresses.

As used herein, the term "bacterium" or "bacteria" refers to any prokaryotic microorganisms that exist as a single cell or in a cluster or aggregate of single cells. The term "bacterium" encompasses all variants of bacteria (e.g., endogenous bacteria, which naturally reside in a closed system, environmental bacteria or bacteria released for bioremediation or other efforts). Bacteria of the present disclosure include bacterial subdivisions of Eubacteria and Archaebacteria. Eubacteria can be further subdivided into Gram-positive and Gram-negative Eubacteria, which depend upon a difference in cell wall structure. Also included herein are those classified based on gross morphology alone (e.g., cocci, bacilli). In some embodiments, the bacteria are Gram-negative cells, and in some embodiments, the bacteria are Gram-positive cells.

As used herein, the term "microbiome" or "microbiota" are equivalent and refers to the ecological community of commensal, symbiotic, and pathogenic microorganisms that literally share the body space of a subject. Preferably a human subject.

The microbiome can be specific of a given species, body area, body part, organ or tissue. As such, the term human microbiome, as used herein, refers to the ecological community of commensal, symbiotic, and pathogenic microorganisms that comprise the microbiome of humans.

As used herein, the term "infection" refers to the invasion of an organism's body tissues by disease-causing bacteria, their multiplication, and the reaction of host tissues to these bacteria and eventually the toxins they produce.

The terms "infectious agent", "microbial agent", "pathogen", "disease-causing microorganism", and "virulent bacterium", as used herein, are equivalent and refer to a bacterium that causes infection.

Virulent bacteria according to the invention also include antibacterial resistance bacteria.

As used herein, the term "selection marker" refers to a gene which is used to confirm the cloning of a gene or to confirm or ensure the presence of a plasmid in a bacterium. The selection marker can be a marker gene providing selectable phenotypes such as drug resistance, auxotrophy, resistance to cytotoxic agents, or surface protein expression. For example, an antibiotic-resistant gene, a gene allowing to overcome auxotrophy, a colour-developing enzyme gene or a luminescent/fluorescent gene may be used. This confers a "selective advantage" to bacteria carrying such selection marker so as to be able to grow on medium supplied with antibiotics, heavy metals, or on medium without essential component such as amino acid.

As used herein, the terms "antibiotic" and "antibacterial" are equivalent and refer to a type of antimicrobial active ingredient used in the treatment and prevention of bacterial infections.

The terms "antibacterial resistance", as used herein, refers to the ability of a bacterium to resist the effects of medication previously used to treat them.

As used herein, the term "treatment", "treat" or "treating" refers to any act intended to ameliorate the health status of patients such as therapy, prevention, prophylaxis and retardation of the infection. In certain embodiments, such term refers to the amelioration or eradication of the infection or symptoms associated with it. In other embodiments, this term refers to minimizing the spread or worsening of the infection resulting from the administration of one or more therapeutic agents to a subject with such a disease.

As used herein, the terms "subject", "individual" or "patient" are interchangeable and refer to an animal, preferably to a mammal, even more preferably to a human, including adult, child, new-borns and human at the prenatal stage. However, the term "subject" can also refer to non-human animals, in particular mammals such as dogs, cats, horses, cows, pigs, sheep, donkeys, rabbits, ferrets, gerbils, hamsters, chinchillas, rats, mice, guinea pigs and non-human primates, among others, that are in need of treatment.

The terms "quantity," "amount," and "dose" are used interchangeably herein and may refer to an absolute quantification of a molecule.

As used herein, the terms "active principle", "active ingredient" and "active pharmaceutical ingredient" are equivalent and refers to a component of a pharmaceutical composition having a therapeutic effect.

As used herein, the term "therapeutic effect" refers to an effect induced by an active ingredient, a pharmaceutical or veterinary composition, a kit, a product or a combined preparation according to the invention, capable to prevent or to delay the appearance of an infection, or to cure or to attenuate the effects of an infection.

As used herein, the term "effective amount" refers to a quantity of an active ingredient or of a pharmaceutical or veterinary composition which prevents, removes or reduces the deleterious effects of the infection. It is obvious that the quantity to be administered can be adapted by the man skilled in the art according to the subject to be treated, to the nature of the infection, etc. In particular, doses and regimen of administration may be function of the nature, of the stage and of the severity of the infection to be treated, as well as of the weight, the age and the global health of the subject to be treated, as well as of the judgment of the doctor.

As used herein, the term "consisting essentially in" is intended to refer to a pharmaceutical or veterinary composition that does not comprise any other active ingredient.

In the present document, the term «about» refers to a range of values of ±10% of the specified value. For example, «about 50» comprise values off 10% of 50, i.e. values in the range between 45 and 55. Preferably, the term «about» refers to a range of values of +5% of the specified value.

The present invention relates to a vector having a reduced number of restriction sites with respect to a group of bacteria of interest, the vector packaged into a bacteriophage scaffold and the uses and methods using the vector packaged into a bacteriophage scaffold. In other words, it has a low number of restriction sites corresponding restriction enzymes encoded by a group of bacteria of interest. By low number is preferably understood that the vector comprises no more than 10, 9, 8, 7, 6, 5, 4, 3, 2, 1 restriction site(s). In a preferred embodiment, the vector has no restriction site for restriction enzymes encoded by a group of bacteria of interest or for a group of restriction enzymes which are highly present in a group of bacteria of interest. However, the choice to the restriction sites to be removed from the vector depends on the number of bacteria from the bacteria of interest which encodes a restriction enzyme.

Number of Restriction Site

The vector according to the invention is such as it contains no or only few restriction sites of restriction enzymes encoded by a group of bacteria of interest.

More particularly, when some restriction enzymes encoded by a group of bacteria of interest are frequent, in particular highly frequent, in the group of bacteria of interest, then their restriction sites are rare or absent in the vector according to the invention, preferably absent. By "rare" is meant that 1 or 2 occurrences of the restriction sites in the vector. In a preferred embodiment, the restriction sites are absent from the vector according to the invention.

By "frequent" or "frequently" in a group of bacteria of interest is meant that at least 10, 20, 30, 40, 50, 60, 70, 75, 80, 85, 90, 95 or 99% of the bacteria of the group encode the restriction enzyme. By "highly frequent" in a group of bacteria of interest is meant that at least 50, 60, 70, 75, 80, 85, 90, 95 or 99% of the bacteria of the group encode the restriction enzyme. In case that several restriction enzymes have the same restriction site, the number of these restriction enzymes is taken into account for determining the frequency. More particularly, the sum of the occurrences of these restriction enzymes is considered for determining the frequency. The frequency can be determined based on the coding sequences present in the bacteria, on the genome of the bacteria or on the coding sequence of extrachromosomal or mobile genetic elements (also called the accessory genome) of the bacteria that comprise but are not limited to plasmid sequence, transposon sequence, chromosomic cassette sequence and genomic islet sequence. It will be considered that the bacterium encodes the restriction enzyme if its genome or its accessory genome as described above comprises the sequence encoding the restriction enzyme.

In one embodiment, the vector according to the invention does not comprise any restriction site of restriction enzymes which are frequent or highly frequent in the group of bacteria of interest.

If some restriction enzymes are encoded by a group of bacteria of interest with low frequency, then their restriction sites are rare in the vector according to the invention. By "rare" is meant that 1 or 2 occurrences of the restriction sites in the vector. In one embodiment, the restriction sites are absent from the vector according to the invention.

In a particular embodiment, "frequent" in a group of bacteria of interest is meant that at least than 10% of the bacteria of the group encodes the restriction enzyme.

In a particular embodiment, the vector according to the invention does not comprise any restriction site of restriction enzymes encoded by more than 10, 15, 20 or 25% of the bacteria of the group of bacteria of interest.

Optionally, if less than 10% of the bacteria from the group encodes the restriction enzyme, then the restriction site can be present in the vector.

The vector according to the invention, preferably included into a delivery vehicle, preferably a bacteriophage capsid, comprises no more than 100 restriction sites. Preferably, the vector according to the invention, preferably included in a delivery vehicle, comprises no more than 90, 80, 70, 60, 50, 40, 30, 20, 10, 9, 8, 7, 6, 5, 4, 3, 2, 1 restrictions site(s). In a preferred embodiment, the vector according to the invention, preferably included in a delivery vehicle, comprises no more than 10 restriction sites. In a most preferred embodiment, the vector according to the invention, preferably included in a delivery vehicle, doesn't comprise any restriction site.

In a particular embodiment, the invention concerns a vector, preferably a vector included in a delivery vehicle, in which at least 10%, 20%, 30%, 40%, 50%, 60%, 70%, 80%, 90%, 99% or 100% of the restriction sites originally present in the vector have been removed. The expression "originally present", as used herein, refers to the number of restriction enzymes naturally present in the vector or present after construction or modification of the vector but before any attempt to reduce the number of restriction enzymes. The man skilled in the art can use restriction sites databases such as the REBASE database to identify all the known restriction sites present in a given vector. Preferably, the restrictions site which are removed are selected among the restriction sites of restriction enzymes which are frequent or highly frequent in the group of bacteria of interest.

Preferably, the vector, preferably a vector included in a delivery vehicle, is such as at least 10%, 20%, 30%, 40%, 50%, 60%, 70%, 80%, 90%, 99% or 100% of the restriction sites originally present in the vector have been removed and preferably the restriction sites are restriction sites of restriction enzymes which are frequent or highly frequent in the group of bacteria of interest.

In a preferred embodiment, the invention concerns a bacteriophage genome or a phagemid comprising no more than 100 restriction sites recognized. Preferably, the bacteriophage genome or phagemid according to the invention comprises no more than 90, 80, 70, 60, 50, 40, 30, 20, 10, 9, 8, 7, 6, 5, 4, 3, 2, 1 restrictions site(s) recognized. In a preferred embodiment, the bacteriophage genome or phagemid according to the invention comprises no more than 10 restriction sites recognized by the restriction enzymes encoded by each bacterium of a group of bacteria of interest. In a most preferred embodiment, the bacteriophage genome or phagemid according to the invention comprises no restriction site.

In a particular embodiment, the invention concerns a bacteriophage genome or a phagemid in which at least 10%, 20%, 30%, 40%, 50%, 60%, 70%, 80%, 90%, 99% of the restriction sites originally present in the bacteriophage genome or the phagemid have been removed. Preferably, the restrictions site which are removed are selected among the restriction sites of restriction enzymes which are frequent or highly frequent in the group of bacteria of interest. Preferably, the vector, preferably a vector included in a delivery vehicle, is such as at least 10%, 20%, 30%, 40%, 50%, 60%, 70%, 80%, 90%, 99% or 100% of the restriction sites originally present in the vector have been removed and the restriction sites are restriction sites of restriction enzymes which are frequent or highly frequent in the group of bacteria of interest.

In a particular embodiment, the invention concerns a bacteriophage or a packaged phagemid in which at least 10%, 20%, 30%, 40%, 50%, 60%, 70%, 80%, 90%, 99% of the restriction sites originally present in the bacteriophage or the packaged phagemid have been removed and preferably the restriction sites are restriction sites of restriction enzymes which are frequent or highly frequent in the group of bacteria of interest.

In a first aspect, the restriction sites are the restriction sites recognized by a bacterial strain of interest, i.e. by the restriction enzyme expressed by the bacterial strain of interest.

In a second aspect, the restriction sites are the restriction sites of restriction enzymes which are frequently encoded in the group of bacteria of interest.

In a third aspect, the restriction sites are the restriction sites recognized by each bacterial strain of a group of bacterial strains of interest, i.e. by the restriction enzymes expressed by each bacterial strain of the bacterial strains of interest. Preferably, the bacterial strains of the group of bacterial strains are from the same bacterial species.

In a fourth aspect, the restriction sites are the restriction sites recognized by a bacterial species of interest, i.e. by the restriction enzyme expressed by the bacterial species of interest.

In a fifth aspect, the restriction sites are the restriction sites recognized by each bacterial species of a group of bacterial species of interest, i.e. by the restriction enzymes expressed by each bacterial species of the bacterial species of interest. Preferably, the bacterial species of the group of bacterial species are from the same bacterial genus.

In a sixth aspect, the restriction sites are the restriction sites recognized by a bacterial genus of interest, i.e. by the restriction enzyme expressed by the bacterial genus of interest.

In a seventh aspect, the restriction sites are all the restriction sites that can be recognized by the bacteria, i.e. by the restriction enzymes expressed by all the bacteria.

In an eight aspect, the restriction sites are the restriction sites recognized by a population of bacteria, such as bacteria from the human microbiome for example, i.e. by the restriction enzyme expressed by all of the bacterial population.

A list of the restriction sites recognized by the restriction enzymes of a bacterial strain, a group of bacterial strains, a bacterial species, a group of bacterial species, or a bacterial genus of interest can be established by the man skilled in the art on the basis of restrictions sites databases such as REBASE. Alternatively, other databases well-known by the person skilled in the can be used such as RefSeq of NCBI (ncbi.nlm.nih.gov/refseq/, in particular Release 86); Enterobase (enterobase.warwick.ac.uk, in particular accessed 30 Jan. 2018); Genomes Online Database (gold.jgi.doe.gov/, in particular Gold Release v-6); and Sanger (ftb.sanger.ac.uk/pub/project/pathogens/)

In order to determine the frequency of each restriction enzyme in a group of bacteria of interest, two complementary approaches can be taken, both relying on REBASE, a comprehensive database of Restriction-Modification (R-M) systems (Roberts, R. et al., 2003, Nucleic Acids Research 31, 1805-1812). REBASE, identifies R-M genes and their cognate DNA recognition sites in a given bacterium by comparing the bacterial genome with a library of R-M system whose recognition sites have been validated experimentally. REBASE associates a new recognition site only if the two protein sequences are highly similar or identical (e.g., have 100% percentage identity). More recently, Single molecule real time sequencing (SMRT) allows the identification of the methylation pattern across genomes. Combined with the identification of R-M system, it permits the association of R-M systems with their recognition sites. With the increasing number of genomes and SMRT sequencing available, the number of characterized R-M systems is increasing exponentially.

A first approach may consist in extracting from REBASE all the type I S (including PacBIO data), type II R, type III R, R-M gene names and their associated sites. Thanks to the nomenclature of the genes (EcoRI stand for *Escherichia coli* strain RY13 enzyme I) (Roberts, R., et al, 2015, Nucleic Acids Res 43, D298-D299), the species and strains for most of these R-M can be identified and it is possible to deduce the most frequent site in each species. In particular the R-M present in at least 10% of the strains of the bacterial species of interest are selected.

The second approach rely on the sequencing of specific collections of strains of interest of a given bacterial species. Raw sequencing data can be assembled into contigs thanks to a genome assembler (spades) (Bankevich, A. et al. 2012, *J. Comput. Biol.* 19, 455-77). Then, contigs are annotated thanks to RASTK (Brettin, T. et al., 2015, *Sci Rep* 5, 8365) or prokka pipeline (Seemann, T., 2014, *Bioinformatics* 30, 2068-9). For each strain, all annotated proteins were blasted against each REBASE extracted list of R-M with a e-value of 1e-120 as a threshold. Only R-M systems with a percentage of identity equal or above 80% and present in at least 10% of the strains of the bacterial species of interest are selected. The 10% threshold can be adapted upon the selected frequency.

In a particular embodiment, the present invention concerns a vector, preferably a vector included in a delivery vehicle, which comprises no more than 100, 90, 80, 70, 60, 50, 40, 30, 20, 10, 9, 8, 7, 6, 5, 4, 3, 2, 1 restrictions site(s) from a list of restriction sites. Preferably, the vector, preferably a vector included in a delivery vehicle, doesn't comprise any restriction site from a list of restriction sites. Said list of restriction sites comprise at least 1 restriction site sequence. Preferably, said list of restriction sites comprises at least 2, 3, 4, 5, 6, 7, 8, 9, 10, 20, 30, 40, 50, 60, 70, 80, 90, 100, 200, 300, 400, 500, 600, 700, 800, 900, 1000 restriction site sequences. Preferably, said list of restriction sites comprises at least 1%, 10%, 20%, 30%, 40%, 50%, 60%, 70%, 80%, 90%, 95%, 99%, 100% of the known restriction sites. More preferably, said list of restriction sites comprises at least 1%, 10%, 20%, 30%, 40%, 50%, 60%, 70%, 80%, 90%, 95%, 99%, 100% of the restriction sites known to be recognized by the restriction enzymes of a given bacterial genus, group of species, species, group of strains, or strain of interest. In one embodiment, said list of restriction sites comprise the restriction sites of restriction enzymes which are frequently encoded in the group of the bacteria of interest. In a very specific embodiment, said list of restriction sites comprise the restriction sites of restriction enzymes which are present in at least 10% of bacteria from the group of bacteria of interest. In a specific embodiment, the list is one among the lists provided in Table 1 or 2 for each group of bacteria of interest.

Then, the present invention concerns a vector, preferably a vector included in a delivery vehicle, which comprises 0, 1 or 2 restrictions site(s) from a list of restriction sites, preferably the list of restriction sites comprising the restriction sites of restriction enzymes which are frequent in the group of the bacteria of interest, preferably present in at least 10% of bacteria from the group of bacteria of interest. In a specific embodiment, the list is one among the lists provided in Table 1 or 2 for each group of bacteria of interest. Preferably, the vector does not comprise any restriction site of the list provided in Table 1 or 2 for a particular group of bacteria of interest.

In a particular embodiment, the present invention concerns a vector, preferably a vector included in a delivery vehicle, which does not comprise one restriction site selected from the group consisting of the list of restriction sites comprising the restriction sites of restriction enzymes which are frequent in the group of the bacteria of interest, preferably present in at least 10% of bacteria from the group of bacteria of interest. For instance, the vector, preferably a vector included in a delivery vehicle, does not comprise 1, 2, 3, 4, 5, 6 or 7 restriction sites selected from the group consisting of the list of restriction sites, preferably the list of restriction sites comprising the restriction sites of restriction enzymes which are frequent in the group of the bacteria of interest, preferably present in at least 10% of bacteria from the group of bacteria of interest. In a particular embodiment, the vector, preferably a vector included in a delivery vehicle, comprises no restriction site of the list of restriction sites, preferably the list of restriction sites comprising the restriction sites of restriction enzymes which are frequent in the group of the bacteria of interest, preferably present in at least 10% of bacteria from the group of bacteria of interest. In a specific embodiment, the list is one among the lists provided in Table 1 or 2 for each group of bacteria of interest. Preferably, the vector does not comprise any restriction site of the list provided in Table 1 or 2 for a particular group of bacteria of interest.

In a particular embodiment, the vector does not comprise any restriction site of any restriction enzymes which are encoded in a group of bacteria of interest.

Preferably, the vector according to the invention is bacteriophage genome or a phagemid.

More preferably, the vector according to the invention is a bacteriophage or a packaged phagemid.

The man skilled in the art can establish such a list on the basis of databases such as REBASE. In a particular embodiment, said list of restriction sites comprises all the restriction enzymes sequences disclosed on the REBASE database. Alternatively, said list of restriction sites comprises all the restriction enzymes sequences disclosed on the REBASE database that are recognized by the restriction enzymes of a given bacterial genus, group of species, species, group of strains, or strain of interest.

Techniques for modifying the number of restriction sites in a vector are well know from the man skilled in the art. Specific databases, such as REBASE, can be used to identify the restriction sites and the corresponding restriction enzyme in a vector. Restriction sites can then be modified, for instance, one by one until the desired number or percentage of restriction sites is reached.

By modification of a restriction site is intended that the modified sequence of the restriction site present at least one nucleotide difference with its non-modified sequence and that the restriction enzyme cannot recognized the restriction site anymore.

Modification of a restriction site can be done by deletion of a part or of the totality of the restriction site or by nucleotide substitution of at least one nucleotide of the restriction site.

Preferably, restriction sites in non-coding region of the vector are modified first and restriction sites of coding regions of the vector are modified only if the desired number or percentage of restriction sites is not reached after that all the restriction sites in non-coding regions have been modified.

Optionally, deletion is only performed in non-coding region.

Substitutions in restriction sites are preferably neutral substitutions, in particular in coding regions. A codon usage table can be used to determinate the possible neutral substitutions.

When no neutral substitutions are available in a restriction site and no other restriction sites can be modified, nucleotide mutations leading to conservative amino acid mutations can be performed.

When a restriction site comprises a nucleotide of the "N" type, substitutions will occur in non-N nucleotides.

Preferably, substitutions are chosen so as to meet the codon usage of the bacteria.

The vector can be modified either by mutation, for instance by direct mutagenesis, or any suitable technique known by the person skilled in the art, or when the sequence has been designed, by nucleic acid synthesis (see for example Huges R A et al, 2017, Cold Spring Harb Perspect Biol, 9:a023812).

In particular, classical cloning techniques well known by the man skilled in the art can be used to modify restriction sites. These techniques include without limitation restriction enzyme cloning, gibson assembly, and inverse PCR.

For example, bacteriophages can be mutated by yeast-mediated cloning (see for example Joska T M et al, 2014, Journal of Microbiological Methods, 100: 46-51). Other mutation methods include without limitation Lambda Red-mediated insertions/deletions (see for example Murphy K C, 1998, J Bacteriol., 180(8): 2063-71), multiplex automated genome engineering (MAGE) (see for example Wang H H et al, 2009, Nature, 460(7257): 894-898), Cas9-mediated mutations (see for example Jiang Yu et al, 2015, Appl. Environ. Microbiol, 81(7): 2506-2514).

Bacteria of Interest

Preferably, the group of bacteria of interest consists of a group of n bacterial species, n being a positive integer comprised between 1 and about 100, preferably between 1 and about 50, more preferably between 1 and about 10, still preferably between 1 and about 5, even more preferably the group of bacteria of interest consists of a single bacterial species. Preferably, the bacterial species according to the invention are selected from a single genus.

More preferably, the group of bacteria of interest consists of a group of n bacterial strains, n being a positive integer comprised between 1, 2, 3, 4, 5, 6, 7, 8, 9 or 10 and about 1000, 10,000 or 100,000, preferably between 1, 2, 3, 4, 5, 6, 7, 8, 9 or 10 and about 500, more preferably between 1, 2, 3, 4, 5, 6, 7, 8, 9 or 10 and about 250, still preferably between 1, 2, 3, 4, 5, 6, 7, 8, 9 or 10 and about 100, even more preferably between 1, 2, 3, 4, 5, 6, 7, 8, 9 or 10 and about 50. In a most preferred embodiment, the group of bacteria of interest consists of a group of n bacterial strains, n being a positive integer comprised between 1 and about 30, preferably between 1 and about 20, more preferably between 1 and about 10, even more preferably between 1 and about 5. In a particular embodiment, the group of bacteria of interest consists of a single bacterial strain. Preferably, the bacterial strains according to the invention are selected from a single species.

The group of bacteria of interest may comprise the bacterial strains reported to cause a defined pathology.

The bacteria of interest according to the invention may be Eubacteria or Archaebacteria, preferably Eubacteria. The bacteria of interest according to the invention can be Gram-positive or Gram-negative Eubacteria.

In a preferred embodiment, the bacteria of interest according to the invention are virulent bacteria.

In another preferred embodiment, the bacteria of interest according to the invention are antibacterial resistance bacteria.

In yet another preferred embodiment, the bacteria of interest are different strains of the same species.

In another preferred embodiment, the bacteria of interest are different strains of different species.

In another preferred embodiment, the bacteria of interest are different strains of different species members of the human microbiome, particularly of the intestinal microbiome.

Examples of bacteria of interest according to the present invention include, without limitation, bacteria from *Yersinia* spp., *Escherichia* spp., *Klebsiella* spp., *Acinetobacter* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Vibrio* spp., *Bacillus* spp., *Erysipelothrix* spp., *Salmonella* spp., *Streptomyces* spp., *Streptococcus* spp., *Staphylococcus* spp., *Bacteroides* spp., *Prevotella* spp., *Clostridium* spp., *Bifidobacterium* spp., *Clostridium* spp., *Brevibacterium* spp., *Lactococcus* spp., *Leuconostoc* spp.,

*Actinobacillus* spp., *Selnomonas* spp., *Shigella* spp., *Zymonas* spp., *Mycoplasma* spp., *Treponema* spp., *Leuconostoc* spp., *Corynebacterium* spp., *Enterococcus* spp., *Enterobacter* spp., *Pyrococcus* spp., *Serratia* spp., *Morganella* spp., *Parvimonas* spp., *Fusobacterium* spp., *Actinomyces* spp., *Porphyromonas* spp., *Micrococcus* spp., *Bartonella* spp., *Borrelia* spp., *Campylobacter* spp., *Chlamydophilia* spp., *Ehrlichia* spp., *Haemophilus* spp., *Leptospira* spp., *Listeria* spp., *Mycoplasma* spp., *Nocardia* spp., *Rickettsia* spp., *Ureaplasma* spp., *Cutibacterium* (formerly *Propionibacterium*) spp., *Lactobacillus* spp., or a mixture thereof.

Preferably, the bacteria of interest according to the present invention are selected from the group consisting of *Yersinia* spp., *Escherichia* spp., *Klebsiella* spp., *Acinetobacter* spp., *Pseudomonas* spp., *Helicobacter* spp., *Vibrio* spp, *Salmonella* spp., *Streptococcus* spp., *Staphylococcus* spp., *Bacteroides* spp., *Clostridium* spp., *Shigella* spp., *Enterococcus* spp., *Enterobacter* spp., and *Listeria* spp., More preferably, the bacteria of interest according to the present invention are selected from *Escherichia* spp.

In a preferred embodiment, the bacteria of interest according to the invention are selected from the group consisting of *Bacteroides thetaiotaomicron, Bacteroides fragilis, Bacteroides distasonis, Bacteroides vulgatus, Clostridium leptum, Clostridium coccoides, Staphylococcus aureus, Bacillus subtilis, Clostridium butyricum, Brevibacterium lactofermentum, Streptococcus agalactiae, Lactococcus lactis, Leuconostoc lactis, Actinobacillus actinobycetemcomitans, cyanobacteria, Escherichia coli, Helicobacter pylori, Selnomonas ruminatium, Shigella sonnei, Zymomonas mobilis, Mycoplasma mycoides, Treponema denticola, Bacillus thuringiensis, Staphilococcus lugdunensis, Leuconostoc oenos, Corynebacterium xerosis, Lactobacillus plantarum, Lactobacillus rhamnosus, Lactobacillus casei, Lactobacillus acidophilus, Enterococcus faecalis, Bacillus coagulans, Bacillus cereus, Bacillus popillae, Synechocystis* strain PCC6803, *Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Streptomyces phaechromogenes, Streptomyces ghanaenis, Klebsiella pneumoniae, Enterobacter cloacae, Enterobacter aerogenes, Serratia marcescens, Morganella morganii, Citrobacter freundii, Pseudomonas aerigunosa, Parvimonas micra, Prevotella intermedia, Fusobacterium nucleatum, Prevotella nigrescens, Actinomyces israelii, Porphyromonas endodontalis, Porphyromonas gingivalis Micrococcus luteus, Bacillus megaterium, Aeromonas hydrophila, Aeromonas caviae, Bacillus anthracis, Bartonella henselae, Bartonella Quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Campylobacter coli, Campylobacter fetus, Chlamydia pneumoniae, Chlamydia trachomatis, Chlamydophila psittaci, Clostridium botulinum, Clostridium difficile, Clostridium perfringens, Clostridium tetani, Corynebacterium diphtheria, Cutibacterium acnes* (formerly *Propionibacterium acnes*), *Ehrlichia canis, Ehrlichia chaffeensis, Enterococcus faecium, Francisella tularensis, Haemophilus influenza, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumonia, Neisseria gonorrhoeae, Neisseria meningitides, Nocardia asteroids, Rickettsia rickettsia, Salmonella enteritidis, Salmonella typhi, Salmonella paratyphi, Salmonella typhimurium, Shigellaflexnerii, Shigella dysenteriae, Staphylococcus saprophyticus, Streptococcus pneumoniae, Streptococcus pyogenes, Streptococcus viridans, Treponema pallidum, Ureaplasma urealyticum, Vibrio cholera, Vibrio parahaemolyticus, Yersinia pestis, Yersinia enterocolitica, Yersinia pseudotuberculosis, Acinetobacter baumanii, Pseudomonas aeruginosa,* and a mixture thereof. Preferably, the bacteria of interest according to the invention are selected from the group consisting of *Escherichia coli, Enterococcus faecium, Staphylococcus aureus, Klebsiella pneumoniae, Acinetobacter baumanii, Pseudomonas aeruginosa, Enterobacter cloacae,* and *Enterobacter aerogenes,* and a mixture thereof. More preferably, the bacteria of interest according to the invention are selected from *Escherichia coli* strains. Other bacteria may also be selected.

In another preferred embodiment, the bacteria of interest according to the invention are antibacterial resistance bacteria, preferably selected from the group consisting of extended-spectrum beta-lactamase-producing (ESBL) *Escherichia coli,* ESBL *Klebsiella pneumoniae,* vancomycin-resistant *Enterococcus* (VRE), methicillin-resistant *Staphylococcus aureus* (MRSA), multidrug-resistant (MDR) *Acinetobacter baumannii,* MDR *Enterobacter* spp., Carpabenem resistance Enterobacteriaceae (CRE), Colisitin resistance *E. coli* and a combination thereof. Preferably, the bacteria of interest according to the invention are antibacterial resistance bacteria selected from the group consisting of extended-spectrum beta-lactamase-producing (ESBL) *Escherichia coli* strains.

The bacteria of interest can also be selected among Shiga-toxin-Producing *Escherichia coli* (STEC) and Verotoxin producing *Escherichia coli* (VTEC).

The bacteria of interest can also be selected among Enteropathogenic *E. coli* (EPEC), Enterohemorrhagic *E. coli* (EHEC), Enteroaggregative *E. coli* (EAEC), Enterotoxigenic *E. coli* (ETEC), Adherent and Invasive *E. coli* (AIEC), Uropathogenic *E. coli* (UPEC), In yet another embodiment, the bacterium of interest according to the invention is a bacterium of the microbiome of a given species, preferably a bacterium of the human microbiote.

In a particular embodiment, the bacteria of interest are selected from *Escherichia coli* strains and said restriction sites recognized by the restriction enzymes of *Escherichia coli* strains are CACNNNNNNNCTGG (SEQ ID NO: 1), AACNNNNNNGTGC (SEQ ID NO: 2), CACNNNNGTAY (SEQ ID NO: 3), AACNNNNCTTT (SEQ ID NO: 4), CCANNNNNNNCTTC (SEQ ID NO: 5), TACNNNNNNNRTRTC (SEQ ID NO: 6), GAGNNNNNNNGTCA (SEQ ID NO: 7), TGANNNNNNNTGCT (SEQ ID NO: 8), AGCANNNNNNTGA (SEQ ID NO: 9), TGANNNNNNCTTC (SEQ ID NO: 10), GAGNNNNNGTTY (SEQ ID NO: 11), GATGNNNNNNTAC (SEQ ID NO: 12), GAANNNNNNRTCG (SEQ ID NO: 13), RTCANNNNNNCTC (SEQ ID NO: 14), GNAGNNNNRTDCA (SEQ ID NO: 15), GAANNNNNNNRTCG (SEQ ID NO: 16), GGANNNNNNNATGC (SEQ ID NO: 17), GAGNNNNTCC (SEQ ID NO: 18), CACNNNNNNNGTTG (SEQ ID NO: 19), YTCANNNNNNGTTY (SEQ ID NO: 20), GATGNNNNNCTG (SEQ ID NO: 21), CCAYNNNNNGTTY (SEQ ID NO: 22), RTCANNNNNNNNGTGG (SEQ ID NO: 23), GAANNNNNNNTAAA (SEQ ID NO: 24), TCANNNNNNNRTTC (SEQ ID NO: 25), GACNNNNNGTC (SEQ ID NO: 26), TTCANNNNNNNCTGG (SEQ ID NO: 27), TTANNNNNNNIGTCY (SEQ ID NO: 28), CCANNNNNNNRTGC (SEQ ID NO: 29), CCANINNNNNNNTGAA (SEQ ID NO: 30), GAGNNNNNNATGC (SEQ ID NO: 31), CAGNNNNNNCGT (SEQ ID NO: 32), GATGNNNNNGGC (SEQ ID NO: 33), GAAABCC (SEQ ID NO: 34), CCWGG (SEQ ID NO: 35), GGTCTC (SEQ ID NO: 36), CTGCAG (SEQ ID NO: 37), GCCGGC (SEQ ID NO: 38), RGGNCCY (SEQ ID NO: 39), GTCGAC (SEQ ID NO: 40), GCGCGC (SEQ ID NO: 41), RCCGGY (SEQ ID NO: 42), CCNGG (SEQ ID NO: 43), AAGCTT (SEQ ID NO: 44), CANCATC (SEQ ID NO: 45), GRCGYC (SEQ ID NO: 46), CYCGRG (SEQ ID NO: 47), GCNGC (SEQ ID NO: 48), YGGCCR (SEQ ID NO: 49), CCGCGG (SEQ ID NO: 50), GRGCYC (SEQ ID NO: 51), CTGAAG (SEQ ID NO: 52), GGWCC (SEQ ID NO: 53), TGGCCA (SEQ ID NO: 54), CCWWGG (SEQ ID NO: 55), GGNCC (SEQ ID NO: 56), GAGCTC (SEQ ID NO: 57), GGTACC (SEQ ID NO: 58), GGCGCC (SEQ ID NO: 59), ACCYAC (SEQ ID NO: 60), GAATTC (SEQ ID NO: 61), GATATC (SEQ ID NO: 62), CCTNAGG (SEQ ID NO: 63), GGTNACC (SEQ ID NO: 64), ATGCAT (SEQ ID NO: 65), GGYRCC (SEQ ID NO: 66), AGGCCT (SEQ ID NO: 67), CTCAAT (SEQ ID NO: 68), GCWGC (SEQ ID NO: 69), TCGCGA (SEQ ID NO: 70), CCTNNNNNAGG (SEQ ID NO: 71), ACCACC (SEQ ID NO: 72), CACAG (SEQ ID NO: 73), GAACC (SEQ ID NO: 74), GAGAC (SEQ ID NO: 75), CAGCAG (SEQ ID NO: 76), AGACC (SEQ ID NO: 77), and CCGAG (SEQ ID NO: 78).

In a particular embodiment, the restriction enzymes of *Escherichia coli* are the following type I Restriction enzymes: CACNNNNNNNCTGG (SEQ ID NO: 1), AACNNNNNNNGTGC (SEQ ID NO: 2), CACNNNNNGTAY (SEQ ID NO: 3), AACNNNNCTTT (SEQ ID NO: 4), CCANNNNNNNCTTC (SEQ ID NO: 5), TACNNNNNNNNRTRTC (SEQ ID NO: 6), GAG-NNNNNNNGTCA (SEQ ID NO: 7), TGANNNNNNNNTGCT (SEQ ID NO: 8), AGCANNNNNNTGA (SEQ ID NO: 9), TGANNNNNNCTTC (SEQ ID NO: 10), GAG-NNNNNGTTY (SEQ ID NO: 11), GATGNNNNNNNTAC (SEQ ID NO: 12), GAANNNNNNNRTCG (SEQ ID NO: 13), RTCANNNNNNCTC (SEQ ID NO: 14), GNAG-NNNNRTDCA (SEQ ID NO: 15), GAANNNNNNNTCG (SEQ ID NO: 16), GGANNNNNNNATGC (SEQ ID NO: 17), GAGNNNNNTCC (SEQ ID NO: 18), CACNNNNNNNGTTG (SEQ ID NO: 19), YTCANNNNNNGTTY (SEQ ID NO: 20), GATGNNNNNCTG (SEQ ID NO: 21), CCAYNNNNNGTTY (SEQ ID NO: 22), RTCANNNNNNNGTGG (SEQ ID NO: 23), GAANNNNNNNTAAA (SEQ ID NO: 24), TCANNNNNNRTTC (SEQ ID NO: 25), GACNNNNNNNGTC (SEQ ID NO: 26), TTCANNNNNNNNCTGG (SEQ ID NO: 27), TTANNNNNNNGTCY (SEQ ID NO: 28), CCANNNNNNNRTGC (SEQ ID NO: 29), CCANNNNNNNNTGAA (SEQ ID NO: 30), GAG-NNNNNNNATGC (SEQ ID NO: 31), CAGNNNNNNCGT (SEQ ID NO: 32), GATGNNNNNGGC (SEQ ID NO: 33).

In another particular embodiment, the restriction enzymes of *Escherichia coli* are the following type II Restriction enzymes: GAAABCC (SEQ ID NO: 34), CCWGG (SEQ ID NO: 35), GGTCTC (SEQ ID NO: 36), CTGCAG (SEQ ID NO: 37), GCCGGC (SEQ ID NO: 38), RGGNCCY (SEQ ID NO: 39), GTCGAC (SEQ ID NO: 40), GCGCGC (SEQ ID NO: 41), RCCGGY (SEQ ID NO: 42), CCNGG (SEQ ID NO: 43), AAGCTT (SEQ ID NO: 44), CANCATC (SEQ ID NO: 45), GRCGYC (SEQ ID NO: 46), CYCGRG (SEQ ID NO: 47), GCNGC (SEQ ID NO: 48), YGGCCR (SEQ ID NO: 49), CCGCGG (SEQ ID NO: 50), GRGCYC (SEQ ID NO: 51), CTGAAG (SEQ ID NO: 52), GGWCC (SEQ ID NO: 53), TGGCCA (SEQ ID NO: 54), CCWWGG (SEQ ID NO: 55), GGNCC (SEQ ID NO: 56), GAGCTC (SEQ ID NO: 57), GGTACC (SEQ ID NO: 58), GGCGCC (SEQ ID NO: 59), ACCYAC (SEQ ID NO: 60), GAATTC (SEQ ID NO: 61), GATATC (SEQ ID NO: 62), CCTNAGG (SEQ ID NO: 63), GGTNACC (SEQ ID NO: 64), ATGCAT (SEQ ID NO: 65), GGYRCC (SEQ ID NO: 66), AGGCCT (SEQ ID NO: 67), CTCAAT (SEQ ID NO: 68), GCWGC (SEQ ID NO: 69), TCGCGA (SEQ ID NO: 70), CCTNNNNNAGG (SEQ ID NO: 71), ACCACC (SEQ ID NO: 72).

In yet another particular embodiment, the restriction enzymes of *Escherichia coli* are the following type III Restriction enzymes: CACAG (SEQ ID NO: 73), GAACC (SEQ ID NO: 74), GAGAC (SEQ ID NO: 75), CAGCAG (SEQ ID NO: 76), AGACC (SEQ ID NO: 77), and CCGAG (SEQ ID NO: 78).

In another particular embodiment, the restriction enzymes of the bacteria of interest are selected from the restriction enzymes of type I and/or the restriction enzyme of type II and/or the restriction enzyme of type III and/or the restriction enzymes of type IV. Preferably, the restriction enzymes of the bacteria of interest are selected from the restriction enzymes of type I, the restriction enzyme of type II, the restriction enzyme of type III, and the restriction enzymes of type IV.

In a particular embodiment, a list A of restriction sites of restriction enzymes which are frequently encoded by a group of bacteria of interest from *E. coli* comprises:
 CACNNNNNNNCTGG (SEQ ID NO: 1) (present in 24.5% of *E. coli* referenced strains in REBASE);
 AACNNNNNNNGTGC (SEQ ID NO: 2) (present in 18% of *E. coli* referenced strains in REBASE);
 AACNNNNCTTT ((SEQ ID NO: 4) (present in 12% of *E. coli* referenced strains in REBASE);
 CACNNNNGTAY (SEQ ID NO: 3) (present in 11% of *E. coli* referenced strains in REBASE);
 GGTCTC (SEQ ID NO: 36) (present in 18% of *E. coli* referenced strains in REBASE);
 CTGCAG (SEQ ID NO: 37) (present in 18% of *E. coli* referenced strains in REBASE) and,
 GAAABCC (SEQ ID NO: 34) (present in 26% of *E. coli* referenced strains in REBASE).

In one embodiment, the present invention relates to a vector, preferably a vector included in a delivery vehicle, designed for a group of bacteria of interest belonging to the species *E. coli* which does not comprise 1, 2, 3, 4, 5, 6 or 7 restriction sites selected from the group consisting of this list A of restriction sites. In a particular embodiment, the present invention relates to a vector, preferably a vector included in a delivery vehicle, designed for a group of bacteria of interest belonging to the species *E. coli* which does not comprise any of restriction sites CACNNNNNNCTGG (SEQ ID NO: 1), CTGCAG (SEQ ID NO: 37) and GAAABCC (SEQ ID NO: 34). Preferably, it relates to a vector, preferably a vector included in a delivery vehicle, designed for a group of bacteria of interest belonging to the species *E. coli* which does not comprise any restriction site of this list A of restriction sites.

In another particular embodiment, a list B of restriction sites of restriction enzymes which are frequently encoded by a group of bacteria of interest from *E. coli* STEC or a subgroup of this species comprises:

TACNNNNNNNNRTRTC (SEQ ID NO: 6) (present in 24% of a STEC strain collection);
CACNNNNNNNCTGG (SEQ ID NO: 1) (present in 24% of a STEC strain collection);
CTGCAG (SEQ ID NO: 37) (present in 27% of a STEC strain collection)
GAAABCC (SEQ ID NO: 34) (present in 20% of a STEC strain collection); and
GATCAG (SEQ ID NO: 79) (present in 15% of a STEC strain collection).

In one embodiment, the present invention relates to a vector, preferably a vector included in a delivery vehicle, designed for a group of bacteria of interest belonging to the species *E. coli* STEC which does not comprise 1, 2, 3, 4, or 5 restriction sites selected from the group consisting of this list B of restriction sites. In a particular embodiment, the present invention relates to a vector, preferably a vector included in a delivery vehicle, designed for a group of bacteria of interest belonging to the species *E. coli* STEC which does not comprise any of restriction sites CACNNNNNNNCTGG (SEQ ID NO: 1), CTGCAG (SEQ ID NO: 37) and GAAABCC (SEQ ID NO: 34). Preferably, it relates to a vector, preferably a vector included in a delivery vehicle, designed for a group of bacteria of interest belonging to the species *E. coli* STEC which does not comprise any restriction site of this list B of restriction sites.

TABLE 1

List of frequent Restriction sites for each group of bacteria on interest

| List A Restriction site | Group of bacteria: *E coli* SEQ ID NO | |
|---|---|---|
| CACNNNNNNNCTGG | 1 | |
| AACNNNNNNGTGC | 2 | |
| AACNNNNC TABLE 1 -continued List of frequent Restriction sites for each group of bacteria on interest

GCSGC

CCGG

CCACC                                       TYPEIII

AGAAA                                         TYPEIII

| List D Restriction site | Group of bacteria: *Neisseria meningitides* SEQ ID NO |
|---|---|

GGNNCC

GCGCGC

CCGG

RCCGGY

CCTTC

CCAGA

GACGC

ACACC                                       TYPEIII

| List E Restriction site | Group of bacteria: *Salmonella enteritidis* SEQ ID NO |
|---|---|
| GGTANNNNNNTCG | 84 |
| GAGNNNNNNRTAYG | 85 |
| CCCNNNNNNRTAG | 86 |
| GGYANNNNNNTCG | 87 |
| CCANNNNNNNNNTGAG | 88 |

GATCAG

GGWCC

CGGCCG

CAGAG                                       TYPEIII

| List F Restriction site | Group of bacteria: *Streptococcus pneumoniae* SEQ ID NO |
|---|---|

TCTAGA

| List G Restriction site | Group of bacteria: *Streptococcus pyogenes* SEQ ID NO |
|---|---|
| GCANNNNNNTTAA | 89 |
| CRAANNNNNNNTGC | 90 |
| GCANNNNNNRTTG | 91 |

| List H Restriction site | Group of bacteria: *Vibrio cholera* SEQ ID NO |
|---|---|
| AAGNNNNNNCATC | 92 |

| List I Restriction site | Group of bacteria: *Haemophilus influenza* SEQ ID NO |
|---|---|

RGCGCY

CGCG

AAGCTT

GCGC

TABLE 1 -continued

List of frequent Restriction sites for each group of bacteria on interest

GTYRAC

GTCGAC

| List J Restriction site | Group of bacteria: *Klebsiella pneumoniae* SEQ ID NO |
|---|---|
| CAGNNNNNNCGT | 93 |
| GAAYNNNNNNNCTGG | 94 |
| CGANNNNNNNNTGCC | 95 |
| ACGNNNNNGTTG | 96 |
| CGCATC | TYPEIII |

| List K Restriction site | Group of bacteria: *Pseudomonas aerigunosa* SEQ ID NO |
|---|---|
| CYYANNNNNNCTTC | 97 |
| CACNNNNNNNRTGT | 98 |
| CCCANNNNNNTCG | 99 |
| GTCGAC | |
| CTCGAG | |
| CTGCAG | 37 |
| GGCGCC | |

| List L Restriction site | Group of bacteria: *Staphylococcus aureus* SEQ ID NO |
|---|---|
| AGGNNNNNGAT | 100 |
| CCAYNNNNNNTGT | 101 |
| CCAYNNNNNNGTA | 102 |
| CCNGG | |
| GCNGC | |
| GGNCC | |

| List M Restriction site | Group of bacteria: *Vibrio cholera* SEQ ID NO |
|---|---|
| AAGNNNNNNCATC | 103 |

| List N Restriction site | Group of bacteria: *Brucella suis* SEQ ID NO |
|---|---|
| CTCGAG | |
| GACGAG | |

| List O Restriction site | Group of bacteria: *Mycobacterium tuberculosis* SEQ ID NO |
|---|---|
| GATNNNNRTAC | 104 |
| CACGCAG | |

| List P Restriction site | Group of bacteria: *Enterobacter cloacae* SEQ ID NO |
|---|---|
| GTCGAC | |

TABLE 1 -continued

List of frequent Restriction sites for each group of bacteria on interest

| List Q Restriction site | Group of bacteria: *Bacillus cereus* SEQ ID NO |
|---|---|
| GCNGC | |
| GCSGC | |
| ACGGC | |
| CACAG | TYPEIII |

| List R Restriction site | Group of bacteria: *Corynebacterium diphtheria* SEQ ID NO |
|---|---|
| GCGGAG | |

| List S Restriction site | Group of bacteria: *Campylobacter jejuni* SEQ ID NO |
|---|---|
| GCANNNNNRTTA | 105 |
| RAACNNNNNNRTTA | 106 |
| AGTNNNNNNRTTG | 107 |
| GKAAYG | |
| GAGNNNNNGT | 108 |

| List T Restriction site | Group of bacteria: *Listeria monocytogenes* SEQ ID NO |
|---|---|
| GAAYNNNNNGTC | 109 |
| GANNNNNNTGCG | 110 |
| TTAGNNNNNNTTC | 111 |
| GATGNNNNTGT | 112 |
| TAGRAG | |
| GTATCC | |
| GTCGAC | |

| List U Restriction site | Group of bacteria: *Campylobacter coli* SEQ ID NO |
|---|---|
| GAGNNNNNRTG | 113 |

| List V Restriction site | Group of bacteria: *Bacillus thuringiensis* SEQ ID NO |
|---|---|
| GGWCC | |
| ACGGC | |

| List W Restriction site | Group of bacteria: *Yersinia enterocolitica* SEQ ID NO |
|---|---|
| GGCGCC | |
| GCGCGC | |

| List X Restriction site | Group of bacteria: *Helicobacter pylori* SEQ ID NO |
|---|---|
| CCGG | |
| GTNNAC | |
| GTAC | |
| CATG | |
| TCNNGA | |

TABLE 1 -continued

List of frequent Restriction sites for each group of bacteria on interest

TGCA

GANTC

ACNGT

ACGT

CCATC

CCTC

CTNAG

GAAGA

GTSAC

CCNNGG

GAATTC

GGCC

TCNGA

CCTTC

CTGCAG                                   TYPEIII

TCAG                                     TYPEIII

TABLE 2

Additional List of frequent Restriction sites for each group of bacteria on interest

| List D Restriction site | Group of bacteria: *Neisseria meningitides* SEQ ID NO |
|---|---|
| CACNNNNNTAC | 114 |
| CCTTC | |
| GGNNCC | |
| GCGCGC | |
| CCGG | |
| RCCGGY | |
| CCAGA | |
| GACGC | |
| ACACC | TYPEIII |

| List F Restriction site | Group of bacteria: *Streptococcus pneumoniae* SEQ ID NO |
|---|---|
| CRAANNNNNNNCTT | 115 |
| TGANNNNNNNTATC | 116 |
| CRAANNNNNNNNNTTC | 117 |
| CRAANNNNNNNNCTG | 118 |
| CACNNNNNNNCTG | 119 |
| CACNNNNNNNNTTC | 120 |
| CACNNNNNNNCTT | 121 |

TABLE 2 -continued

Additional List of frequent Restriction sites for each group of bacteria on interest

| | |
|---|---|
| TCTAGA | |
| List G Restriction site | Group of bacteria: *Streptococcus pyogenes* SEQ ID NO |
| GCANNNNNNTTAA | 89 |
| CRAANNNNNNNTGC | 90 |
| GCANNNNNNNRTTG | 91 |
| CCNGG | |
| List H Restriction site | Group of bacteria: *Vibrio cholera* SEQ ID NO |
| AAGNNNNNNCATC | 92 |
| CTGCAG | |
| TCCGGA | |
| GGCGCC | |
| CTCGAG | |
| GGNCC | |
| List I Restriction site | Group of bacteria: *Haemophilus influenza* SEQ ID NO |
| TTTANNNNNNNGTT | 122 |
| CTANNNNNGTTY | 123 |
| GAYNNNNNNGTT | 124 |
| RGCGCY | |
| CGCG | |
| AAGCTT | |
| GCGC | |
| GTYRAC | |
| GTCGAC | |
| CGAG | TYPEIII |
| AGAAA | TYPEIII |
| ACAGC | TYPEIII |
| CGAAT | TYPEIII |
| List K Restriction site | Group of bacteria: *Pseudomonas aerigunosa* SEQ ID NO |
| CYYANNNNNNCTTC | 97 |
| CACNNNNNNNRTGT | 98 |
| CCCANNNNNNTCG | 99 |
| CCCANNNNNCTG | 125 |
| TCCANNNNNNCGT | 126 |
| ACGNNNNNRTGT | 127 |
| ATGNNNNNNCCTC | 128 |
| TCABNNNNNNNTCCA | 129 |

TABLE 2 -continued

Additional List of frequent Restriction sites for each group of bacteria on interest

| Restriction site | SEQ ID NO | |
|---|---|---|
| GACNNNNNNGATC | 130 | |
| AGGNNNNNTTCA | 131 | |
| GTCGAC | | |
| CTCGAG | | |
| CTGCAG | | |
| GGCGCC | | |
| ACGACC | | TYPEIII |
| GCCCAG | | TYPEIII |

| List L Restriction site | Group of bacteria: *Staphylococcus aureus* SEQ ID NO | |
|---|---|---|
| AGGNNNNNGAT | 100 | |
| CCAYNNNNNNTGT | 101 | |
| CCAYNNNNNNGTA | 102 | |
| CCNGG | | |
| GCNGC | | |
| GGNCC | | |
| GAAGNNNNNTAC | 132 | |
| CCAYNNNNNTTAA | 133 | |
| GCTGA | | TYPEIII |

| List N Restriction site | Group of bacteria: *Brucella suis* SEQ ID NO | |
|---|---|---|
| CNCANNNNNNNRTGT | 134 | |
| CCANNNNNNRTTNC | 135 | |
| CTCGAG | | |
| GACGAG | | |

| List O Restriction site | Group of bacteria: *Mycobacterium tuberculosis* SEQ ID NO | |
|---|---|---|
| GATNNNNRTAC | 104 | |
| CACGCAG | | |
| ACAYNNNNNNNTTGG | 136 | |

| List P Restriction site | Group of bacteria: *Enterobacter cloacae* SEQ ID NO | |
|---|---|---|
| GATANNNNNNNTGC | 137 | |
| GCCNNNNNGTTG | 138 | |
| CATCNNNNNNTCC | 139 | |
| RTCANNNNNNNNN-TRGG | 140 | |
| GTCGAC | | |
| ACGAAG | | TYPEIII |

TABLE 2 -continued

Additional List of frequent Restriction sites for each group of bacteria on interest

| List Q Restriction site | Group of bacteria: SEQ ID NO | *Bacillus cereus* Present in x % |
|---|---|---|
| ATTCNNNNCTG | 141 | |
| TAAGNNNNNNNTGG | 142 | |
| GAGNNNNNNRTGC | 143 | |
| CCCNNNNNCTC | 144 | |
| AGCNNNNNNTACA | 145 | |
| CCANNNNNNNCTTA | 146 | |
| GCAYNNNNNNCTC | 147 | |
| GCNGC | | |
| GCSGC | | |
| GCWGC | | |
| ACGGC | | |
| CTCGAG | | |
| CACAG | | TYPEIII |

| List R Restriction site | Group of bacteria: SEQ ID NO | *Corynebacterium diphtheria* |
|---|---|---|
| CANNNNNNNTAAAG | 148 | |
| TAGNNNNNRTGAA | 149 | |
| ATTYNNNNNCTTC | 150 | |
| AYGNNNNNNNCTG | 151 | |
| GAANNNNNNRTGC | 152 | |
| GCGGAG | | |

| List S Restriction site | Group of bacteria: SEQ ID NO | *Campylobacter jejuni* |
|---|---|---|
| GCANNNNNRTTA | 105 | |
| RAACNNNNNNNRTTA | 106 | |
| AGTNNNNNNNRTTG | 107 | |
| CATG | | |
| GKAAYG | | |
| GAGNNNNNGT | 108 | |

| List T Restriction site | Group of bacteria: SEQ ID NO | *Listeria monocytogenes* |
|---|---|---|
| GAAYNNNNNGTC | 109 | |
| GANNNNNNTGCG | 110 | |
| TACBNNNNNNNGTNG | 153 | |
| TTAGNNNNNNNTTC | 112 | |
| GATGNNNNTGT | 154 | |
| GACNNNNNGGT | 155 | |
| TAGRAG | | |

TABLE 2 -continued

| Additional List of frequent Restriction sites for each group of bacteria on interest | | |
|---|---|---|
| GTATCC | | |
| GTCGAC | | |
| ACANNNNCATC | | |
| List V Restriction site | Group of bacteria: SEQ ID NO | *Bacillus thuringiensis* |
| GGANNNNNNNRTGGC | 156 | |
| GGWCC | | |
| ACGGC | | |
| GCNGC | | |
| GGWCC | | |
| ACGGC | | |
| GCNGC | | |
| CACAG | | TYPEIII |
| List W Restriction site | Group of bacteria: SEQ ID NO | *Yersinia enterocolitica* |
| GGCGCC | | |
| GCGCGC | | |
| CCGAG | | TYPEIII |
| List X Restriction site | Group of bacteria: SEQ ID NO | *Helicobacter pylori* |
| CTANNNNNNNNTGT | 157 | |
| ACANNNNNNNNTAG | 158 | |
| CCANNNNNNTC | 159 | |
| GANNNNNNNTAYG | 160 | |
| RTAYNNNNNRTAY | 161 | |
| AAGNNNNNCTT | 162 | |
| AAGNNNNNNTAAAG | 163 | |
| CCANNNNNNTTT | 164 | |
| CCGG | | |
| GTNNAC | | |
| CATG | | |
| GTAC | | |
| TCNNGA | | |
| GANTC | | |
| TGCA | | |
| ACNGT | | |
| ACGT | | |
| CCATC | | |
| CCTC | | |
| CTNAG | | |

TABLE 2 -continued

Additional List of frequent Restriction sites for each group of bacteria on interest

GAAGA

CCNNGG

GTSAC

GAATTC

GGCC

TCNGA

CCTTC

CTGCAG                                      TYPEIII

TCAG                                        TYPEIII

| List Z<br>Restriction site | Group of bacteria:<br>SEQ ID NO | *Bacteroides fragilis* |
|---|---|---|
| CAGNNNNNGAT | 165 | |
| ATGCAT | | |

| List AA<br>Restriction site | Group of bacteria:<br>SEQ ID NO | *Clostridium butyricum* |
|---|---|---|
| AAGNNNNNCTCC | 166 | |
| GCNGC | | |
| GCTNAGC | | |

| List AB<br>Restriction site | Group of bacteria:<br>SEQ ID NO | *Streptococcus agalactiae* |
|---|---|---|
| GAGNNNNRTAA | 167 | |
| GGNCC | | |
| GGCC | | |
| CCGG | | |

| List AC<br>Restriction site | Group of bacteria:<br>SEQ ID NO | *Leuconostoc lactis* |
|---|---|---|
| CAANNNNNNNTAYG | | |
| TNAGCC | | |
| CCNGG | | |
| GCNGC | | |
| CCCGC | | |

| List AD<br>Restriction site | Group of bacteria:<br>SEQ ID NO | *Shigella sonnei* |
|---|---|---|
| GGANNNNNCTTT | 168 | |
| TTANNNNNNGTCY | 169 | |
| CTGCAG | | |
| CCNGG | | |
| GACGTC | | |
| GAATTC | | |
| GTCGAC | | |

TABLE 2 -continued

Additional List of frequent Restriction sites for each group of bacteria on interest

| List AE Restriction site | Group of bacteria: *Zymomonas mobilis* SEQ ID NO |
|---|---|
| GAAGNNNNNNNTCC | 170 |
| CAGNNNNCTG | 171 |
| ACANNNNNNRTGG | 172 |
| GATATC | |

| List AF Restriction site | Group of bacteria: *Treponema denticola* SEQ ID NO |
|---|---|
| GCAYNNNNNNCATC | 173 |

| List AG Restriction site | Group of bacteria: *Lactobacillus plantarum* SEQ ID NO |
|---|---|
| ATAYNNNNNCTAY | 174 |
| GAAYNNNNNRTAC | 175 |
| GGNCC | |
| CTCTTC | |
| GCATC | |
| GCSGC | |
| CGRYCG | |

| List AH Restriction site | Group of bacteria: *Enterococcus faecium* SEQ ID NO |
|---|---|
| CCANNNNNNTTGA | 176 |
| GGANNNNNNRTAA | 177 |
| CCGG | |
| CCVVWGG | |
| GCWGC | |

| List AI Restriction site | Group of bacteria: *Bacillus liquefaciens* SEQ ID NO |
|---|---|
| GAYNNNNNRTC | 178 |
| CGGANNNNNNTTC | 179 |
| ATCGAT | |
| GCWGC | |
| GCNGC | |
| GCGCGC | |
| GGATC | |
| GGGAC | |

| List AJ Restriction site | Group of bacteria: *Staphylococcus epidermidis* SEQ ID NO |
|---|---|
| ACANNNNNGTG | 180 |
| GTANNNNNNNCTC | 181 |
| GCANNNNNNTTAA | 182 |
| GGTGA | |

TABLE 2 -continued

Additional List of frequent Restriction sites for each group of bacteria on interest

CCTC

| List AK Restriction site | Group of bacteria: *Serratia marcescens* SEQ ID NO |
|---|---|
| ACGNNNNNGTTG | 183 |
| AAGNNNNNGTTC | 184 |
| CAYNNNNNNTCA | 185 |
| CAAHNNNNNNCTTC | 186 |

GCNGC

CTGCAG

CCCGGG

GCCGGC

CCGCGG

CAGAG                          TYPEIII

| List AL Restriction site | Group of bacteria: *Citrobacter freundii* SEQ ID NO |
|---|---|
| GCANNNNNNNNGTGG | 187 |
| TCAGNNNNNNTGC | 188 |
| CAACNNNNNCTT | 189 |
| GAAYNNNNNNNRTDCC | 190 |

CGATCG

| List AM Restriction site | Group of bacteria: *Parvimonas micra* SEQ ID NO |
|---|---|
| CGAANNNNNTGA | 191 |

GGCC

GCGATG

GTCGAC

CCGG

GCNGC

| List AN Restriction site | Group of bacteria: *Prevotella intermedia* SEQ ID NO |
|---|---|
| GACNNNNNNCTGG | 192 |
| TGANNNNNNNTGGG | 193 |
| GAGNNNNNNTTA | 194 |
| GAGNNNNNNTGG | 195 |
| GNNGANNNNNNNTGGG | 196 |
| TAAKNNNNGTC | 197 |
| CGCANNNNNCTG | 198 |
| CCANNNNNNNTGGG | 199 |
| AGYNNNNNNCTTC | 200 |

GGATG

TABLE 2 -continued

Additional List of frequent Restriction sites for each group of bacteria on interest

GCCGGC

| List AO Restriction site | Group of bacteria: *Brucella melitensis* SEQ ID NO |
|---|---|
| CCANNNNNNNCTC | 201 |
| CCANNNNNNRTTNC | 202 |
| GCWGC | |
| TGATCA | |
| CACAG | TYPEIII |

| List AP Restriction site | Group of bacteria: *Aeromonas caviae* SEQ ID NO |
|---|---|
| RGAANNNNNNNNRTGA | 203 |
| CTGCAG | |
| CRRTAAG | |
| CCGG | |
| GTCGAC | |
| GCYYGAC | |

| List AQ Restriction site | Group of bacteria: *Clostridium botulinum* SEQ ID NO |
|---|---|
| AGTNNNNNNNRTGC | 204 |
| GHTANNNNNNNTADC | 205 |
| GYAYNNNNNCTTG | 206 |
| TAGNNNNNNCTTGY | 207 |
| CCAYNNNNNGCT | 208 |
| GRCGYC | |
| GCWGC | |
| GCSGC | |
| CCGG | |
| GCNGC | |
| CTANNNNNNRTGAA | 209 |

| List AR Restriction site | Group of bacteria: *Clostridium perfringens* SEQ ID NO |
|---|---|
| TTTAYNNNNNNGTG | 210 |
| TAAYNNNNNNNRTTG | 211 |
| GCNGC | |
| GGWCC | |
| GTCTC | |
| GGCC | |
| ACGGC | |
| VGACAT | TYPEIII |

TABLE 2 -continued

Additional List of frequent Restriction sites for each group of bacteria on interest

| List AS Restriction site | Group of bacteria: *Enterococcus faecium* SEQ ID NO |
|---|---|
| CCANNNNNNTTGA | 212 |
| GGANNNNNNRTAA | 213 |
| CCGG | |
| CCVVWGG | |
| GCWGC | |

| List AT Restriction site | Group of bacteria: *Mycoplasma pneumonia* SEQ ID NO |
|---|---|
| GANNNNNNNTAY | 214 |

| List AU Restriction site | Group of bacteria: *Salmonella typhimurium* SEQ ID NO | |
|---|---|---|
| GAGNNNNNNRTAYG | 215 | |
| GAANNNNNNNNTCGC | 216 | |
| GATCAG | | |
| CCNGG | | |
| CCVVWGG | | |
| GGTANNNNNNTCG | 217 | |
| CAGAG | | TYPEIII |

| List AV Restriction site | Group of bacteria: *Salmonella paratyphi* SEQ ID NO |
|---|---|
| GCCNNNNNNTCG | 218 |
| GGCANNNNNCTC | 219 |
| GGNCC | |
| GGATG | |
| CWTCCAG | |
| GCSGC | |
| GTCGAC | |
| GGCGCC | |
| GCATC | |

| List AX Restriction site | Group of bacteria: *Shigella flexnerii* SEQ ID NO |
|---|---|
| GTANNNNNNNNGTCY | 220 |
| CTGCAG | |
| GCCGGC | |

| List AY Restriction site | Group of bacteria: *Vibrio parahaemolyticus* SEQ ID NO | |
|---|---|---|
| GGCANNNNNTTA | 221 | |
| CCNGG | | |
| CTCTTC | | |
| GNAATC | | TYPEIII |

TABLE 2 -continued

Additional List of frequent Restriction sites for each group of bacteria on interest

| List AZ Restriction site | Group of bacteria: *Yersinia pseudotuberculosis* SEQ ID NO | |
|---|---|---|
| CRAANNNNNNCTC | 222 | |
| CTGCAG | | |
| CGG TABLE 2 -continued Additional List of frequent Restriction sites for each group of bacteria on interest

| List BF Restriction site | Group of bacteria: *Selnomonas ruminatium* SEQ ID NO | |
|---|---|---|
| GCCGGC | | |
| CCGCGG | | |
| GAGAG | | TYPEIII |

| List BG Restriction site | Group of bacteria: *Mycoplasma mycoides* SEQ ID NO | |
|---|---|---|
| TCTAGA | | |
| GGNCC | | |
| CCTC | | |
| CCATC | | |
| GAN TABLE 2 -continued Additional List of frequent Restriction sites for each group of bacteria on interest

| | |
|---|---|
| CACAO | TYPEIII |
| GAWTC | TYPEIII |
| TAAATC | TYPEIII |

| List BM Restriction site | Group of bacteria: *pyrococcus abyssi* SEQ ID NO |
|---|---|
| GTAC | |
| CCGGNAG | |

| List BN Restriction site | Group of bacteria: *Selenomonas nominantium* SEQ ID NO |
|---|---|
| GGCCGAG | |
| CCGG | |

| List BO Restriction site | Group of bacteria: *Streptococcus ferus* SEQ ID NO |
|---|---|
| CTRYAG | |

| List BP Restriction site | Group of bacteria: *Streptomyces phaechromogenes* SEQ ID NO |
|---|---|
| CCNGG | |
| GCATGC | |
| TTAA | |
| GTAC | |
| CTAG | |

| List BQ Restriction site | Group of bacteria: *Streptomyces ghanaenis* SEQ ID NO |
|---|---|
| GCCGGC | |

| List BR Restriction site | Group of bacteria: *Enterobacter aerogenes* SEQ ID NO |
|---|---|
| YGGCCR | |
| GGNCC | |

| List BS Restriction site | Group of bacteria: *Morganella morganii* SEQ ID NO |
|---|---|
| GGNNCC | |
| CGATCG | |
| TGCA | |
| GCSGC | |

| List BT Restriction site | Group of bacteria: *Fusobacterium nucleatum* SEQ ID NO |
|---|---|
| GGCC | |
| AAGCTT | |
| ATGCAT | |
| GCGC | |

TABLE 2 -continued

Additional List of frequent Restriction sites for each group of bacteria on interest

| List BU Restriction site | Group of bacteria: *Porphyromonas endodontalis* SEQ ID NO |
|---|---|
| GCAGT | |
| GAGTC | |
| GATATC | |

| List BV Restriction site | Group of bacteria: *Porphyromonas gingivalis* SEQ ID NO |
|---|---|
| GAATTC | |

| List BW Restriction site | Group of bacteria: *Micrococcus luteus* SEQ ID NO |
|---|---|
| ACGCGT | |
| GAGCTC | |
| CAGNNNCTG | |

| List BX Restriction site | Group of bacteria: *Aeromonas hydrophila* SEQ ID NO |
|---|---|
| CTCGAG | |
| GCYYGAC | |
| YAAMGAG | |
| CAGCTG | |

| List BY Restriction site | Group of bacteria: *Bacillus anthracis* SEQ ID NO |
|---|---|
| RTCAGG | |
| GGWCC | |

| List BZ Restriction site | Group of bacteria: *Bartonella henselae* SEQ ID NO |
|---|---|
| AGTACT | |

| List CA Restriction site | Group of bacteria: *Bordetella pertussis* SEQ ID NO |
|---|---|
| GGNCC | |
| CTGCAG | |
| GRCGYC | |
| AGCCGCC | TYPEIII |

| List CB Restriction site | Group of bacteria: *Borrelia garinii* SEQ ID NO |
|---|---|
| CCGG | |

| List CC Restriction site | Group of bacteria: *Brucella canis* SEQ ID NO |
|---|---|
| CCATC | |
| GGCGCC | |
| CTNAG | |
| GGNCC | |
| GCCGGC | |

TABLE 2 -continued

Additional List of frequent Restriction sites for each group of bacteria on interest

| List CD Restriction site | Group of bacteria: *Campylobacter fetus* SEQ ID NO |
|---|---|
| CTGCAG | 37 |

| List CE Restriction site | Group of bacteria: *Clostridium tetani* SEQ ID NO |
|---|---|
| CGATCG | |
| CC

TABLE 2 -continued

Additional List of frequent Restriction sites for each group of bacteria on interest

| List CM Restriction site | Group of bacteria: SEQ ID NO | *Staphylococcus saprophyticus* |
|---|---|---|
| GCNGC | | |
| ACGT | | |

| List CN Restriction site | Group of bacteria: SEQ ID NO | *Streptococcus viridans* |
|---|---|---|
| GCCGGC | | |

| List CO Restriction site | Group of bacteria: SEQ ID NO | *Treponema pallidum* |
|---|---|---|
| GGWCC | | |
| TCGA | | |
| GMGAGC | | TYPEIII |

| List CP Restriction site | Group of bacteria: SEQ ID NO | *Ureaplasma urealyticum* |
|---|---|---|
| GCNGC | | |

| List CQ Restriction site | Group of bacteria: SEQ ID NO | *Yersinia pestis* |
|---|---|---|

| List CR | Group of bacteria: | *Propionibacterium acnes* |
|---|---|---|
| TAAGNNNNCTAY | 231 | |
| CYTANNNNNRTC | 232 | |
| CCCNNNNNRTTGY | 233 | |
| AGCAGY | | TYPEIII |
| ACCAGG | | TYPEIII |

In one embodiment, the present invention relates to a vector, preferably a vector included in a delivery vehicle, designed for a group of bacteria as shown in the above table 1 or 2 or a subgroup thereof and which does not comprise at least one restriction site selected from the group consisting of the list of restriction sites of the table 1 or 2 corresponding to the group of bacteria, for instance 1, 2, 3, 4, 5, 6 or 7 restriction sites selected from the group consisting of the list of restriction sites. Preferably, it relates to a vector, preferably a vector included in a delivery vehicle, designed for a group of bacteria of interest as shown in the table 1 or 2 or a subgroup thereof and which does not comprise any of restriction sites of this list of restriction sites of the table 1 or 2 corresponding to the group of bacteria.

In yet another embodiment, the invention concerns a bacteriophage genome or a phagemid comprising no more than 100, 90, 80, 70, 60, 50, 40, 30, 20, 10, 9, 8, 7, 6, 5, 4, 3, 2, 1 restriction site(s) recognized by the restriction enzymes encoded by each bacterium of a group of bacteria of interest. In a preferred embodiment, the bacteriophage genome or phagemid according to the invention comprises no more than 10 restriction sites recognized by the restriction enzymes encoded by each bacterium of a group of bacteria of interest. In a most preferred embodiment, the bacteriophage genome or phagemid according to the invention doesn't comprise any restriction site recognized by the restriction enzymes encoded by each bacterium of a group of bacteria of interest.

In an alternative embodiment, the invention concerns a bacteriophage genome or a phagemid in which at least 10%, 20%, 30%, 40%, 50%, 60%, 70%, 80%, 90%, 99% of the restriction sites recognized by the restriction enzymes encoded by each bacterium of a group of bacteria of interest and originally present in the vector have been removed.

In another alternative embodiment, the invention concerns a bacteriophage genome or a phagemid in which at least 10%, 20%, 30%, 40%, 50%, 60%, 70%, 80%, 90%, 99% of the restriction sites of the list shown in the above table for the group of bacteria of interest originally present in the vector have been removed.

In an alternative embodiment, the invention concerns a bacteriophage or a packaged phagemid in which at least 10%, 20%, 30%, 40%, 50%, 60%, 70%, 80%, 90%, 99% of the restriction sites recognized by the restriction enzymes encoded by each bacterium of a group of bacteria of interest and originally present in the vector have been removed.

The present invention further relates to a vector as defined above packaged into a bacteriophage capsid, the bacteriophage capsid being suitable for targeting the group of bacteria of interest. It also relates to a pharmaceutical composition comprising the vector as defined above packaged into a bacteriophage capsid, the use of the vector as defined above packaged into a bacteriophage capsid as a drug, and a method for treating a disease in a subject comprising administering the vector as defined above packaged into a bacteriophage capsid to the subject. More particularly, it relates to the use of the vector as defined above packaged into a bacteriophage capsid for delivering the vector to a group of bacteria of interest.

Bacteria of the genus *Actinomyces* can be infected by the following phages or by a vector packaged into the capsid of the following phages: Av-I, Av-2, Av-3, BF307, CT1, CT2, CT3, CT4, CT6, CT7, CT8 and 1281.

Bacteria of the genus *Aeromonas* can be infected by the following phages or by a vector packaged into the capsid of the following phages: AA-I, Aeh2, N, PM1, TP446, 3, 4, 11, 13, 29, 31, 32, 37, 43, 43-10T, 51, 54, 55R.1, 56, 56RR2, 57, 58, 59.1, 60, 63, Aeh1, F, PM2, 1, 25, 31, 40RR2.8t, (syn=44R), (syn=44RR2.8t), 65, PM3, PM4, PM5 and PM6.

Bacteria of the genus *Bacillus* can be infected by the following phages or by a vector packaged into the capsid of the following phages: A, aiz1, A1-K-I, B, BCJA1, BC1, BC2, BLL1, BL1, BP142, BSL1, BSL2, BS1, BS3, BS8, BS15, BS18, BS22, BS26, BS28, BS31, BS104, BS105, BS106, BTB, B1715V1, C, CK-I, Col1, Cor1, CP-53, CS-I, CSi, D, D, D, D5, ent1, FPB, FP9, FSi, FS2, FS3, FS5, FS8, FS9, G, GH8, GT8, GV-I, GV-2, GT-4, g3, g12, g13, g14, g16, g17, g21, g23, g24, g29, H2, ken1, KK-88, Kum1, Kyu1, J7W-1, LP52, (syn=LP-52), L7, Mex1, MJ-I, mor2, MP-7, MPIO, MP12, MP14, MP15, Neo1, N°2, N5, N6P, PBC1, PBLA, PBP1, P2, S-a, SF2, SF6, Sha1, Sil1, SP02, (syn=ΦSPP1), SPβ, STI, STi, SU-I1, t, TbI, Tb2, Tb5, TbIO, Tb26, Tb51, Tb53, Tb55, Tb77, Tb97, Tb99, Tb560, Tb595, Td8, Td6, Td15, TgI, Tg4, Tg6, Tg7, Tg9, TgIO, TgI1, Tg13, Tg15, Tg21, Tin1, Tin7, Tin8, Tin13, Tm3, Toc1, Tog1, toll, TP-I, TP-10vir, TP-15c, TP-16c, TP-17c, TP-19, TP35, TP51, TP-84, Tt4, Tt6, type A, type B, type C, type D, type E, Tφ3, VA-9, W, wx23, wx26, Yun1, α, γ, p1 1, φmed-2, φT, φμ-4, φ3 T, φ75, φ105, (syn=φ1O5), IA, IB, 1-97A, 1-97B, 2, 2, 3, 3, 3, 5, 12, 14, 20, 30, 35, 36, 37, 38, 41C, 51, 63, 64, 138D, I, II, IV, NN-*Bacillus* (13), ale1, AR1, AR2, AR3, AR7, AR9, Bace-11, (syn=11), Bastille, BL1, BL2, BL3, BL4, BL5, BL6, BL8, BL9, BP124, BS28, BS80, Ch, CP-51, CP-54, D-5, dar1, den1, DP-7, ent1, FoSi, FoS2, FS4, FS6, FS7, G, gall, gamma, GE1, GF-2, GSi, GT-I, GT-2, GT-3, GT-4, GT-5, GT-6, GT-7, GV-6, g15, 19, 110, ISi, K, MP9, MP13, MP21, MP23, MP24, MP28, MP29, MP30, MP32, MP34, MP36, MP37, MP39, MP40, MP41, MP43, MP44, MP45, MP47, MP50, NLP-I, No. 1, N17, N19, PBS1, PK1, PMBI, PMB12, PMJ1, S, SPO1, SP3, SP5, SP6, SP7, SP8, SP9, SP10, SP-15, SP50, (syn=SP-50), SP82, SST, sub1, SW, Tg8, Tg12, Tg13, Tg14, thu1, thuA, thuS, Tin4, Tin23, TP-13, TP33, TP50, TSP-I, type V, type VI, V, Vx, f322, (φe, φNR2, φ25, φ63, 1, 1, 2, 2C, 3NT, 4, 5, 6, 7, 8, 9, 10, 12, 12, 17, 18, 19, 21, 138, III, 4 (*B. megateriwn*), 4 (*B. sphaericus*), AR13, BPP-IO, BS32, BS107, B1, B2, GA-I, GP-IO, GV-3, GV-5, g8, MP20, MP27, MP49, Nf, PP5, PP6, SF5, Tg18, TP-I, Versailles, φ15, φ29, 1-97, 837/IV, mĪ-*Bacillus* (1), Bat1O, BSL1O, BSLI 1, BS6, BSI 1, BS16, BS23, BS101, BS102, g18, morl, PBL1, SN45, thu2, thu3, TmI, Tm2, TP-20, TP21, TP52, type F, type G, type IV, HN-BacMus (3), BLE, (syn=0c), BS2, BS4, BS5, BS7, B10, B12, BS20, BS21, F, MJ-4, PBA12, AP50, AP50-04, AP50-11, AP50-23, AP50-26, AP50-27 and Bam35. The following *Bacillus*-specific phages are defective: DLP10716, DLP-11946, DPBS, DPB12, DPB21, DPB22, DPB23, GA-2, M, No. IM, PBLB, PBSH, PBSV, PBSW, PBSX, PBSY, PBSZ, phi, SPa, type 1 and μ.

Bacteria of the genus *Bacteroides* can be infected by the following phages or by a vector packaged into the capsid of the following phages: ad 12, Baf-44, Baf-48B, Baf-64, Bf-I, Bf-52, B40-8, F1, β1, φA1, φBrO1, φBrO2, 11, 67.1, 67.3, 68.1, mt-*Bacteroides* (3), Bf42, Bf71, HN-Bdellovibrio (1) and BF-41.

Bacteria of the genus *Bordetella* can be infected by the following phages or by a vector packaged into the capsid of the following phages: 134 and NN-*Bordetella* (3).

Bacteria of the genus Borrellia can be infected by the following phages or by a vector packaged into the capsid of the following phages: NN-*Borrelia* (1) and NN-*Borrelia* (2).

Bacteria of the genus *Brucella* can be infected by the following phages or by a vector packaged into the capsid of the following phages: A422, Bk, (syn=Berkeley), BM29, FOi, (syn=FO1), (syn=FQ1), D, FP2, (syn=FP2), (syn=FD2), Fz, (syn=Fz75/13), (syn=Firenze 75/13), (syn=Fi), Fi, (syn=F1), Fim, (syn=FIm), (syn=Fim), FiU, (syn=Flu), (syn=FiU), F2, (syn=F2), F3, (syn=F3), F4, (syn=F4), F5, (syn=F5), F6, F7, (syn=F7), F25, (syn=F25), (syn=£25), F25U, (syn=F25u), (syn=F25U), (syn=F25V), F44, (syn=F44), F45, (syn=F45), F48, (syn=F48), I, Im, M, MC/75, M51, (syn=M85), P, (syn=D), S708, R, Tb, (syn=TB), (syn=Tbilisi), W, (syn=Wb), (syn=Weybridge), X, 3, 6, 7, 10/1, (syn=10), (syn=F8), (syn=F8), 12m, 24/11, (syn=24), (syn=F9), (syn=F9), 45/111, (syn=45), 75, 84, 212/XV, (syn=212), (syn=Fi0), (syn=F10), 371/XXIX, (syn=371), (syn=Fn), (syn=F1 1) and 513.

Bacteria of the genus *Burkholderia* can be infected by the following phages or by vector packaged into the capsid of the following phages: CP75, NN-*Burkholderia* (1) and 42.

Bacteria of the genus *Campylobacter* can be infected by the following phages or by a vector packaged into the capsid of the following phages: C type, NTCC12669, NTCC12670, NTCC12671, NTCC12672, NTCC12673, NTCC12674, NTCC12675, NTCC12676, NTCC12677, NTCC12678, NTCC12679, NTCC12680, NTCC12681, NTCC12682, NTCC12683, NTCC12684, 32f, 111c, 191, NN-*Campylobacter* (2), Vfi-6, (syn=V19), VfV-3, V2, V3, V8, V16, (syn=Vfi-1), V19, V20(V45), V45, (syn=V-45) and NN-*Campylobacter* (1).

Bacteria of the genus *Chlamydia* can be infected by the following phage or by a vector packaged into the capsid of the following phage: Chp1.

Bacteria of the genus *Clostridium* can be infected by the following phages or by a vector packaged into the capsid of the following phages: CAK1, CA5, Ca7, CEβ, (syn=1C), CEγ, Cld1, c-n71, c-203 Tox-, DEβ, (syn=ID), (syn=1Dt0X+), HM3, KM1, KT, Ms, NA1, (syn=Naltox+), PA135Oe, Pfó, PL73, PL78, PL81, P1, P50, P5771, P19402, 1CtOX+, 2CtOX\ 2D3 (syn=2Dt0X+), 3C, (syn=3Ctox+), 4C, (syn=4CtOX+), 56, III-1, NN-*Clostridium* (61), NB1t0X+, α1, CA1, HMT, HM2, PF15 P-23, P-46, Q-05, Q-oe, Q-16, Q-21, Q-26, Q-40, Q-46, S111, SA02, WA01, WA03, Wm, W523, 80, C, CA2, CA3, CPT1, CPT4, c1, c4, c5, HM7, H11/A1, H18/Ax, FWS23, Hi58ZA1, K2ZA1, K21ZS23, ML, NA2t0X; Pf2, Pf3, Pf4, S9ZS3, S41ZA1, S44ZS23, a2, 41, 112ZS23, 214/S23, 233/Ai, 234/S23, 235/S23, II-1, 11-2, 11-3, NN-*Clostridium* (12), CAI, F1, K, S2, 1, 5 and NN-*Clostridium* (8).

Bacteria of the genus *Corynebacterium* can be infected by the following phages: CGK1 (defective), A, A2, A3, A101, A128, A133, A137, A139, A155, A182, B, BF, B17, B18, B51, B271, B275, B276, B277, B279, B282, C, capi, CC1, CG1, CG2, CG33, CL31, Cog, (syn=CG5), D, E, F, H, H-I, hq1, hq2, 11ZH33, Ii/31, J, K, K, (syn=Ktox"), L, L, (syn=Ltox+), M, MC-I, MC-2, MC-3, MC-4, MLMa, N, O, ovi, ov2, ov3, P, P, R, RP6, RS29, S, T, U, UB1, ub2, UH1, UH3, uh3, uh5, uh6, β, (syn=βtox+), βhv64, βvir, γ, (syn=γtoχ-), γ19, δ, (syn=δ'ox+), p, (syn=ptoχ-), Φ9, φ984, ω, IA, 1/1180, 2, 2/1180, 5/1180, 5ad/9717, 7/4465, 8/4465, 8ad/10269, 10/9253, 13Z9253, 15/3148, 21/9253, 28, 29, 55, 2747, 2893, 4498 and 5848.

Bacteria of the genus *Enterococcus* are infected by the following phage: DF78, F1, F2, 1, 2, 4, 14, 41, 867, D1, SB24, 2BV, 182, 225, C2, C2F, E3, E62, DS96, H24, M35, P3, P9, SB1O1, S2, 2BII, 5, 182a, 705, 873, 881, 940, 1051, 1057, 21096C, NN-*Enterococcus* (1), PE1, F1, F3, F4, VD13, 1, 200, 235 and 341.

Bacteria of the genus *Erysipelothrix* can be infected by the following phage: NN-Eiysipelothrix (1).

Bacteria of the genus *Escherichia* can be infected by the following phages: BW73, B278, D6, D108, E, E1, E24, E41, FI-2, FI-4, FI-5, HI8A, FfI8B, i, MM, Mu, (syn=mu), (syn=MuI), (syn=Mu-I), (syn=MU-I), (syn=MuI), (syn=µ), 025, PhI-5, Pk, PSP3, P1, P1D, P2, P4 (defective), S1, Wφ, φK13, φR73 (defective), φ1, φ2, φ7, φ92, ψ (defective), 7 A, 8φ, 9φ, 15 (defective), 18, 28-1, 186, 299, HH-*Escherichia* (2), AB48, CM, C4, C16, DD-VI, (syn=Dd-Vi), (syn=DDVI), (syn=DDVi), E4, E7, E28, FI1, FI3, H, H1, H3, H8, K3, M, N, ND-2, ND-3, ND4, ND-5, ND6, ND-7, Ox-I (syn=OX1), (syn=HF), Ox-2 (syn=0x2), (syn=0X2), Ox-3, Ox-4, Ox-5, (syn=0X5), Ox-6, (syn=66F), (syn=φ66t), (syn=φ66t-)5 0111, PhI-I, RB42, RB43, RB49, RB69, S, Sal-I, Sal-2, Sal-3, Sal-4, Sal-5, Sal-6, TC23, TC45, TuII*-6, (syn=TuII*), TuIP-24, TuII*46, TuIP-60, T2, (syn=ganuTia), (syn=γ), (syn=PC), (syn=P.C.), (syn=T-2), (syn=T2), (syn=P4), T4, (syn=T-4), (syn=T4), T6, T35, α1, 1, IA, 3, (syn=Ac3), 3A, 3T+, (syn=3), (syn=M1), 5φ, (syn=φ5), 9266Q, CFO103, HK620, J, K, K1F, m59, no. A, no. E, no. 3, no. 9, N4, sd, (syn=Sd), (syn=SD), (syn=Sa)3 (syn=sd), (syn=SD), (syn=CD), T3, (syn=T-3), (syn=T3), T7, (syn=T-7), (syn=T7), WPK, W31, ΔH, φC3888, 9K3, φK7, φK12, φV-1, Φ04-CF, Φ05, Φ06, Φ07, φ1, φ1.2, φ20, φ95, φ263, φ1O92, φ1, φ11, (syn=φW), Ω8, 1, 3, 7, 8, 26, 27, 28-2, 29, 30, 31, 32, 38, 39, 42, 933W, NN-*Escherichia* (1), Esc-7-11, AC30, CVX-5, C1, DDUP, EC1, EC2, E21, E29, F1, F26S, F27S, Hi, HK022, HK97, (syn=ΦHK97), HK139, HK253, HK256, K7, ND-I, no. D, PA-2, q, S2, T1, (syn=α), (syn=P28), (syn=T-I), (syn=Tx), T3C, T5, (syn=T-5), (syn=T5), UC-I, w, β4, γ2, λ (syn=lambda), (syn=Φλ), ΦD326, φγ, Φ06, Φ7, 10, φ80, χ, (syn=χi), (syn=φχ), (syn=φχi), 2, 4, 4A, 6, 8A, 102, 150, 168, 174, 3000, AC6, AC7, AC28, AC43, AC57, AC81, AC95, HK243, K10, ZG/3A, 5, 5A, 21EL, H19-J and 933H.

Bacteria of the genus *Fusobacterium* are infected by the following phages or by a vector packaged into the capsid of the following phages: NN-*Fusobacterium* (2), fv83-554/3, fv88-531/2, 227, fv2377, fv2527 and fv8501.

Bacteria of the genus *Haemophilus* are infected by the following phages or by a vector packaged into the capsid of the following phages: HP1, S2 and N3.

Bacteria of the genus *Helicobacter* are infected by the following phages or by a vector packaged into the capsid of the following phages: HP1 and ^^-*Helicobacter* (1).

Bacteria of the genus *Klebsiella* are infected by the following phages or by a vector packaged into the capsid of the following phages: AIO-2, K14B, K16B, K19, (syn=K19), K114, K115, K121, K128, K129, KI32, K133, K135, K1106B, K1171B, K1181B, K1832B, AIO-I, AO-I, AO-2, AO-3, FC3-10, K, K11, (syn=KI1), K12, (syn=K12), K13, (syn=K13), (syn=K1 70/11), K14, (syn=K14), K15, (syn=K15), K16, (syn=K16), K17, (syn=K17), K18, (syn=K18), K119, (syn=K19), K127, (syn=K127), K131, (syn=K131), K135, K1171B, II, VI, IX, CI-I, K14B, K18, K111, K112, K113, K116, K117, K118, K120, K122, K123, K124, K126, K130, K134, K1106B, KIi65B, K1328B, KLXI, K328, P5046, 11, 380, III, IV, VII, VIII, FC3-11, K12B, (syn=K12B), K125, (syn=K125), K142B, (syn=K142), (syn=K142B), K1181B, (syn=KI1 81), (syn=K1181B), K1765/!, (syn=K1765/1), K1842B, (syn=K1832B), K1937B, (syn=K1937B), L1, φ28, 7, 231, 483, 490, 632 and 864/100.

Bacteria of the genus *Lepitospira* are infected by the following phages or by a vector packaged into the capsid of the following phages: LE1, LE3, LE4 and ~NN-*Leptospira* (1).

Bacteria of the genus *Listeria* are infected by the following phages or by a vector packaged into the capsid of the following phages: A511, 01761, 4211, 4286, (syn=BO54), A005, A006, A020, A500, A502, A511, A1 18, A620, A640, B012, B021, B024, B025, B035, B051, B053, B054, B055, B056, B1O1, BI 1O, B545, B604, B653, C707, D441, HSO47, H1OG, H8/73, H19, H21, H43, H46, H107, H108, HI 1O, H163/84, H312, H340, H387, H391/73, H684/74, H924A, PSA, U153, φMLUPS, (syn=P35), 00241, 00611, 02971 A, 02971C, 5/476, 5/911, 5/939, 5/11302, 5/11605, 5/11704, 184, 575, 633, 699/694, 744, 900, 1090, 1317, 1444, 1652, 1806, 1807, 1921/959, 1921/11367, 1921/11500, 1921/11566, 1921/12460, 1921/12582, 1967, 2389, 2425, 2671, 2685, 3274, 3550, 3551, 3552, 4276, 4277, 4292, 4477, 5337, 5348/11363, 5348/11646, 5348/12430, 5348/12434, 10072, 11355C, 11711A, 12029, 12981, 13441, 90666, 90816, 93253, 907515, 910716 and NN-Lisferia (15).

Bacteria of the genus *Morganella* are infected by the following phage or by a vector packaged into the capsid of the following phage: 47.

Bacteria of the genus *Mycobacterium* are infected by the following phages or by a vector packaged into the capsid of the following phages: 13, AG1, ALi, ATCC 11759, A2, B.C3, BG2, BK1, BK5, *butyricum*, B-I, B5, B7, B30, B35, Clark, C1, C2, DNAIII, DSP1, D4, D29, GS4E, (syn=GS4E), GS7, (syn=GS-7), (syn=GS7), IPa, lacticola, Legendre, Leo, L5, (syn=ΦL-5), MC-I, MC-3, MC-4, minetti, MTPHI 1, Mx4, MyF3P/59a, phlei, (syn=phlei 1), phlei 4, Polonus II, rabinovitschi, smegmatis, TM4, TM9, TM10, TM20, Y7, YIO, φ630, IB, IF, IH, 1/1, 67, 106, 1430, B1, (syn=Bol), B24, D, D29, F-K, F-S, HP, Polonus I, Roy, R1, (syn=R1-Myb), (syn=Ri), 11, 31, 40, 50, 103a, 103b, 128, 3111-D, 3215-D and NN-*Mycobacterium* (1).

Bacteria of the genus *Neisseria* are infected by the following phages or by a vector packaged into the capsid of the following phages: Group I, group II and NP1.

Bacteria of the genus *Nocardia* are infected by the following phages or by a vector packaged into the capsid of the following phages: MNP8, NJ-L, NS-8, N5 and TtiN-*Nocardia*.

Bacteria of the genus *Proteus* are infected by the following phages or by a vector packaged into the capsid of the following phages: Pm5, 13vir, 2/44, 4/545, 6/1004, 13/807, 20/826, 57, 67b, 78, 107/69, 121, 9/0, 22/608, 30/680, Pml, Pm3, Pm4, Pm6, Pm7, Pm9, PmIO, PmI 1, Pv2, π1, φm, 7/549, 9B/2, 10A/31, 12/55, 14, 15, 16/789, 17/971, 19A/653, 23/532, 25/909, 26/219, 27/953, 32A/909, 33/971, 34/13, 65, 5006M, 7480b, VI, 13/3a, Clichy 12, π2600, φχ7, 1/1004, 5/742, 9, 12, 14, 22, 24/860, 2600/D52, Pm8 and 24/2514.

Bacteria of the genus *Providencia* are infected by the following phages or by a vector packaged into the capsid of the following phages: PL25, PL26, PL37, 9211/9295, 9213/921 Ib, 9248, 7/R49, 7476/322, 7478/325, 7479, 7480, 9000/9402 and 9213/921 Ia.

Bacteria of the genus *Pseudomonas* are infected by the following phages or by a vector packaged into the capsid of the following phages: PfI, (syn=Pf-I), Pf2, Pf3, PP7, PRR1, 7s, im-*Pseudomonas* (1), AI-I, AI-2, B 17, B89, CB3, Col 2, Col 11, Col 18, Col 21, C154, C163, C167, C2121, E79, F8, ga, gb, H22, K1, M4, N2, Nu, PB-I, (syn=PB1), pf16, PMN17, PP1, PP8, Psal, PsPl, PsP2, PsP3, PsP4, PsP5, PS3, PS 17, PTB80, PX4, PX7, PYO1, PYO2, PYO5, PYO6, PYO9, PYO1O, PYO13, PYO14, PYO16, PYO18, PYO19, PYO20, PYO29, PYO32, PYO33, PYO35, PYO36, PYO37, PYO38, PYO39, PYO41, PYO42, PYO45, PYO47, PYO48, PYO64, PYO69, PYO103, P1K, SLP1, SL2, S2, UNL-I, wy, Yai, Ya4, Yan, φBE, φCTX, φC17, φKZ, (syn=ΦKZ), φ-LT, Φmu78, φNZ, φPLS-1, φST-I, φW-14, φ-2, 1/72, 2/79, 3, 3/DO, 4/237, 5/406, 6C, 6/6660, 7, 7v, 7/184, 8/280, 9/95, 10/502, 11/DE, 12/100, 12S, 16, 21, 24, 25F, 27, 31, 44, 68, 71, 95, 109, 188, 337, 352, 1214, HN-*Pseudomonas* (23), A856, B26, CI-I, CI-2, C5, D, gh-1, FI 16, HF, H90, K5, K6, K1 04, K109, K166, K267, N4, N5, O6N-25P, PE69, Pf, PPN25, PPN35, PPN89, PPN91, PP2, PP3, PP4, PP6, PP7, PP8, PP56, PP87, PP1 14, PP206, PP207, PP306, PP651, Psp231a, Pssy401, Pssy9220, psi, PTB2, PTB20, PTB42, PX1, PX3, PX10, PX12, PX14, PYO70, PY071, R, SH6, SH133, tf, Ya5, Ya7, φBS, ΦKf77, φ-MC, ΦmnF82, φPLS27, φPLS743, 9S-1, 1, 2, 2, 3, 4, 5, 6, 7, 7, 8, 9, 10, 11, 12, 12B, 13, 14, 15, 14, 15, 16, 17, 18, 19, 20, 20, 21, 21, 22, 23, 23, 24, 25, 31, 53, 73, 119x, 145, 147, 170, 267, 284, 308, 525, NN-*Pseudomonas* (5), af, A7, B3, B33, B39, BI-I, C22, D3, D37, D40, D62, D3112, F7, F10, g, gd, ge, gξ, Hwl2, Jb 19, KF1, L°, OXN-32P, 06N-52P, PCH-I, PC13-1, PC35-1, PH2, PH51, PH93, PH132, PMW, PM13, PM57, PM61, PM62, PM63, PM69, PM105, PM1 13, PM681, PM682, P04, PP1, PP4, PP5, PP64, PP65, PP66, PP71, PP86, PP88, PP92, PP401, PP711, PP891, Pssy41, Pssy42, Pssy403, Pssy404, Pssy420, Pssy923, PS4, PS-IO, Pz, SD1, SL1, SL3, SL5, SM, φC5, φC1 1, φC1 1-1, φC13, φC15, φMO, φX, φO4, φ1 1, φ240, 2, 2F, 5, 7m, 11, 13, 13/441, 14, 20, 24, 40, 45, 49, 61, 73, 148, 160, 198, 218, 222, 236, 242, 246, 249, 258, 269, 295, 297, 309, 318, 342, 350, 351, 357-1, 400-1, HN-*Pseudomonas* (6), G1O1, M6, M6a, L1, PB2, Pssy15, Pssy4210, Pssy4220, PYO12, PYO34, PYO49, PYO50, PYO51, PYO52, PYO53, PYO57, PYO59, PYO200, PX2, PX5, SL4, φO3, φO6 and 1214.

Bacteria of the genus *Rickettsia* are infected by the following phages or by a vector packaged into the capsid of the following phages: NN-*Rickettsia*.

Bacteria of the genus *Salmonella* are infected by the following phage: b, Beccles, CT, d, Dundee, f, Fels 2, GI, GUI, GVI, GVIII, k, K, i, j, L, 01, (syn=0-1), (syn=01), (syn=O-I), (syn=7), 02, 03, P3, P9a, P10, Sab3, Sab5, San1S, San17, SI, Taunton, Vil, (syn=Vil), 9, imSalmonella (1), N-I, N-5, N-IO, N-17, N-22, 11, 12, 16-19, 20.2, 36, 449C/C178, 966A/C259, a, B.A.O.R., e, G4, GUI, L, LP7, M, MG40, N-18, PSA68, P4, P9c, P22, (syn=P22), (syn=PLT22), (syn=PLT22), P22a1, P22-4, P22-7, P22-11, SNT-I, SNT-2, SP6, Villi, VilV, ViV, ViVI, ViVII, Worksop, Sj5, ε34, 1, 37, 1(40), (syn=φ1[40]), 1, 422, 2, 2.5, 3b, 4, 5, 6, 14(18), 8, 14(6, 7), 10, 27, 28B, 30, 31, 32, 33, 34, 36, 37, 39, 1412, SNT-3, 7-11, 40.3, c, C236, C557, C625, C966N, g, GV, G5, Gl 73, h, IRA, Jersey, MB78, P22-1, P22-3, P22-12, Sab1, Sab2, Sab2, Sab4, San1, San2, San3, San4, San6, San7, San8, San9, San13, San14, San16, San18, San19, San20, San21, San22, San23, San24, San25, San26, SasL1, SasL2, SasL3, SasL4, SasL5, S1BL, SII, Vill, φ1 1, 2, 3a, 3a1, 1010, Ym-*Salmonella* (1), N-4, SasL6 and 27.

Bacteria of the genus *Serratia* are infected by the following phages or by a vector packaged into the capsid of the following phages: A2P, PS20, SMB3, SMP, SMP5, SM2, V40, V56, ic, ΦCP-3, CP-6, 3M, 10/1a, 20A, 34CC, 34H, 38T, 345G, 345P, 501B, SMB2, SMP2, BC, BT, CW2, CW3, CW4, CW5, Lt232, L2232, L34, L.228, SLP, SMPA, V.43, σ, φCW1, ΦCP6-1, ΦCP6-2, ΦCP6-5, 3T, 5, 8, 9F, 10/1, 20E, 32/6, 34B, 34CT, 34P, 37, 41, 56, 56D, 56P, 60P, 61/6, 74/6, 76/4, 101/8900, 226, 227, 228, 229F, 286, 289, 290F, 512, 764a, 2847/10, 2847/1Oa, L.359 and SMB1.

Bacteria of the genus *Shigella* are infected by the following phages or by a vector packaged into the capsid of the following phages: Fsa, (syn=a), FSD2d, (syn=D2d), (syn=W2d), FSD2E, (syn=W2e), fV, F6, f7.8, H-Sh, PE5, P90, SfII, Sh, SHm, SHrv, (syn=HIV), SHvi, (syn=HVI), SHVvm, (syn=HVIII), SKγ66, (syn=gamma 66), (syn=γβρ), (syn=γ66b), SKm, (syn=SIIIb)5 (syn=UI), SKw, (syn=Siva), (syn=IV), SIC™, (syn=SIVA.), (syn=IVA), SKvi, (syn=KVI), (syn=Svi), (syn=VI), SKvm, (syn=Svm), (syn=VIII), SKVIIIA, (syn=SvmA), (syn=VIIIA), STvi, STK, STxl, STxn, S66, W2, (syn=D2c), (syn=D20), φ1, φIVb 3-SO-R, 8368-SO-R, F7, (syn=FS7), (syn=K29), FIO, (syn=FSIO), (syn=K31), II, (syn=alfa), (syn=FSa), (syn=K1 8), (syn=α), 12, (syn=a), (syn=K19), SG33, (syn=G35), (syn=SO-35/G), SG35, (syn=SO-55/G), SG3201, (syn=SO-3201/G), SHn, (syn=HII), SHv, (syn=SHV), SHx, SHX, SKn, (syn=K2), (syn=KII), (syn=Sn), (syn=SsII), (syn=II), SKrv, (syn=Sm), (syn=SsIV), (syn=IV), SK1Va, (syn=Swab), (syn=SsIVa), (syn=IVa), SKV, (syn=K4), (syn=KV), (syn=SV), (syn=SsV), (syn=V), SKx, (syn=K9), (syn=KX), (syn=SX), (syn=SsX), (syn=X), STV, (syn=T35), (syn=35-50-R), STvm, (syn=T8345), (syn=8345-SO—S-R), Wl, (syn=D8), (syn=FSD8), W2a, (syn=D2A), (syn=FS2a), DD-2, Sf6, FSi, (syn=FI), SF6, (syn=F6), SG42, (syn=SO-42/G), SG3203, (syn=SO-3203/G), SKF12, (syn=SsF12), (syn=F12), (syn=F12), STn, (syn=1881-SO-R), γ66, (syn=gamma 66a), (syn=Ssy66), φ2, BI1, DDVII, (syn=DD7), FSD2b, (syn=W2B), FS2, (syn=F2), (syn=F2), FS4, (syn=F4), (syn=F4), FS5, (syn=F5), (syn=F5), FS9, (syn=F9), (syn=F9), FI 1, P2-SO-S, SG36, (syn=SO-36/G), (syn=G36), SG3204, (syn=SO-3204/G), SG3244, (syn=SO-3244/G), SHi, (syn=HI), SHvπ, (syn=HVII), SHK, (syn=HIX), SHx1, SHxπ, (syn=HXn), SKI, KI, (syn=SI), (syn=SsI), SKVII, (syn=KVII), (syn=Svπ), (syn=SsVII), SKIX, (syn=KIX), (syn=Six), (syn=SsIX), SKXII, (syn=KXII), (syn=Sxn), (syn=SsXII), STi, STffl, STrv, STVi, STvπ, S70, S206, U2-S0-S, 3210-SO-S, 3859-SO-S, 4020-SO-S, φ3, φ5, φ7, φ8, φ9, φ1O, φ1 1, φ13, φ14, φ18, SHm, (syn=Hπi), SHχi, (syn=HXt) and SKxI, (syn=KXI), (syn=Sχi), (syn=SsXI), (syn=XI).

Bacteria of the genus *Staphylococcus* are infected by the following phages or by a vector packaged into the capsid of the following phages: A, EW, K, Ph5, Ph9, PhIO, Ph13, P1, P2, P3, P4, P8, P9, P1O, RG, SB-i, (syn=Sb-I), S3K, Twort, ΦSK311, φ812, 06, 40, 58, 119, 130, 131, 200, 1623, STC1, (syn=stcl), STC2, (syn=stc2), 44AHJD, 68, AC1, AC2, A6"C", A9"C", b581, CA-I, CA-2, CA-3, CA-4, CA-5, DI1, L39x35, L54a, M42, N1, N2, N3, N4, N5, N7, N8, NIO, Ni 1, N12, N13, N14, N16, Ph6, Ph12, Ph14, UC-18, U4, U15, S1, S2, S3, S4, S5, X2, Z1, φB5-2, φD, ω, 11, (syn=φ11), (syn=P11-M15), 15, 28, 28A, 29, 31, 31B, 37, 42D, (syn=P42D), 44A, 48, 51, 52, 52A, (syn=P52A), 52B, 53, 55, 69, 71, (syn=P71), 71A, 72, 75, 76, 77, 79, 80, 80a, 82, 82A, 83 A, 84, 85, 86, 88, 88A, 89, 90, 92, 95, 96, 102, 107, 108, 111, 129-26, 130, 130A, 155, 157, 157A, 165, 187, 275, 275A, 275B, 356, 456, 459, 471, 471A, 489, 581, 676, 898, 1139, 1154A, 1259, 1314, 1380, 1405, 1563, 2148, 2638A, 2638B, 2638C, 2731, 2792A, 2792B, 2818, 2835, 2848A, 3619, 5841, 12100, AC3, A8, A1O, A13, b594n, D, HK2, N9, N15, P52, P87, SI, S6, Z4, φRE, 3A, 3B, 3C, 6, 7, 16, 21, 42B, 42C, 42E, 44, 47, 47A5 47C, 51, 54, 54x1, 70, 73, 75, 78, 81, 82, 88, 93, 94, 101, 105, 110, 115, 129/16, 174, 594n, 1363/14, 2460 and mS-*Staphylococcus* (1).

Bacteria of the genus *Streptococcus* are infected by the following phages or by a vector packaged into the capsid of the following phages: EJ-I, NN-Streptococais (1), a, C1, FL0Ths, H39, Cp-I, Cp-5, Cp-7, Cp-9, Cp-IO, AT298, A5, a1O/J1, a1O/J2, a1O/J5, a1O/J9, A25, BTl1, b6, CA1, c20-l, c20-2, DP-I, Dp-4, DTI, ET42, e1O, FA101, FEThs, FK, FKKIOI, FKLIO, FKP74, FKH, FLOThs, FyIO1, f1, F10, F20140/76, g, GT-234, HB3, (syn=HB-3), HB-623, HB-746, M102, O1205, φ01205, PST, PO, P1, P2, P3, P5, P6, P8, P9, P9, P12, P13, P14, P49, P50, P51, P52, P53, P54, P55, P56, P57, P58, P59, P64, P67, P69, P71, P73, P75, P76, P77, P82, P83, P88, sc, sch, sf, Sfl1 1, (syn=SFiI 1), (syn=9SFi11), (syn=ΦSfi1 1), (syn=φSfi1 1), sfi19, (syn=SFi19), (syn=φSFi19), (syn=φSfi1 9), Sfi21, (syn=SFi21), (syn=φSFi21), (syn=φSE21), ST0, STX, st2, ST2, ST4, S3, (syn=9S3), s265, Φ17, φ42, Φ57, φ80, φ81, φ82, φ83, φ84, φ85, φ86, φ87, φ88, φ89, φ90, φ91, φ92, φ93, φ94, φ95, φ96, φ97, φ98, φ99, φ1OO, φ1O1, φ1O2, φ227, Φ7201, ω1, ω2, ω3, ω4, ω5, ω6, ω8, ω1O, 1, 6, 9, 1OF, 12/12, 14, 17SR, 19S, 24, 50/33, 50/34, 55/14, 55/15, 70/35, 70/36, 71/ST15, 71/45, 71/46, 74F, 79/37, 79/38, 80/J4, 80/J9, 80/ST16, 80/15, 80/47, 80/48, 101, 103/39, 103/40, 121/41, 121/42, 123/43, 123/44, 124/44, 337/ST17 and mStreptococcus (34).

Bacteria of the genus *Treponema* are infected by the following phage or by a vector packaged into a capsid of the following phage: NN-*Treponema* (1).

Bacteria of the genus *Vibrio* are infected by the following phages or by a vector packaged into the capsid of the following phages: CTXΦ, fs, (syn=si), fs2, Ivpf5, Vf12, Vf33, VPIΦ, VSK, v6, 493, CP-T1, ET25, kappa, K139, Labol)XN-69P, OXN-86, O6N-21P, PB-I, P147, rp-1, SE3, VA-I, (syn=VcA-I), VcA-2, VP1, VP2, VP4, VP7, VP8, VP9, VP1O, VP17, VP18, VP19, X29, (syn=29 d'Herelle), t, ΦHAWI-1, ΦHAWI-2, ΦHAWI-3, HAWI-4, ΦHAWI-5, ΦHAWI-6, ΦHAWI-7, XHAWI-8, ΦHAWI-9, ΦHAWI-10, ΦHC1-1, ΦHC1-2, ΦHC1-3, ΦHC1-4, ΦHC2-1, ΦHC2-2, ΦHC2-3, ΦHC2-4, ΦHC3-1, ΦHC3-2, ΦHC3-3, ΦHD1S-1, ΦHD1S-2, ΦHD2S-1, ΦHD2S-2, ΦHD2S-3, ΦHD2S-4, ΦHD2S-5, ΦHDO-1, ΦHDO-2, ΦHDO-3, ΦHDO-4, ΦHDO-5, ΦHDO-6, ΦKL-33, ΦKL-34, ΦKL-35, ΦKL-36, ΦKWH-2, ΦKWH-3, ΦKWH-4, ΦMARQ-1, ΦMARQ-2, ΦMARQ-3, ΦMOAT-1, ΦO139, ΦPEL1A-1, ΦPEL1A-2, ΦPEL8A-1, ΦPEL8A-2, ΦPEL8A-3, ΦPEL8C-1, ΦPEL8C-2, ΦPEL13 A-1, ΦPEL13B-1, ΦPEL13B-2, ΦPEL13B-3, ΦPEL13B-4, ΦPEL13B-5, ΦPEL13B-6, ΦPEL13B-7, ΦPEL13B-8, ΦPEL13B-9, ΦPEL13B-10, φVP143, φVP253, 016, φ138, 1-II, 5, 13, 14, 16, 24, 32, 493, 6214, 7050, 7227, II, (syn=group II), (syn=φ2), V, VIII, ~m-*Vibrio* (13), KVP20, KVP40, nt-1, O6N-22P, P68, e1, e2, e3, e4, e5, FK, G, I, K, nt-6, N1, N2, N3, N4, N5, O6N-34P, OXN-72P, OXN-85P, OXN-100P, P, Ph-I, PL163/10, Q, S, T, (p92, 1-9, 37, 51, 57, 70A-8, 72A-4, 72A-10, 110A-4, 333, 4996, I (syn=group I), III (syn=group III), VI, (syn=A-Saratov), VII, IX, X, HN-*Vibrio* (6), pA1, 7, 7-8, 70A-2, 71A-6, 72A-5, 72A-8, 108A-10, 109A-6, 109A-8, 110A-1, 110A-5, 110A-7, hv-1, OXN-52P, P13, P38, P53, P65, P108, Pill, TP13 VP3, VP6, VP12, VP13, 70A-3, 70A-4, 70A-10, 72A-1, 108A-3, 109-B1, 110A-2, 149, (syn=9149), IV, (syn=group IV), NN-*Vibrio* (22), VP5, VPI1, VP15, VP16, α1, α2, α3a, α3b, 353B and HN-*Vibrio* (7).

Bacteria of the genus *Yersinia* are infected by the following phages or by a vector packaged into the capsid of the following phages: H, H-1, H-2, H-3, H-4, Lucas 110, Lucas 303, Lucas 404, YerA3, YerA7, YerA20, YerA41, 3/M64-76, 5/G394-76, 6/C753-76, 8/C239-76, 9/F18167, 1701, 1710, PST, 1/F2852-76, D'Herelle, EV, H, Kotljarova, PTB, R, Y, YerA41, φYer03-12, 3, 4/C1324-76, 7/F783-76, 903, 1/M6176 and Yer2AT.

Vector

Vectors are well known from the man skilled in the art. The vector according to the invention may be a DNA vector or a RNA vector. The vector may comprise an origin of replication, a selectable marker, and a suitable site for the insertion of a gene or a sequence of interest such as a multiple cloning site. By "sequence of interest" is referred to a sequence providing a therapeutic effect.

Preferably, the vector is an expression vector, preferably a vector that allows expression in a bacterium.

The expression vector according to the invention may comprise a promoter, a translation initiation sequence such as a ribosomal binding site and a start codon, a termination codon, and a transcription termination sequence. The expression vector according to the invention may also comprise regulatory regions such as enhancers, silencers and boundary elements/insulators to direct the level of transcription of a given gene.

The expression vector can be a vector for stable or transient expression of a gene.

The vector according to the invention may be selected from the group consisting of plasmids, bacteriophage genomes, phagemids, virus genomes, cosmids, and artificial chromosomes. Preferably, the vector according to the invention is a bacteriophage genome or a phagemid.

In a preferred embodiment, the vector according to the invention is a bacteriophage genome. The bacteriophage genome according to the invention comprises all the genes that are needed for its replication within the bacterium, the formation of new virions and their release. The genome can be wildtype or genetically engineered.

The bacteriophage genome according to the invention may the genome of a bacteriophage as defined above, for instance selected from the group consisting of IKe, CTX-φ, Pf1, Pf2, Pf3, Myoviridae (such as P1-like, P2-like, Mu-like, SPO1-like, and phiH-like bacteriophages); Siphoviridae (such as λ-like, γ-like, T1-like, c2-like, L5-like, psiM1-like, phiC31-like, and N15-like bacteriophages); Podoviridae (such as phi29-like, P22-like, and N4-like bacteriophages); Tectiviridae (such as Tectivirus); Corticoviridae (such as Corticovirus); Lipothrixviridae (such as Alphalipothrixvirus, Betalipothrixvirus, Gammalipothrixvirus, and Deltalipothrixvirus); Plasmaviridae (such as Plasmavirus); Rudiviridae (such as Rudivirus); Fuselloviridae (such as Fusellovirus); Inoviridae (such as Inovirus, Plectrovirus, M13-like and fd-like bacteriophages); Microviridae (such as Microvirus, Spiromicrovirus, Bdellomicrovirus, and Chlamydiamicrovirus); Leviviridae (such as Levivirus, and Allolevivirus), Cystoviridae (such as Cystovirus), coliphages (e.g., infects *Escherichia coli*), B1 (e.g. infects *Bacteroides* thetaiotamicron), ATCC 51477-B1, B40-8, or Bf-1 (e.g. infects *B. fragilis*), phiHSCO1—e.g. infects *B. caccae*), phiHSC02 (e.g. infects *B. ovatus*), phiC2, phiC5, phiC6, phiC8, phiCD119, or phiCD27 (e.g. infects *Clostridium difficile*), KP01K2, K1 1, Kpn5, KP34, or JDOO1 (e.g. infects *Klebsiella pneumoniae*), phiNM1 or 80alpha (e.g. infects *Staphylococcus aureus*), IME-EF1 (e.g. infects *Enterococcus faecalis*), ENB6 or C33 (e.g. infects *Enterococcus faecium*), and phiKMV, PAK-P1, LKD16, LKA1, delta, sigma-1, J-l (e.g. infects *Pseudomonas aeruginosa*), T2, T4, T5, T7, RB49, phiX174, R17, PRD1 bacteriophages, and any bacteriophage derived thereof.

The bacteriophage genome according to the invention may be the genome of a bacteriophage having a lytic or a non-lytic cycle of replication.

Genomes of bacteriophages having a non-lytic cycle of replication according to the invention may be selected from the group consisting of IKe, CTX-φ, Pf1, Pf2, Pf3, Myoviridae (such as P1-like, P2-like, Mu-like, SPO1-like, and phiH-like bacteriophages); Siphoviridae (such as λ-like, γ-like, T1-like, c2-like, L5-like, psiM1-like, phiC31-like, and N15-like bacteriophages); Podoviridae (such as phi29-like, P22-like, and N4-like bacteriophages); Tectiviridae (such as Tectivirus); Corticoviridae (such as Corticovirus); Lipothrixviridae (such as Alphalipothrixvirus, Betalipothrixvirus, Gammalipothrixvirus, and Deltalipothrixvirus); Plasmaviridae (such as Plasmavirus); Rudiviridae (such as Rudivirus); Fuselloviridae (such as Fusellovirus); Inoviridae (such as Inovirus, Plectrovirus, M13-like and fd-like bacteriophages); Microviridae (such as Microvirus, Spiromicrovirus, Bdellomicrovirus, and Chlamydiamicrovirus); Leviviridae (such as Levivirus, and Allolevivirus), Cystoviridae (such as Cystovirus), coliphages (e.g., infects *Escherichia coli*), B1 (e.g. infects *Bacteroides* thetaiotamicron), ATCC 51477-B1, B40-8, or Bf-1 (e.g. infects *B. fragilis*), phiH-SCO1—e.g. infects *B. caccae*), phiHSC02 (e.g. infects *B. ovatus*), phiC2, phiC5, phiC6, phiC8, phiCD119, or phiCD27 (e.g. infects *Clostridium difficile*), KP01K2, K11, Kpn5, KP34, or JDOO1 (e.g. infects *Klebsiella pneumoniae*), phiNM1 or 80alpha (e.g. infects *Staphylococcus aureus*), IME-EF1 (e.g. infects *Enterococcus faecalis*), ENB6 or C33 (e.g. infects *Enterococcus faecium*), and phiKMV, PAK-P1, LKD16, LKA1, delta, sigma-1, J-1 (e.g. infects *Pseudomonas aeruginosa*) bacteriophages, and any bacteriophage derived thereof.

The genomes of bacteriophages having a non-lytic cycle (also called lysogenic cycle) of replication according to the invention are from temperate bacteriophages. Preferably, the genomes of bacteriophages having a non-lytic cycle of replication according to the invention are selected from the group consisting of P2-like and Lambda-like (λ-like) bacteriophages. More preferably, the genomes of bacteriophages having a non-lytic cycle of replication according to the invention are selected from Lambda-like bacteriophages, preferably from the group consisting of HK022, mEP237, HK97, HK629, HK630, mEP043, mEP213, mEP234, mEP390, mEP460, mEPx1, mEPx2, phi80, mEP234 bacteriophages, and any bacteriophage derived thereof.

Genomes of bacteriophages having a lytic cycle of replication according to the invention may be selected from the group consisting of the genomes of T2, T4, T5, T7, RB49, phiX174, R17, PRD1 bacteriophages, and any bacteriophage derived thereof.

Genomes of other bacteriophages may be used in accordance with the present invention.

Preferably, the bacteriophage genome according to the invention is the genome of a lethal bacteriophage, i.e. having only a lytic cycle of reproduction.

Alternatively, the bacteriophage genome according to the invention is the genome of a non-lethal bacteriophage, i.e. temperate bacteriophage having both a lysogenic and a lytic cycle of reproduction.

In another preferred embodiment, the vector according to the invention is a phagemid. The phagemid according to the invention comprises a phage packaging site and optionally a plasmid origin of replication (ori), in particular a bacterial origin of replication and/or a phage origin of replication. Preferably, the phagemid according to the invention does not comprise a plasmid origin of replication and thus cannot replicate by itself once injected into a bacterium.

Phagemids according to the invention may be derived from any of the bacteriophage disclosed herein. In particular, phagemids according to the invention are suitable for being packaged into any of the bacteriophage disclosed herein and especially comprise the packaging site and optionally the bacteriophage origin of replication. The phage replication origin can initiate, with complementation of a complete phage genome, the replication of the plasmid for later encapsulation into the different capsids. The phage origin of replication can be the wild-type or non-wildtype sequence of the M13, f1, φX174, P4, lambda, P2, Lambda-like bacteriophages, HK022, mEP237, HK97, HK629, HK630, mEP043, mEP213, mEP234, mEP390, mEP460, mEPx1, mEPx2, phi80, mEP234, T2, T4, T5, T7, RB49, phiX174, R17, PRD1 P1-like, P2-like, P22-like N15-like bacteriophages.

Packaging sites include but are not limited to SPP1 (SPP1 pac site), P1 (P1 pac site), T1 (T1 pac site), T7 (T7 concatemer junction), lambda (λcos site), P4 (P4 cos site), mu (mu pac site), P22 (P22 pac site), φ 8 (φ>8 pac site), Sf6 (Sf6 pac site), 149 (149 pac site), and A1 122 (A1 122-concatamer junction). For most bacterial viruses, the packaging site is termed the pac site. In some cases, the packaging site is referred to as a concatemer junction (e.g. T7 concatemer junction). In every case, the packaging site is substantially isolated from sequences naturally occurring adjacent thereto in the bacteria virus genome.

Phagemids according to the invention may be selected from the group consisting of lambda derived phagemids, P4 derived phagemids, M13-derived phagemids, such as the ones containing the f1 origin for filamentous phage packaging such as, for example, pBluescript II SK (+/−) and KS (+/−) phagemids, pBC SK and KS phagemids, pADL and PI derived phagemids (see, e.g., Westwater C A et al., Microbiology 148, 943-50 (2002); Kittleson J T et al., ACS Synthetoc Biology 1, 583-89 (2012); Mead D A et al, Biotechnology 10, 85-102 (1988)).

Preferably, phagemids according to the invention are selected from lambda derived phagemids and P4 derived phagemids.

More preferably, phagemids according to the invention are selected from lambda derived phagemids, preferably selected from the group consisting of HK022 derived phagemids, mEP237 derived phagemids, HK97 derived phagemids, HK629 derived phagemids, HK630 derived phagemids, mEP043 derived phagemids, mEP213 derived phagemids, mEP234 derived phagemids, mEP390 derived phagemids, mEP460 derived phagemids, mEPx1 derived phagemids, mEPx2 derived phagemids, phi80 derived phagemids, mEP234 derived phagemids.

Other phagemids may be used in accordance with the present invention.

For instance, the vector according to the invention, preferably a bacteriophage genome or a phagemid, may also comprise a sequence of interest. The sequence of interest is a sequence which provides a technical effect in the bacteria, preferably which provides a therapeutic effect. The sequence of interest can be for instance a sequence capable of killing a bacterium, of modulating the expression of a gene, especially suppressing the expression or increasing the expression of one or several genes, or of modulating the production of a metabolite, especially decreasing or increasing the expression of one or several metabolites.

For instance, the vector according to the invention, preferably a bacteriophage genome or a phagemid, may also comprise additional genes, in particular genes that are aimed to be expressed in bacteria of interest.

In one embodiment, the vector may comprise a sequence of interest, for instance a sequence encoding a protein of interest. The protein of interest can be a bacteriocin, which can be a proteinaceous toxin produced by bacteria to kill or inhibit growth of other bacteria. Bacteriocins are categorized in several ways, including producing strain, common resistance mechanisms, and mechanism of killing. Such bacteriocin had been described from gram negative bacteria (e.g. microcins, colicin-like bacteriocins and tailocins) and from gram positive bacteria (e.g. Class I, Class II, Class III or Class IV bacteriocins). Then, the protein of interest can be selected from the group consisting of a toxin selected in the group consisting of microcins, colicin-like bacteriocins, tailocins, Class I, Class II, Class III and Class IV bacteriocins.

In a particular embodiment, a programmable nuclease circuits can be added to the vector so as to be delivered to bacteria of interest. This programmable nuclease circuit may be able to mediate in vivo sequence-specific elimination of bacteria that contain a target gene of interest (e.g. a gene that is harmful to humans). Some embodiments of the present disclosure relate to engineered variants of the Type II CRISPR-Cas (Clustered Regularly Interspaced Short Palindromic Repeats-CRISPR-associated) system of *Streptococcus pyogenes*, which can be used in accordance with the present disclosure to reverse antibiotic resistance in, or specifically destroy, a wide range of microbial organisms. Other programmable nucleases that can be used in accordance with the present disclosure include other CRISPR-Cas systems, engineered TALEN (Transcription Activator-Like Effector Nuclease) variants and engineered zinc finger nuclease (ZFN) variants. Thus, the engineered autonomously distributed circuits provided herein, in some embodiments, may be used to selectively cleave DNA encoding a gene of interest such as, for example, a toxin gene, a virulence factor gene, an antibiotic resistance gene, a remodeling gene or a modulatory gene (cf. WO2014124226 and US2015/0064138).

The CRISPR system contains two distinct elements, i.e. i) an endonuclease, in this case the CRISPR associated nuclease (Cas or "CRISPR associated protein") and ii) a guide RNA. The guide RNA is in the form of a chimeric RNA which consists of the combination of a CRISPR (RNAcr) bacterial RNA and a RNAtracr (trans-activating RNA CRISPR) (Jinek et al., Science 2012). The gRNA combines the targeting specificity of the cRNA corresponding to the "spacing sequences" that serve as guides to the Cas proteins, and the conformational properties of the Rtracr in a single transcript. When the gRNA and the Cas protein are expressed simultaneously in the cell, the target genomic sequence can be permanently modified or interrupted. The modification is advantageously guided by a repair matrix.

The sequence of interest according to the present invention comprises a nucleic acid sequence encoding Cas protein. A variety of CRISPR enzymes are available for use as a sequence of interest on the plasmid according to the present invention. In some embodiments, the CRISPR enzyme is a Type II CRISPR enzyme. In some embodiments, the CRISPR enzyme catalyzes DNA cleavage. In some other embodiments, the CRISPR enzyme catalyzes RNA cleavage. In one embodiment, the CRISPR enzymes may be coupled to a sgRNA. In certain embodiments, the sgRNA targets a gene selected in the group consisting of an antibiotic resistance gene, virulence gene, toxin gene and any other genes conferring a selective advantage to a pathogen or allowing discrimination between pathogenic and non-pathogenic strains of the same bacterial species.

Non-limiting examples of Cas proteins include Cas1, Cas1B, Cas2, Cas3, Cas4, Cas5, Cas6, Cas7, Cas8, Cas9 (also known as Csn1 and Csx12), Cas 10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx1O, Csx16, CsaX, Csx3, Csx1, Csx15, Csf1, Csf2, Csf3, Csf4, homologues thereof, or variants thereof. In some embodiments, the CRISPR enzyme cleaves both strands of the target nucleic acid at the Protospacer Adjacent Motif (PAM) site.

In a particular embodiment, the CRISPR enzyme is any Cas9 protein, for instance any naturally-occurring bacterial Cas9 as well as any variants, homologs or orthologs thereof.

By "Cas9" is meant a protein Cas9 (also called Csn1 or Csx12) or a functional protein, peptide or polypeptide fragment thereof, i.e. capable of interacting with the guide RNA(s) and of exerting the enzymatic activity (nuclease) which allows it to perform the double-strand cleavage of the DNA of the target genome. "Cas9" can thus denote a modified protein, for example truncated to remove domains of the protein that are not essential for the predefined functions of the protein, in particular the domains that are not necessary for interaction with the gRNA (s).

The sequence encoding Cas9 (the entire protein or a fragment thereof) as used in the context of the invention can be obtained from any known Cas9 protein (Makarova et al., 2011). Examples of Cas9 proteins useful in the present invention include, but are not limited to, Cas9 proteins of *Streptococcus pyogenes, Streptococcus thermophilus, Streptococcus mutans, Campylobacter jejuni, Francisella novicida* and *Neisseria meningitidis*. Other Cas9 proteins that can be used in the present invention are also described in the article by Fonfara et al, 2013.

In a particular embodiment, the nucleic sequence of interest is a CRISPR/Cas9 system for the reduction of gene expression or inactivation a gene selected in the group consisting of an antibiotic resistance gene, virulence gene, toxin gene and any other genes conferring a selective advantage to a pathogen or allowing discrimination between pathogenic and non-pathogenic strains of the same bacterial species.

In one embodiment, the CRISPR/Cas9 system is used to target and inactivate a virulence factor. A virulence factor can be any substance produced by a pathogen that alter host-pathogen interaction by increasing the degree of damage done to the host. Virulence factors are used by pathogens in many ways, including, for example, in cell adhesion or colonization of a niche in the host, to evade the host's immune response, to facilitate entry to and egress from host cells, to obtain nutrition from the host, or to inhibit other physiological processes in the host. Virulence factors can include enzymes, endotoxins, adhesion factors, motility factors, factors involved in complement evasion, and factors that promote biofilm formation. For example, such targeted virulence factor gene can be *E. coli* virulence gene factor such as eaeA, EHEC-HlyA, Stx1 (VT1), Stx2 (VT2), Stx2c (VT2c), Stx2d (VT2d), Stx2e (VT2e) and Stx2f (VT2f), fimH, neuC, kpsE, sfa, foe, iroN, aer, iha, papC, papGI, papGII, papGIII, hlyC, cnf1, hra, sat, ireA, usp ompT, ibeA, malX, fyuA, irp2, traT, afaD, ipaH, eltB, estA, bfpA, eae, aaiC, aatA, TEM, CTX, SHV.

In another embodiment, the CRISPR/Cas9 system is used to target and inactivate an antibiotic resistance gene (e.g. ampicillin resistance gene).

In another embodiment, the CRISPR/Cas9 system is used to target and inactivate a bacterial toxin gene. Bacterial toxin can be classified as either exotoxins or endotoxins. Exotoxins are generated and actively secreted; endotoxins remain part of the bacteria. The response to a bacterial toxin can involve severe inflammation and can lead to sepsis. Such toxin can be for example Botulinum neurotoxin, Tetanus toxin, Staphylococus toxins, Diphteria toxin, Anthrax toxin, Alpha toxin, Pertussis toxin, Shiga toxin, Heat-stable enterotoxin (E. coli ST) or any toxin described in Henkel et al., (Toxins from Bacteria in EXS. 2010; 100: 1-29).

Other genetic circuits, preferably programmable, can be added to the vector so as to be delivered to bacteria of interest. Preferably, the genetic circuit added to the vector leads to cell death of the bacteria of interest. For example, the genetic circuit added to the vector may encodes holins or toxins. Alternatively, the genetic circuit added to the vector does not lead to bacteria death. For example, the genetic circuit may encode reporter genes leading to a luminescence or fluorescence signal. Alternatively, the genetic circuit may comprise proteins and enzymes achieving a useful function such as modifying the metabolism of the bacteria or the composition of its environment.

The vector may further comprise a selection marker. In a particular embodiment, the selection marker provides a selective advantage to the bacterial cell infected by the plasmid, such as resistance to antibiotics, resistance to heavy metals, complementing a host auxotrophy and/or exhibiting fluorescent or luminescent proteins.

The inclusion of the suitable selectable marker gene in a plasmid allows testing and/or detection for successful delivery of the plasmid according to the invention. The plasmid according to the invention may comprise one or more nucleic acid sequences encoding selectable marker such as auxotrophic markers (e.g., LEU2, URA3, TRP 1 or HIS3, DapA, ThyA), detectable labels such as fluorescent or luminescent proteins (e.g., GFP, eGFP, DsRed, CFP, YFP), or protein conferring resistance to a chemical/toxic compound (e.g., MGMT gene conferring resistance to temozolomide, kanamycin resistance, chloramphenicol resistance, etc.) or any combinations thereof. These markers can be used to select or detect host cells comprising the vector according to the invention and can be easily chosen by the skilled person according to the host cell.

For most purposes, an antibiotic resistance gene is a commonly used selection marker to facilitate molecular biology cloning of the plasmid and to allow the detection or selection of bacteria transformed by such plasmid. Antibiotic resistance genes are well known in the art and include but are not limited to ampicillin resistance (Amp), chloramphenicol resistance (Cm), tetracycline resistance (Tet), kanamycin resistance (Kan), hygromycin resistance (Qiyg or hph genes), and zeomycin resistance (Zeo).

Delivery Vehicle

The vector according to the invention is preferably included in a delivery vehicle that allows the transfer of the vector into a bacterium of interest.

Delivery vehicle are well known from the man skilled in the art. There are several common types of delivery vehicle including, without limitation, chemical based delivery vehicle, non-chemical-based delivery vehicles, particle-based delivery vehicles, nanoparticle-based delivery vehicles, donor bacteria, bacteriophage scaffold, and virus scaffold.

Chemical based delivery vehicle according to the invention may be selected from the group consisting of cyclodextrin, calcium phosphate, cationic polymers, cationic liposomes, and a mixture thereof.

Non-chemical based delivery vehicle according to the invention may be selected from the group consisting of electroporation, sonoporation, optical transfection, and a mixture thereof.

Particle based delivery vehicle according to the invention may be selected from the group consisting of gene gun, magnetofection, impalefection, particle bombardment, cell-penetrating peptides and a mixture thereof.

Nanoparticle based delivery vehicle can be, for example, nucleic acid nanocages.

Donor bacteria may be delivery vehicle for conjugative plasmids. Donor bacteria according to the invention include, without limitation, commensal bacteria and probiotic bacteria.

In a preferred embodiment, the delivery vehicle according to the invention is a bacteriophage scaffold or capsid or bacteriophage virus like particles. Preferably, the vector included in the bacteriophage scaffold is a bacteriophage genome or a phagemid.

Thus, in a particularly preferred embodiment, the invention concerns a bacteriophage or a packaged phagemid, wherein the vector is a defined above.

The bacteriophage genome or the phagemid can be made to work with bacteriophage scaffolds from natural, engineered or evolved bacteriophages. Preferably, the bacteriophage scaffold is from natural bacteriophages.

Preferably, the bacteriophage according to the invention comprises a bacteriophage genome and a bacteriophage scaffold of same origin, i.e. from the same species, preferably from the same strain. Even more preferably, the bacteriophage scaffold according to the invention is assembled from the proteins encoded by the genes of the bacteriophage genome.

Preferably, the packaged phagemid according to the invention comprises a bacteriophage scaffold which is of same origin as the bacteriophage genes of the phagemid, i.e. the bacteriophage scaffold of the packaged phagemid is a bacteriophage scaffold of the same species, preferably the same strain, as the bacteriophage DNA from which the phagemid is derived. Preferably, the packaged phagemid according to the invention comprises a bacteriophage scaffold which is of same origin as the bacteriophage packaging sites of the phagemid.

The bacteriophage or the packaged phagemid according to the invention may be lethal or non-lethal. Preferably, the bacteriophage or packaged phagemid according to the invention is a lethal bacteriophage or a lethal packaged phagemid. Alternatively, the bacteriophage or packaged phagemid according to the invention is a non-lethal bacteriophage or a non-lethal packaged phagemid.

Use of a Vector According to the Invention and Method

In another aspect, the invention also relates to the use of a vector according to the invention, preferably a bacteriophage genome or a phagemid according to the invention, or of a vector included in a delivery vehicle according to the invention, preferably a bacteriophage or a packaged phagemid according to the invention, to deliver the vector into bacteria, preferably bacteria of interest according to the invention.

In a particular embodiment, the vector according to the invention comprises a genetic circuit, preferably programmable. The genetic circuit according to the invention can lead to the cell death of the bacteria, i.e., the bacteria of the interest. For example, the genetic circuit added to the vector may encode holins or toxins. Alternatively, the genetic circuit added to the vector does not lead to bacteria death. For example, the genetic circuit may encode reporter genes leading to a luminescence or fluorescence signal. Alternatively, the genetic circuit may comprise proteins and enzymes achieving a useful function such as modifying the metabolism of the bacteria or the composition of its environment.

In yet another aspect, the invention concerns the use of a vector according to the invention, preferably a bacteriophage genome or a phagemid according to the invention, or of a vector included in a delivery vehicle according to the invention, preferably a bacteriophage or a packaged phagemid according to the invention, as a research tool, in particular for improving the frequency of delivery and/or broadening the strains of bacteria in which the vector can be delivered.

The invention also relates to a method for preparing a vector according to the invention, wherein the method comprises:
(i) selecting a group of bacteria of interest;
(ii) based on the vector sequence, identifying the restriction sites recognized by the restriction enzymes encoded by the group of bacteria;
(iii) modifying the sequence of the vector according to the invention, preferably a bacteriophage genome or a phagemid according to the invention, or a vector included in a delivery vehicle according to the invention, preferably a bacteriophage or a packaged phagemid according to the invention, so as it comprises no more than 100, 90, 80, 70, 60, 50, 40, 30, 20, 10, 9, 8, 7, 6, 5, 4, 3, 2, 1 restriction site(s) recognized by the restriction enzymes encoded by each bacterium of the group of bacteria;
(iv) optionally preparing the modified vector, in particular by nucleic acid synthesis or by mutation of the vector.

Preferably, in step (ii), the frequency of the restriction enzymes in the group of bacteria of interest is determined and, in step (iii), the sequence of the vector is modified to remove at least one restriction site of the restriction enzymes frequently encoded by the group of bacteria of interest, preferably 1, 2, 3, 4, 5, 6, or 7 restriction sites of the restriction enzymes frequently encoded by the group of bacteria of interest, more preferably to remove the restriction sites of the restriction enzymes frequently encoded by the group of bacteria of interest.

The invention further relates to a method for preparing a vector according to the invention, wherein the method comprises:
(i) selecting a group of bacteria of interest;
(ii) identifying the restriction enzymes encoded by the group of bacteria of interest and determining the frequency of bacteria encoding the restriction enzymes in the group of interest;
(iii) optionally selecting the restriction sites of the restriction enzymes frequently encoded by the group of bacteria of interest;
(iv) modifying the sequence of the vector according to the invention, preferably a bacteriophage genome or a phagemid according to the invention, or a vector included in a delivery vehicle according to the invention, preferably a bacteriophage or a packaged phagemid according to the invention, so as to remove the restriction sites of the restriction enzymes frequently encoded by the group of bacteria of interest;
(v) optionally preparing the modified vector, in particular by nucleic acid synthesis or by mutation of the vector.

In a preferred embodiment, the sequence of the vector is modified so as it does not comprise any restriction sites recognized by the restriction enzymes encoded by each bacterium of the group of bacteria. The restriction sites can be modified either by changing the sequence or the modification state (e.g., methylation or not, glycosylation or not) so as to prevent the recognition by the restriction enzyme (i.e., so as to prevent the restriction enzyme to bind and cut the vector). For the type III restriction enzymes, there is no need to remove all sites because one site by itself is not cleaved. Restriction is only happening if there are two inversely oriented restriction sites. Therefore, the vector is modified so as to remove the presence of two inversely oriented restriction sites.

Preferably, the group of bacteria is as described above.

Preferably, the group of bacteria consists in bacterial strains of a single species.

In another aspect, the invention concerns an in-vitro method for delivering a vector in bacteria of interest, wherein the method further comprises administering to a bacterium of said group of bacteria the modified vector according to the invention, preferably a bacteriophage genome or a phagemid according to the invention, or the modified vector included in a delivery vehicle according to the invention, preferably a bacteriophage or a packaged phagemid according to the invention.

Preferably, the modified vector according to the invention, preferably a bacteriophage genome or a phagemid according to the invention, or the modified vector included in a delivery vehicle according to the invention, preferably a bacteriophage or a packaged phagemid according to the invention comprises no more than 100, 90, 80, 70, 60, 50, 40, 30, 20, 10, 9, 8, 7, 6, 5, 4, 3, 2, 1 restriction site(s), preferably no restriction site, recognized by the restriction enzymes encoded by the bacterium to which it is administered.

Use as a Drug

In another aspect, the invention also relates to a vector according to the invention, preferably a bacteriophage genome or a phagemid according to the invention, or of a vector included in a delivery vehicle according to the invention, preferably a bacteriophage or a packaged phagemid according to the invention, for use as a drug.

The invention also relates to the use of a vector according to the invention, preferably a bacteriophage genome or a phagemid according to the invention, or of a vector included in a delivery vehicle according to the invention, preferably a bacteriophage or a packaged phagemid according to the invention, for the manufacture of a medicine.

In a preferred embodiment, the invention concerns a vector according to the invention, preferably a bacteriophage genome or a phagemid according to the invention, or a vector included in a delivery vehicle according to the invention, preferably a bacteriophage or a packaged phagemid according to the invention, for use in the treatment of a disease selected from the group consisting of an infection, preferably a bacterial infection, inflammatory diseases, autoimmune diseases, cancers, and brain disorders. Preferably, the disease is caused by a group of bacteria of interest. The invention concerns a vector according to the invention, preferably a bacteriophage genome or a phagemid according to the invention, or a vector included in a delivery vehicle according to the invention, preferably a bacteriophage or a packaged phagemid according to the invention, for use for improving the general health of a subject, for eradicating pathogenic or virulent bacteria, for improving the effectiveness of drugs, and/or for modifying the composition of the microbiome.

The invention also concerns a vector according to the invention, preferably a bacteriophage genome or a phagemid according to the invention, or a vector included in a delivery vehicle according to the invention, preferably a bacteriophage or a packaged phagemid according to the invention, for the preparation of a medicament for treating a disease selected from the group consisting of infections, preferably bacterial infections, inflammatory diseases, auto-immune diseases, cancers, and brain disorders. Preferably, the disease is caused by a group of bacteria of interest. The invention concerns a vector according to the invention, preferably a bacteriophage genome or a phagemid according to the invention, or a vector included in a delivery vehicle according to the invention, preferably a bacteriophage or a packaged phagemid according to the invention, for the preparation of a medicament for improving the general health of a subject, for eradicating pathogenic or virulent bacteria, for improving the effectiveness of drugs, and/or for modifying the composition of the microbiome.

The invention further relates to a method for treating in a subject a disease selected from the group consisting of an infection, preferably a bacterial infection, inflammatory diseases, auto-immune diseases, cancers, metabolic disease or disorder, obesity, diabetes and brain disorders, wherein a therapeutically effective amount of a vector according to the invention, preferably a bacteriophage genome or a phagemid according to the invention, or a vector included in a delivery vehicle according to the invention, preferably a bacteriophage or a packaged phagemid according to the invention, is administered to said subject suffering from the disease. Preferably, the disease is caused by a group of bacteria of interest. Particularly, the disease caused by bacteria may be selected from the group consisting of abdominal cramps, acute epiglottitis, arthritis, bacteraemia, botulism, Brucellosis, brain abscess, chancroid venereal disease, *Chlamydia*, conjunctivitis, cholecystitis, Lyme disease, diarrhea, diphtheria, duodenal ulcers, endocarditis, erysipelothricosis, enteric fever, fever, glomerulonephritis, gastroenteritis, gastric ulcers, Guillain-Barre syndrome, tetanus, gonorrhoea, leptospirosis, leprosy, listeriosis, tuberculosis, Lady Widermere syndrome, Legionaire's disease, meningitis, mucopurulent conjunctivitis, myonecrosis-gas gangrene, *Mycobacterium avium* complex, neonatal necrotizing enterocolitis, nocardiosis, nosocomial infection, otitis, phalyngitis, pneumonia, peritonitis, purpuric fever, Rocky Mountain spotted fever, shigellosis, syphilis, sinusitis, sigmoiditis, septicaemia, subcutaneous abscesses, tularaemia, tracheobronchitis, tonsillitis, typhoid fever, urinary infection, whooping cough.

The infection according to the invention may be selected from the group consisting of skin infections such as acne, intestinal infections such as esophagitis, gastritis, enteritis, colitis, sigmoiditis, rectitis, and peritonitis, urinary tract infections, vaginal infections, female upper genital tract infections such as salpingitis, endometritis, oophoritis, myometritis, parametritis and infection in the pelvic peritoneum, respiratory tract infections such as pneumonia, intra-amniotic infections, odontogenic infections, endodontic infections, fibrosis, meningitis, bloodstream infections, nosocomial infection such as catheter-related infections, hospital acquired pneumonia, post-partum infection, hospital acquired gastroenteritis, hospital acquired urinary tract infections, or a combination thereof.

Preferably, the infection according to the invention is caused by a bacterium presenting an antibiotic resistance.

In a most preferred embodiment, the infection is caused by a bacterium of interest as listed above.

Preferably the vector according to the invention, preferably a bacteriophage genome or a phagemid according to the invention, or the vector included in a delivery vehicle according to the invention, preferably a bacteriophage or a packaged phagemid according to the invention, only target the bacterial strain responsible of the infection and thus allow the subject to be treated to conserve a healthy microbiome.

The metabolic disease or disorder according to the invention may be selected from the group consisting of Metabolic brain diseases, Calcium metabolism disorders, DNA repair-deficiency disorders, Glucose metabolism disorders, Hyperlactatemia, Iron metabolism disorders, Lipid metabolism disorders, Malabsorption syndromes, Metabolic syndrome X, Inborn error of metabolism, Mitochondrial diseases, Phosphorus metabolism disorders, Porphyrias and Proteostasis deficiency.

The metabolic disease or disorder according to the invention may be selected from the group consisting of type 1 diabetes; type 2 diabetes; metabolic syndrome; Bardet-Biedel syndrome; Prader-Willi syndrome; non-alcoholic fatty liver disease; tuberous sclerosis; Albright hereditary osteodystrophy; brain-derived neurotrophic factor (BDNF) deficiency; Single-minded 1 (SEVI1) deficiency; leptin deficiency; leptin receptor deficiency; pro-opiomelanocortin (POMC) defects; proprotein convertase subtilisin/kexin type 1 (PCSK1) deficiency; Src homology 2B1 (SH2B 1) deficiency; pro-hormone convertase 1/3 deficiency; melanocortin-4-receptor (MC4R) deficiency; Wilms tumor, aniridia, genitourinary anomalies, and mental retardation (WAGR) syndrome; pseudohypoparathyroidism type 1A; Fragile X syndrome; Borjeson-Forsmann-Lehmann syndrome; Alstrom syndrome; Cohen syndrome; and ulnar-mammary syndrome Acid-base imbalance Symptoms associated with the aforementioned diseases and conditions include, but are not limited to, one or more of weight gain, obesity, fatigue, hyperlipidemia, hyperphagia, hyperdipsia, polyphagia, polydipsia, polyuria, pain of the extremities, numbness of the extremities, blurry vision, nystagmus, hearing loss, cardiomyopathy, insulin resistance, light sensitivity, pulmonary disease, liver disease, liver cirrhosis, liver failure, kidney disease, kidney failure, seizures, hypogonadism, and infertility.

Metabolic diseases are associated with a variety of physiological changes, including but not limited to elevated glucose levels, elevated triglyceride levels, elevated cholesterol levels, insulin resistance, high blood pressure, hypogonadism, subfertility, infertility, abdominal obesity, pro-thrombotic conditions, and pro-inflammatory conditions.

In a particular embodiment, the invention also relates to a method for personalized treatment for an individual in need of treatment for a bacterial infection comprising: i) obtaining a biological sample from the individual and determining a group of bacterial DNA sequences from the sample; ii) based on the determining of the sequences, identifying one or more pathogenic bacterial strains or species that were in the sample; and iii) administering to the individual a vector according to the invention, preferably a bacteriophage genome or a phagemid according to the invention, or a vector included in a delivery vehicle according to the invention, preferably a bacteriophage or a packaged phagemid according to the invention, wherein the vector according to the invention, preferably a bacteriophage genome or a phagemid according to the invention, or a vector included in a delivery vehicle according to the invention, preferably a bacteriophage or a packaged phagemid according to the invention has been modified to comprise no more than 100 restriction sites, preferably no more than 50 restrictions sites, more preferably no more than 10 restriction sites, even more preferably comprises no restriction site recognized by the restriction enzymes encoded by each pathogenic bacterial strain or species identified in the sample, thereby targeting the one or more pathogenic bacterial strains or species. The pathogenic bacteria are defined as the group of bacteria of interest. Preferably, the vector is as defined above for targeting the group of pathogenic bacteria. It has been modified to remove at least one restriction site of the restriction enzymes frequently encoded by the group of bacteria of interest, preferably 1, 2, 3, 4, 5, 6, or 7 restriction sites of the restriction enzymes frequently encoded by the group of bacteria of interest, more preferably to remove the restriction sites of the restriction enzymes frequently encoded by the group of bacteria of interest.

Preferably, the biological sample comprises pathological and non-pathological bacterial species, and subsequent to administering the vector according to the invention, preferably a bacteriophage genome or a phagemid according to the invention, or the vector included in a delivery vehicle according to the invention, preferably a bacteriophage or a packaged phagemid according to the invention, to the individual, the amount of pathogenic bacteria on or in the individual are reduced, but the amount of non-pathogenic bacteria is not reduced. Particularly, the vector according to the invention, preferably a bacteriophage genome or a phagemid according to the invention, or a vector included in a delivery vehicle according to the invention, preferably a bacteriophage or a packaged phagemid according to the invention leads to the death of the targeted bacteria (i.e. either by lysis or by the expression of a toxin or a programmable nuclease circuit).

In a particular embodiment, the invention concerns a vector according to the invention, preferably a bacteriophage genome or a phagemid according to the invention, or a vector included in a delivery vehicle according to the invention, preferably a bacteriophage or a packaged phagemid according to the invention, for use in the treatment of pathologies involving bacteria of the human microbiome, such as inflammatory and auto-immune diseases, cancers, infections, metabolic disease, metabolic disorders such as obesity and diabetes, or brain disorders. Indeed, some bacteria of the microbiome, without triggering any infection, can secrete molecules that will induce and/or enhance inflammatory or auto-immune diseases or cancer development. Some bacteria of the microbiome can also secrete molecules that will affect the brain.

In another particular embodiment, the invention concerns a vector according to the invention, preferably a bacteriophage genome or a phagemid according to the invention, or a vector included in a delivery vehicle according to the invention, preferably a bacteriophage or a packaged phagemid according to the invention, for use in order to improve the effectiveness of drugs. Indeed, some bacteria of the microbiome, without being pathogenic by themselves, are known to be able to metabolize drugs and to modify them in ineffective or harmful molecules.

The present invention also relates to a non-therapeutic use of a vector according to the invention, preferably a bacteriophage genome or a phagemid according to the invention, or a vector included in a delivery vehicle according to the invention, preferably a bacteriophage or a packaged phagemid according to the invention. For instance, the non-therapeutic use can be a cosmetic use or a use for improving the well-being of a subject, in particular a subject who does not suffer from a disease. Accordingly, the present invention also relates to a cosmetic composition or a non-therapeutic composition comprising a vector according to the invention, preferably a bacteriophage genome or a phagemid according to the invention, or a vector included in a delivery vehicle according to the invention, preferably a bacteriophage or a packaged phagemid according to the invention.

Pharmaceutical or Veterinary Composition

In yet another aspect, the invention also concerns a pharmaceutical or veterinary composition comprising or consisting essentially in a vector according to the invention, preferably a bacteriophage genome or a phagemid according to the invention, or a vector included in a delivery vehicle according to the invention, preferably a bacteriophage or a packaged phagemid according to the invention.

The pharmaceutical or veterinary composition comprises at least one excipient or pharmaceutically acceptable carrier.

Preferably, the pharmaceutical or veterinary composition further comprises another active ingredient, preferably an antibiotic or another antibacterial agent, even more preferably an antibiotic.

Preferably, the antibiotic according to the invention is selected from the group consisting in penicillins such as penicillin G, penicillin K, penicillin N, penicillin O, penicillin V, methicillin, benzylpenicillin, nafcillin, oxacillin, cloxacillin, dicloxacillin, ampicillin, amoxicillin, pivampicillin, hetacillin, bacampicillin, metampicillin, talampicillin, epicillin, carbenicillin, ticarcillin, temocillin, mezlocillin, and piperacillin; cephalosporins such as cefacetrile, cefadroxil, cephalexin, cefaloglycin, cefalonium, cefaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan, cefoxitin, loracarbef, cefbuperazone, cefminox, cefotetan, cefoxitin, cefotiam, cefcapene, cefdaloxime, cefdinir, cefditoren, cefetamet, cefixime, cefmenoxime, cefodizime, cefotaxime, cefovecin, cefpimizole, cefpodoxime, cefteram, ceftamere, ceftibuten, ceftiofur, ceftiolene, ceftizoxime, ceftriaxone, cefoperazone, ceftazidime, latamoxef, cefclidine, cefepime, cefluprenam, cefoselis, cefozopran, cefpirome, cefquinome, flomoxef, ceftobiprole, ceftaroline, ceftolozane, cefaloram, cefaparole, cefcanel, cefedrolor, cefempidone, cefetrizole, cefivitril, cefmatilen, cefmepidium, cefoxazole, cefrotil, cefsumide, ceftioxide, cefuracetime, and nitrocefin; polymyxins such as polysporin, neosporin, polymyxin B, and polymyxin E, rifampicins such as rifampicin, rifapentine, and rifaximin; Fidaxomicin; quinolones such as cinoxacin, nalidixic acid, oxolinic acid, piromidic acid, pipemidic acid, rosoxacin, ciprofloxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin, temafloxacin, tosufloxacin, clinafloxacin, gatifloxacin, gemifloxacin, moxifloxacin, sitafloxacin, trovafloxacin, prulifloxacin, delafloxacin, nemonoxacin, and zabofloxacin; sulfonamides such as sulfafurazole, sulfacetamide, sulfadiazine, sulfadimidine, sulfafurazole, sulfisomidine, sulfadoxine, sulfamethoxazole, sulfamoxole, sulfanitran, sulfadimethoxine, sulfametho-xypyridazine, sulfametoxydiazine, sulfadoxine, sulfametopyrazine, and terephtyl; macrolides such as azithromycin, clarithromycin, erythromycin, fidaxomicin, telithromycin, carbomycin A, josamycin, kitasamycin, midecamycin, oleandomycin, solithromycin, spiramycin, troleandomycin, tylosin, and roxithromycin; ketolides such as telithromycin, and cethromycin; lluoroketolides such as solithromycin; lincosamides such as lincomycin, clindamycin, and pirlimycin; tetracyclines such as demeclocycline, doxycycline, minocycline, oxytetracycline, and tetracycline; aminoglycosides such as amikacin, dibekacin, gentamicin, kanamycin, neomycin, netilmicin, sisomicin, tobramycin, paromomycin, and streptomycin; ansamycins such as geldanamycin, herbimycin, and rifaximin; carbacephems such as loracarbef; carbapenems such as ertapenem, doripenem, imipenem (or cilastatin), and meropenem; glycopeptides such as teicoplanin, vancomycin, telavancin, dalbavancin, and oritavancin; lincosamides such as clindamycin and lincomycin; lipopeptides such as daptomycin; monobactams such as aztreonam; nitrofurans such as furazolidone, and nitrofurantoin; oxazolidinones such as linezolid, posizolid, radezolid, and torezolid; teixobactin, clofazimine, dapsone, capreomycin, cycloserine, ethambutol, ethionamide, isoniazid, pyrazinamide, rifabutin, arsphenamine, chloramphenicol, fosfomycin, fusidic acid, metronidazole, mupirocin, platensimycin, quinupristin (or dalfopristin), thiamphenicol, tigecycline, tinidazole, trimethoprim, alatrofloxacin, fidaxomycin, nalidixice acide, rifampin, derivatives and combination thereof.

The invention also concerns the pharmaceutical or veterinary composition of the invention for use in the treatment of an infection, preferably a bacterial infection.

The invention also relates to the use of a pharmaceutical or veterinary composition according to the invention for the manufacture of a medicine for treating infections, preferably bacterial infections, in a subject.

The invention further relates to a method for treating in a subject an infection, preferably a bacterial infection, wherein a therapeutically effective amount of a pharmaceutical or veterinary composition according to the invention is administered to said subject suffering from an infection.

Preferably, the infection is as described above for the use of a vector.

In a most preferred embodiment, the infection is caused by a bacterium of interest as listed above.

Subject, Regimen and Administration

The subject according to the invention is an animal, preferably a mammal, even more preferably a human. However, the term "subject" can also refer to non-human animals, in particular mammals such as dogs, cats, horses, cows, pigs, sheep, donkeys, rabbits, ferrets, gerbils, hamsters, chinchillas, rats, mice, guinea pigs and non-human primates, among others, that are in need of treatment.

The human subject according to the invention may be a human at the prenatal stage, a new-born, a child, an infant, an adolescent or an adult, in particular an adult of at least 40 years old, preferably an adult of at least 50 years old, still more preferably an adult of at least 60 years old, even more preferably an adult of at least 70 years old.

In a preferred embodiment, the subject has been diagnosed with an infection, preferably a bacterial infection. Diagnostic method of infections is well known by the man skilled in the art.

In a particular embodiment, the infection presents a resistance to treatment, preferably the infection present an antibiotic resistance.

In a particular embodiment, the subject has already received at least one line of treatment, preferably several lines of treatment, prior to the administration of a vector according to the invention, preferably a bacteriophage genome or a phagemid according to the invention, of a vector included in a delivery vehicle according to the invention, preferably a bacteriophage or a packaged phagemid according to the invention, or of a pharmaceutical or veterinary composition according to the invention.

The vector according to the invention, preferably a bacteriophage genome or a phagemid according to the invention, of a vector included in a delivery vehicle according to the invention, preferably a bacteriophage or a packaged phagemid according to the invention, or of a pharmaceutical or veterinary composition according to the invention may be administered by any conventional route of administration.

In particular, a vector according to the invention, preferably a bacteriophage genome or a phagemid according to the invention, a vector included in a delivery vehicle according to the invention, preferably a bacteriophage or a packaged phagemid according to the invention, or a pharmaceutical or veterinary composition according to the invention can be formulated for a topical, enteral, oral, parenteral, intranasal, intravenous, intramuscular, subcutaneous or intraocular administration and the like.

Preferably, the vector according to the invention, preferably a bacteriophage genome or a phagemid according to the invention, the vector included in a delivery vehicle according to the invention, preferably a bacteriophage or a packaged phagemid according to the invention, or the pharmaceutical or veterinary composition according to the invention, may be administered by enteral or parenteral route of administration. When administered parenterally, the vector according to the invention, preferably a bacteriophage genome or a phagemid according to the invention, the vector included in a delivery vehicle according to the invention, preferably a bacteriophage or a packaged phagemid according to the invention, or the pharmaceutical or veterinary composition according to the invention, is preferably administered by intravenous route of administration. When administered enterally, the vector according to the invention, preferably a bacteriophage genome or a phagemid according to the invention, the vector included in a delivery vehicle according to the invention, preferably a bacteriophage or a packaged phagemid according to the invention, or the pharmaceutical or veterinary composition according to the invention, is preferably administered by oral route of administration.

The pharmaceutical or veterinary composition is formulated in accordance with standard pharmaceutical or veterinary practice (Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art.

For oral administration, the pharmaceutical or veterinary composition can be formulated into conventional oral dosage forms such as tablets, capsules, powders, granules and liquid preparations such as syrups, elixirs, and concentrated drops. Nontoxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials, are also necessary. For example, starch, gelatine, sugars such as lactose or dextrose, and natural or synthetic gums can be used as binders. Disintegrants are also necessary in the tablets to facilitate break-up of the tablet. Disintegrants include starches, clays, celluloses, algins, gums and cross-linked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

For transdermal administration, the pharmaceutical or veterinary composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used. The active compounds can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

Pharmaceutical or veterinary compositions according to the invention may be formulated to release the active ingredients substantially immediately upon administration or at any predetermined time or time period after administration.

Preferably, the treatment with the vector according to the invention, preferably a bacteriophage genome or a phagemid according to the invention, the vector included in a delivery vehicle according to the invention, preferably a bacteriophage or a packaged phagemid according to the invention, or the pharmaceutical or veterinary composition according to the invention start no longer than a month, preferably no longer than a week, after the diagnosis of the infection. In a most preferred embodiment, the treatment start the day of the diagnosis.

The vector according to the invention, preferably a bacteriophage genome or a phagemid according to the invention, the vector included in a delivery vehicle according to the invention, preferably a bacteriophage or a packaged phagemid according to the invention, or the pharmaceutical or veterinary composition according to the invention, may be administered as a single dose or in multiple doses.

Preferably, the treatment is administered regularly, preferably between every day and every month, more preferably between every day and every two weeks, more preferably between every day and every week, even more preferably the treatment is administered every day. In a particular embodiment, the treatment is administered several times a day, preferably 2 or 3 times a day, even more preferably 3 times a day.

The duration of treatment with the vector according to the invention, preferably a bacteriophage genome or a phagemid according to the invention, the vector included in a delivery vehicle according to the invention, preferably a bacteriophage or a packaged phagemid according to the invention, or the pharmaceutical or veterinary composition according to the invention is preferably comprised between 1 day and 20 weeks, more preferably between 1 day and 10 weeks, still more preferably between 1 day and 4 weeks, even more preferably between 1 day and 2 weeks. In a particular embodiment, the duration of the treatment is of about 1 week. Alternatively, the treatment may last as long as the infection persists.

The amount of vector according to the invention, preferably a bacteriophage genome or a phagemid according to the invention, of vector included in a delivery vehicle according to the invention, preferably a bacteriophage or a packaged phagemid according to the invention, or of pharmaceutical or veterinary composition according to the invention to be administered has to be determined by standard procedure well known by those of ordinary skills in the art. Physiological data of the patient (e.g. age, size, and weight) and the routes of administration have to be taken into account to determine the appropriate dosage, so as a therapeutically effective amount will be administered to the patient.

In a preferred embodiment, the total amount of vector according to the invention, preferably a bacteriophage genome or a phagemid according to the invention, or vector included in a delivery vehicle according to the invention, preferably a bacteriophage or a packaged phagemid according to the invention, for each administration is comprised between $10^4$ and $10^{14}$ active particles, preferably between $10^8$ and $10^{14}$ active particles, even more preferably between $10^{12}$ and $10^{14}$ active particles.

The form of the pharmaceutical or veterinary compositions, the route of administration and the dose of administration of the vector according to the invention, preferably a bacteriophage genome or a phagemid according to the invention, of the vector included in a delivery vehicle according to the invention, preferably a bacteriophage or a packaged phagemid according to the invention, or of the pharmaceutical or veterinary composition according to the invention can be adjusted by the man skilled in the art according to the type and severity of the infection, and to the patient, in particular its age, weight, sex, and general physical condition.

Kit and Use of a Kit

The invention also concerns a kit for the treatment of an infection, preferably a bacterial infection, in a subject, wherein the kit comprises a vector according to the invention, preferably a bacteriophage genome or a phagemid according to the invention, a vector included in a delivery vehicle according to the invention, preferably a bacteriophage or a packaged phagemid according to the invention, or a pharmaceutical or veterinary composition according to the invention and optionally a leaflet providing guidelines to use such a kit.

Preferably, the kit further comprises another active ingredient, preferably an antibiotic.

Optionally, the kit further comprises a helper bacteriophage and/or a satellite bacteriophage.

Particularly, the kit further comprises a helper bacteriophage and/or a satellite bacteriophage to promote the encapsidation of a vector according to the invention, preferably a bacteriophage genome or a phagemid according to the invention.

The invention also concerns the use of a kit as described above in the treatment of a disease selected from the group consisting of an infection, preferably a bacterial infection, inflammatory diseases, auto-immune diseases, cancers, and brain disorders, in a subject in need thereof. In particular, the kit as described above can be used for improving the general health of a subject, for eradicating pathogenic or virulent bacteria, for improving the effectiveness of drugs, and/or for modifying the composition of the microbiome. The kit as described above can be also used for non-therapeutic applications such as cosmetic application or for improving the well-being of a subject.

Preferably, the subject is a human.

All the references cited in this application, including scientific articles and summaries, published patent applications, granted patents or any other reference, are entirely incorporated herein by reference, which includes all the results, tables, figures and texts of theses references.

Although having different meanings, the terms "comprising", "having", "consisting in" and "containing" can be replaced one for the other in the entire application.

Further aspects and advantages of the present invention will be described in the following examples, which should be regarded as illustrative and not limiting.

EXAMPLES

Example 1

Figure 1:
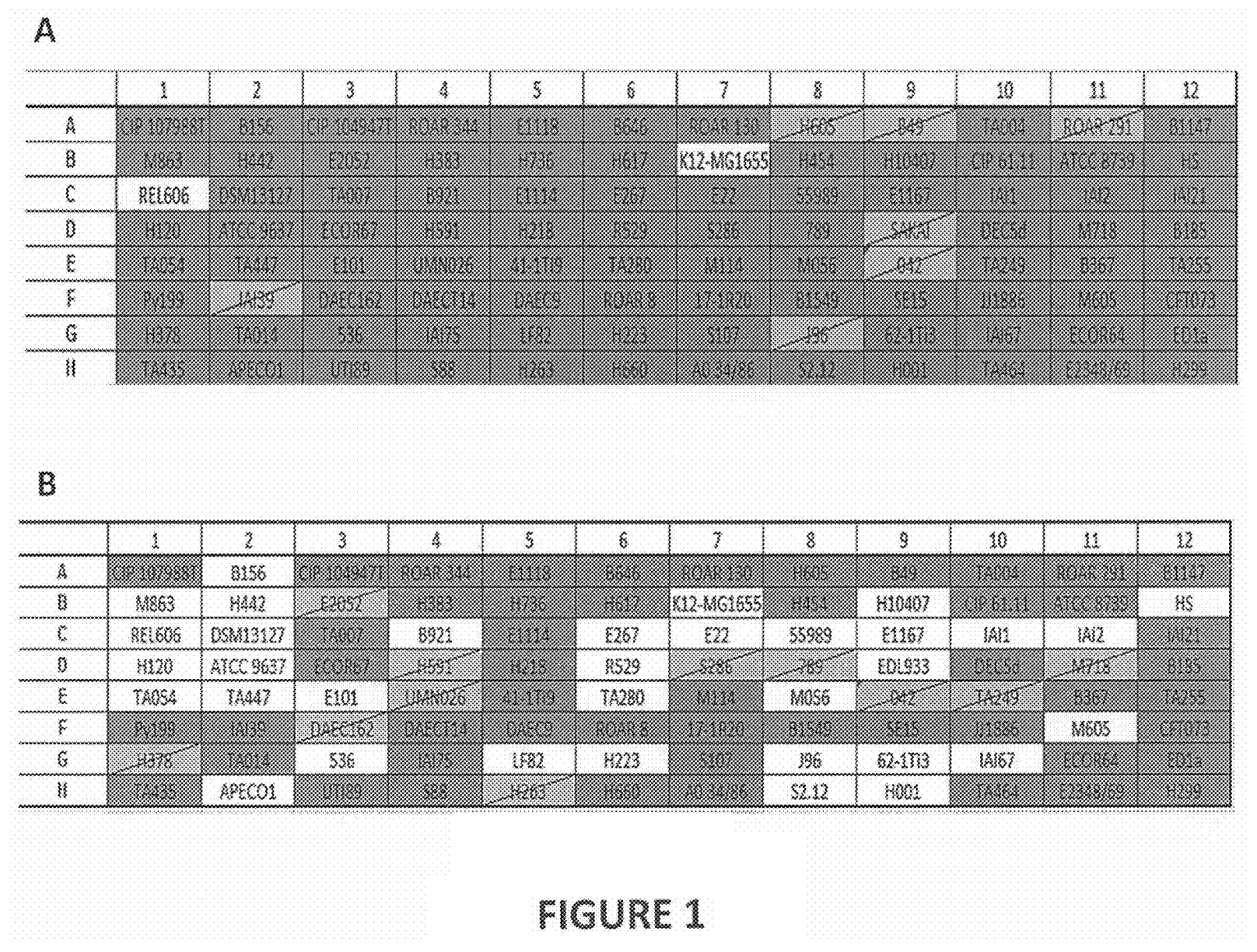

As a proof of concept, a set of different *Escherichia coli* strains was tested against infection by bacteriophage Lambda. Cells were grown overnight in liquid LB plus maltose 0.2% at 37° C. Next day, cells were diluted 1:100 in fresh liquid LB medium plus 0.2% maltose and allowed to grow at 37° C. for 2 hours. A bacterial lawn was prepared by plating 500 µL of bacterial culture onto an LB-agar plate. Purified Lambda bacteriophage particles, containing the wild-type 48.5 kb genome, was spotted on the bacterial lawn and allowed to grow at 37° C. for 18 hours. Lambda injection efficiency was assessed by the presence of plaques (FIGS. 1 A and C). Only strains K12-MG1655 and REL606 were observed to form plaques, indicating Lambda phage delivery, while no effect was observed in any other of the 89 tested strains.

Next, the inventors have tested with a packed Lambda-based phagemid whether the injection efficiency could be improved. By using phagemids of a smaller size, potential restriction sites may be avoided. For this, we constructed a 3.3 kb phagemid including the Lambda phage cos site, constitutively expressed GFP and chloramphenicol resistance genes (hereafter referred to as Lambda phagemid) and transformed it into CY2120b strain. This strain lacks the wild-type lambda cos site but otherwise possesses all the machinery for the induction of the Lambda phage lytic cycle as well as the DNA packaging system. CY2120b cells containing the Lambda phagemid were grown at 30° C. in liquid LB media. At an OD600 of 0.6, the culture was shifted to 42° C. for 25 minutes to induce the entry into lytic cycle. After that, cells were shifted back to 37° C. for 3 hours to allow for virion assembly containing the Lambda cosmid. Cells were then centrifuged and washed in Lambda buffer (10 mM Tris pH 7.5, 100 mM NaCl, 10 mM MgSO4). Chloroform was added and the sample was spun down at 17,000 g for 5 minutes. Finally, the aqueous phase was collected and filtered through a 0.2 µm pore-size filter. This phase, containing pure Lambda packaged phagemids, was used to perform a transduction assay. 95 different strains of *E. coli* were grown overnight at 37° C. in liquid LB plus 0.2% maltose and diluted 1:100 the next day in fresh LB plus maltose. After 2 hours of incubation at 37° C. 45 µL of cell culture was added to 45 µL of purified packaged phagemid and further incubated at 37° C. for 30 minutes. Finally, 10 µL of this mixture was plated on LB-agar plates containing 25 µg/mL chloramphenicol and incubated for 18 hours at 37° C. (FIGS. 1 B and C). Out of 95 strains tested, the packaged Lambda phagemid is able to inject its cargo in 34 of them, representing approximately 36% of all the strains tested.

Example 2

The inventors have tested by using six packed Lambda-based phagemids whether the removal of restriction sites within the phagemid DNA sequences improves the efficiency of the phagemid delivery and/or broadens the number of bacterial strains in which the phagemid can be delivered. For this, the inventors constructed three variants of a larger (between 7.2-8.7 kb) phagemid, hereafter referred to as Lambda phagemid 8 kb, and three variants of a smaller (between 2.9-3.3 kb) phagemid, hereafter referred to as Lambda phagemid 3 kb. The three variants of each of the two phagemids differ in the presence of the restriction sites recognized by the type I and type II restriction modification (RM) systems of *E. coli* strains. The wild type (WT) variants of Lambda phagemid 8 kb and Lambda phagemid 3 kb have not been depleted of the *E. coli* restriction sites and thus, contain multiple sequences recognized by the RM nucleases of *E. coli* strains. In contrast, DNA sequences of the restriction-free (RF) variants of Lambda phagemids 8 kb and 3 kb have been genetically re-coded in order to remove a majority of the restriction sites of *E. coli* strains. These two RF Lambda phagemids are completely depleted of the restriction sites that are known to be recognized by the RM system of a specific *E. coli* strain, hereafter referred to as Test Strain 1. Finally, the Lambda phagemid 8 kb variant "TypeI" and Lambda phagemid 3 kb variant "TypeII" each contain only a single restriction site (CACNNNNNNNCTGG (SEQ ID No: 1) and GAABCC, respectively) recognized by the type I or type II RM system of Test Strain 1.

Both Lambda phagemid 8 kb and Lambda phagemid 3 kb comprise the pi 5a origin of replication, Lambda phage cos site and constitutively expressed chloramphenicol resistance gene. Lambda phagemid 8 kb additionally contains the small guide RNA scaffold sequence and the cas9 and phlF genes.

The six Lambda phagemids were transformed into CYC3 strain. This strain lacks the wild-type lambda cos site but otherwise possesses all the machinery for the induction of the Lambda phage lytic cycle as well as the DNA packaging system. CYC3 cells containing the individual Lambda phagemids were grown at 30° C. in liquid LB media. At an OD600 of 0.7, the CYC3 cultures were shifted to 42° C. for 30 minutes to induce the entry into lytic cycle. After that, cells were shifted back to 37° C. for 3 hours to allow for assembly of virions that contain the Lambda phagemids. Cells were then centrifuged and washed in Lambda buffer (10 mM Tris pH 7.5, 100 mM NaCl, 10 mM MgSO4). Chloroform was added and the sample was spun down at 17,000 g for 5 minutes. Finally, the aqueous phase was collected and filtered through a 0.2 µm pore-size filter. This phase, containing pure Lambda packaged phagemids, was used to perform transduction assays with Test Strain I and/or with the collection of 96 different strains of *E. coli*.

The strains of *E. coli* were grown overnight at 37° C. in liquid LB and diluted 1:60 or 1:100 the next day in fresh LB plus 0.2% maltose plus 5 mM $CaCl_2$. After 2.5 hours of incubation at 37° C. in case of the collection of 96 different strains or after the culture of Test Strain I reached optical density of 2.5, the transduction assays were performed.

To verify if the presence of a single restriction site that is either recognized by the type I or type IIRM nucleases affects the frequency of the phagemid delivery, Test Strain I has been transduced with four Lambda phagemids: i) 8 kb TypeI; ii) 8 kb RF; iii) 3 kb TypeII and 3 kb RF. 50 µL of the non-diluted culture of Test Strain I was mixed with 50 µL of the purified phagemids, which were either non-diluted or diluted between $10^{(-1)}$ and $10^{(-8)}$ in LB plus 5 mM $CaCl_2$. The phagemid:bacteria mixtures were incubated at 37° C. for 30 minutes, with shaking. Finally, 10 µL of these mixtures was placed on LB-agar plates containing 25 µg/mL chloramphenicol. The plates were tilted in order to allow each 10 µL droplet to run down the LB-agar surface, forming a streak. The LB-agar plates were incubated for 18 hours at 37° C. The colony forming units (CFUs) were quantified for the streaks with the phagemid dilutions that gave the highest number of individual countable colonies (FIG. 2).

The CFUs correspond to the number of Test Strain I cells to which phagemids were successfully transduced. To assess efficiencies of the delivery of the four phagemids in Test Strain I, the obtained CFU numbers were normalized against the total titer of each phagemid (Table 3). The total titers of the phagemids were parallelly assessed by transducing the *E. coli* strain MG1655 that is permissive for the phagemids tested. The efficiencies of the delivery of the Lambda phagemids 8 kb and 3 kb RF were compared to the efficiencies of the delivery of Lambda phagemid 8 kb TypeI and Lambda phagemid 3 kb TypeII, respectively (Table 3). Lambda phagemids 8 kb RF and 3 kb RF, which are deprived of the restriction sites recognized by the RM nucleases of Test Strain 1, were delivered 3-5 log and 1-2 log more efficiently in Test Strain 1 than the Lambda phagemids 8 kb TypeI and 3 kb TypeII, which contain single restriction sites for the type I and type II RM system, respectively. These results indicate that the removal of the restriction sites recognized by the RM systems of the specific strain improves the phagemid delivery efficiency. Moreover, even the presence of only one additional restriction site within the phagemid DNA sequence can significantly reduce its delivery into a bacterial strain.

Figure 3:
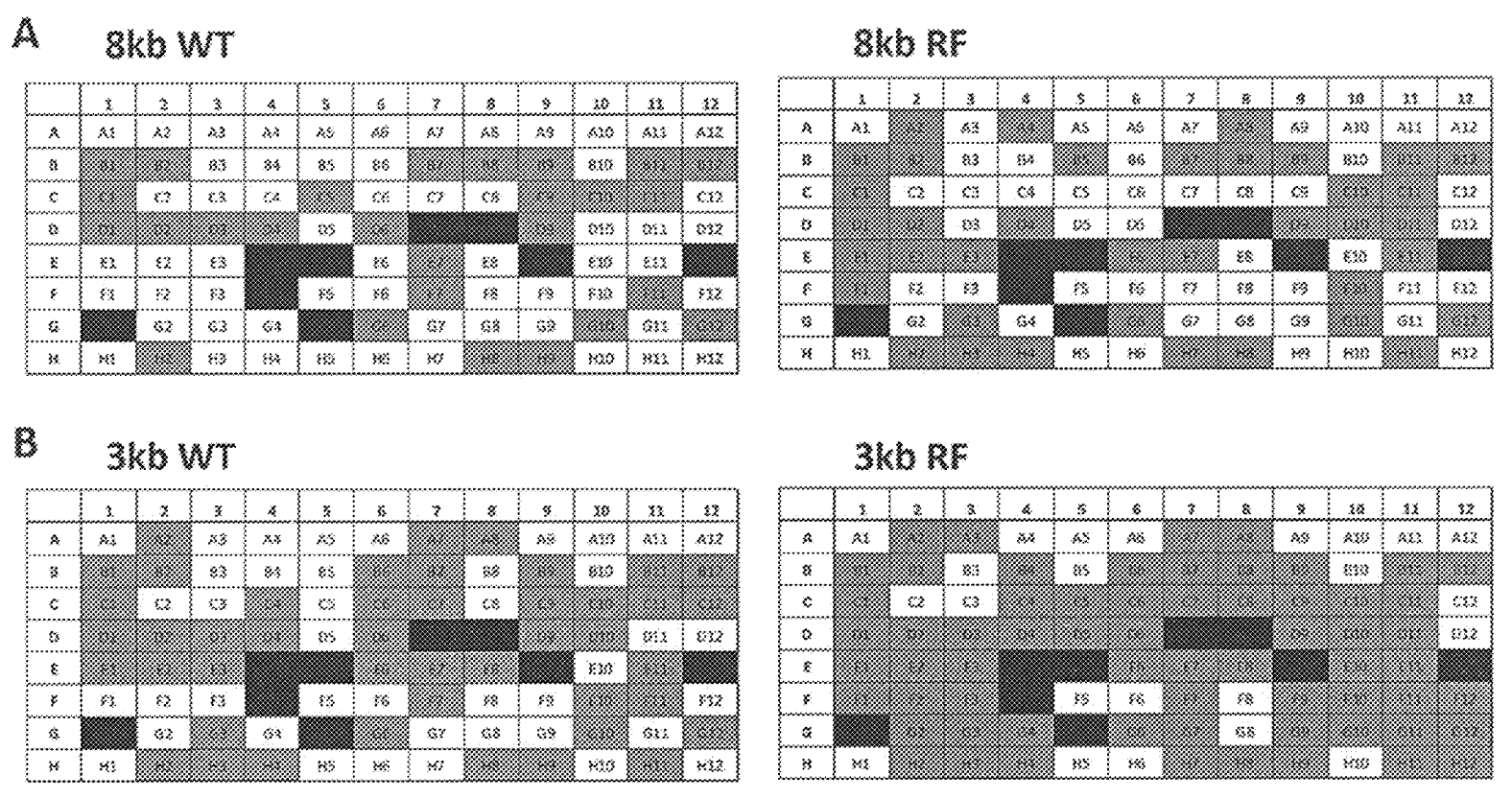

The inventors verified whether removing multiple restriction sites, which are recognized by various RM nucleases of different strains of *E. coli*, from the phagemid DNA sequence improves the efficiency of the phagemid delivery and/or broadens the number of strains in which phagemid can be delivered. For this, the collection of 87 different strains of *E. coli* was transduced with four Lambda phagemids: i) 8 kb WT; ii) 8 kb RF; iii) 3 kb WT and 3 kb RF. 90 μL of the non-diluted cultures of the 87 strains was mixed with 10 μL of the purified phagemids. The phagemid: bacteria mixtures were incubated at 37° C. for 30 minutes, with shaking. Finally, 10 μL of these mixtures was spotted on LB-agar plates containing 25 μg/mL chloramphenicol. The growth of the 87 spotted strains of *E. coli*, which indicates the successful phagemid delivery, was assessed after an 18-hour-long incubation of the plates at 37° C. (FIG. 3, Table 4). Lambda phagemid 8 kb RF, depleted of multiple *E. coli* restriction sites, was transduced to 38 out of 87 strains tested, representing approximately 44% of all the strains tested (Table 2, FIG. 2). In comparison, packaged Lambda phagemid 8 kb WT, with unreduced number of restriction sites, was transduced to 27 (31%) of the strains tested. Similarly, Lambda phagemid 3 kb RF was transduced to a higher number (64) of the *E. coli* strains tested, which represents 74% of the tested strains when compared to Lambda phagemid 3 kb WT (45 strains; 52%). The higher numbers of the strains growing after the transductions with the RF variants of phagemids indicates that the removal of multiple restriction sites broadens the number of strains in which the two phagemid are delivered (Table 4, FIG. 3).

TABLE 3

Titers of Lambda Phagemids (per ml of phagemid stock): i) 8kb TypeI; ii) 8kb RF; iii) 3kb TypeII; iv) 3kb RF. Titers were calculated based on the colony forming units (CFUs) obtained after transductions to the permissive control strain, *E. coli* strain MG1655 (Total Titer) and to Test Strain I. For each phagemid, the values obtained from two independent experiments are shown. The efficiencies of transductions to Test Strain I are increased for the restriction-free (RF) phagemid variants when compared to the corresponding variants containing a single TypeI or TypeII restriction site.

| Lambda Phagemid | Total Titer | Test Strain I |
|---|---|---|
| 8kb TypeI | $8*10^9$ | $2*10^3$ |
|  | $3*10^9$ | $2*10^1$ |
| 8kb RF | $2*10^{10}$ | $2*10^7$ |
|  | $2*10^{10}$ | $2*10^7$ |
| 3kb TypeII | $1*10^9$ | $6*10^4$ |
|  | $8*10^8$ | $8*10^3$ |
| 3kb RF | $9*10^9$ | $2*10^6$ |
|  | $1*10^9$ | $1*10^6$ |

TABLE 4

Number of strains of *E. coli* that exhibited growth (lawns or more than ten colonies visible per spot plated) after transductions with Lambda phagemids: 8kb WT, 8 kb RF, 3kb WT and 3kb RF. Bacterial growth indicates delivery of the phagemid in the specific strain. In total 87 strains of *E. coli* were tested for the phagemid delivery.

| Lambda Phagemid | No. of growing strains | % of the strains tested |
|---|---|---|
| 8kb WT | 27 | 31% |
| 8kb RF | 38 | 44% |
| 3kb WT | 45 | 52% |
| 3kb RF | 64 | 74% |

What is claimed:

1. A method for delivering an engineered vector into a group of bacteria of interest in a subject, wherein the method comprises administering to the subject an engineered vector, thereby delivering said engineered vector to a bacterium of said group of bacteria of interest, wherein said engineered vector is an engineered bacteriophage, packaged phagemid, bacteriophage genome or phagemid, which has been genetically engineered to remove, in non-coding regions and optionally in coding regions, at least one restriction site of at least one restriction enzyme which is frequently encoded in said group of bacteria of interest, wherein said at least one restriction site is removed by changing the sequence so as to prevent the recognition by the corresponding restriction enzyme and wherein the efficiency of DNA delivery into the group of bacteria by the engineered vector is increased as compared to DNA delivery into the group of bacteria by the engineered vector prior to removal of the at least one restriction site.

2. The method according to claim 1, wherein said bacteria of interest are Gram-negative bacteria.

3. The method according to claim 1, wherein said bacteria of interest are Gram-positive bacteria.

4. The method according to claim 1, wherein at least 10% of the bacteria of said group of interest encode said at least one restriction enzyme.

5. The method according to claim 1, wherein said vector has been genetically engineered to remove, in non-coding regions and optionally in coding regions, all the restriction sites of said at least one restriction enzyme.

6. The method according to claim 1, wherein said vector has been genetically engineered to remove, in non-coding regions and optionally in coding regions, all the restriction sites of all the restriction enzymes which are frequently encoded in said group of bacteria of interest.

7. The method according to claim 1, wherein at least 10% of the restriction sites originally present in the vector have been removed.

8. The method according to claim 1, wherein said bacteria of interest are selected from the group consisting of *Yersinia* spp., *Escherichia* spp., *Klebsiella* spp., *Acinetobacter* spp., *Pseudomonas* spp., *Helicobacter* spp., 17*brio* spp, *Salmonella* spp., *Streptococcus* spp., *Staphylococcus* spp., *Fusobacterium* spp., *Bacteroides* spp., *Clostridium* spp., *Cutibacterium* spp., *Shigella* spp., *Enterococcus* spp., *Enterobacter* spp., and *Listeria* spp.

9. The method according to claim 1, wherein said group of bacteria of interest is selected from the group consisting of *E. coli*, *E. coli* STEC, *Neisseria gonorrhoeae*, *Neisseria meningitides*, *Salmonella enteritidis*, *Streptococcus pneumoniae*, *Streptococcus pyogenes*, *Vibrio cholera*, *Haemophilus influenza*, *Klebsiella pneumoniae*, *Pseudomona aerigunosa*, *Staphylococcus aureus*, *Vibrio cholera*, *Brucella suis*, *Mycobacterium tuberculosis*, *Enterobacter cloacae*, *Bacillus cereus*, *Corynebacterium diphtheria*, *Campylobacter jejuni*, *Listeria monocytogenes*, *Campylobacter coli*, *Bacillus thuringiensis*, *Yersinia enterocolitica*, *Helicobacter pylori*, *Bacteroides fragilis*, *Clostridium butyricum*, *Streptococcus agalactiae*, *Leuconostoc lactis*, *Shigella sonnei*, *Zymomonas mobilis*, *Treponema denticola*, *Lactobacillus plantarum*, *Enterococcus faecium*, *Bacillus liquefaciens*, *Staphylococcus epidermidis*, *Serratia marcescens*, *Citrobacter freundii*, *Parvimonas micra*, *Prevotella intermedia*, *Brucella melitensis*, *Aeromonas caviae*, *Clostridium botulinum*, *Clostridium perfringens*, *Mycoplasma pneumonia*, *Salmonella typhimurium*, *Salmonella paratyphi*, *Shigella flexnerii*, *Vibrio parahaemolyticus*, *Yersinia pseudotuberculosis*, *Actinobacter baumanii*, *Bacteroides distasonis*, *Clostridium leptum*, *Brevibacterium lactofermentum*, *Actinobacillus actinobycetemcomitans*, *Selnomonas ruminatium*, *Mycoplasma mycoides*, *Staphilococcus lugdunensis*, *Lactobacillus rhamnosus*, *Lactobacillus casei*, *Lactobacillus acidophilus*, *Bacillus coagulans*, *Pyrococcus abyssi*, *Selenomonas nominantium*, *Streptococcus ferus*, *Streptomyces phaechromo* genes, *Streptomyces ghanaenis*, *Enterobacter aerogenes*, *Morganella morganii*, *Fusobacterium nucleatum*, *Porphyromonas endodontalis*, *Porphyromonas gin givalis,Micrococcus luteus*, *Aeromonas hydrophila*, *Bacillus anthracis*, *Bartonella henselae*, *Bordetella pertussis*, *Borrelia garinii*, *Brucella canis*, *Campylobacter fetus*, *Clostridium tetani*, *Francisella tularensis*, *Legionella pneumophila*, *Leptospira interrogans*, *Leptospira santarosai*, *Leptospira weilii*, *Mycobacterium leprae*, *Shigella dysenteriae*, *Staphylococcus saprophyticus*, *Streptococcus viridans*, *Treponema pallidum*, *Ureaplasma urealyticum*, *Yersinia pestis* and *Propionibacterium acnes* and the vector has been genetically engineered to remove at least one restriction site selected from the group of restriction sites consisting of the sequences SEQ ID NO: 1, SEQ ID NO: 2, SEQ ID NO: 4, SEQ ID NO: 3, SEQ ID NO: 36, SEQ ID NO: 37, SEQ ID NO: 34, SEQ ID NO: 80, GGTCTC, ACCACC, GAACC and CACAG when the group of bacteria of interest is *E. coli*; the sequences SEQ ID NO: 6, SEQ ID NO: 1, SEQ ID NO: 37, SEQ ID NO: 34 and SEQ ID NO: 79 when the group of bacteria of interest is *E. coli* STEC; the sequences SEQ ID NO: 81, SEQ ID NO: 82, GGCC, GGNNCC, GGTGA, GCCGGC, SEQ ID NO: 83, RGCGCY, CCGCGG, GCSGC, CCGG, CCACC, and AGAAA when the group of bacteria of interest is *Neisseria gonorrhoeae*, the sequences GGNNCC, GCGCGC, CCGG, RCCGGY, CCTTC, CCAGA, GACGC and ACACC when the group of bacteria of interest is *Neisseria meningitides*; the sequences SEQ ID NO: 84-88, GATCAG, GGWCC, CGGCCG and CAGAG when the group of bacteria of interest is *Salmonella enteritidis*; the sequence TCTAGA when the group of bacteria of interest is *Streptococcus pneumoniae*; the sequences SEQ ID NO: 89-91 when the group of bacteria of interest is *Streptococcus pyogenes*, the sequence SEQ ID NO: 02 when the group of bacteria of interest is *Vibrio cholera*; the sequences RGCGCY, CGCG, AAGCTT, GCGC, GTYRAC, and GTCGAC when the group of bacteria of interest is *Haemophilus influenza*; the sequences SEQ ID NO: 93-96 and CGCATC when the group of bacteria of interest is *Klebsiella pneumoniae*; the sequences SEQ ID NO: 97-99, GTCGAC, CTCGAG, CTGCAG and GGCGCC when the group of bacteria of interest is *Pseudomonas aerigunosa*; the sequences SEQ ID NO: 100-102, CCNGG, GCNGC and GGNCC when the group of bacteria of interest is *Staphylococcus aureus*; the sequence SEQ ID NO: 103 when the group of bacteria of interest is *Vibrio cholera*; the sequences CTCGAG and GACGAG when the group of bacteria of interest is *Brucella suis*; the sequences SEQ ID NO: 104 and CACGCAG when the group of bacteria of interest is *Mycobacterium tuberculosis*; the sequence GTCGAC when the group of bacteria of interest is *Enterobacter cloacae*; the sequences GCNGC, GCSGC, ACGGC and CACAG when the group of bacteria of interest is *Bacillus cereus*; the sequence GCGGAG when the group of bacteria of interest is *Corynebacterium diphtheria*; the sequences SEQ ID NO: 105-108 and GKAAYG, when the group of bacteria of interest is *Campylobacter jejuni*; the sequences SEQ ID NO: 109-112, TAGRAG, GTATCC and GTCGAC when the group of bacteria of interest is *Listeria monocytogenes*; the sequence SEQ ID NO: 113 when the group of bacteria of interest is *Campylobacter coli*; the sequences GGWCC and ACGGC when the group of bacteria of interest is *Bacillus thuringiensis*; the sequences GGCGCC and GCGCGC when the group of bacteria of interest is *Yersinia enterocolitica*; the sequences CCGG, GTNNAC, GTAC, CATG, TCNNGA, TGCA, GANTC, ACNGT, ACGT, CCATC, CCTC, CTNAG, GAAGA, GTSAC, CCNNGG, GAATTC, GGCC, TCNGA, CCTTC, CTGCAG and TCAG when the group of bacteria of interest is *Helicobacter pylori*; the sequences SEQ ID NO: 114, CCTTC, GGNNCC, GCGCGC, CCGG, RCCGGY, CCAGA, GACGC and ACACC when the group of bacteria of interest is *Neisseria meningitides*; the sequences SEQ ID NO: 115-121 and TCTAGA when the group of bacteria of interest is *Streptococcus pneumoniae*; the sequences SEQ ID NO: 89-91 and CCNGG when the group of bacteria of interest is *Streptococcus pyogenes*; the sequences SEQ ID NO: 92, CTGCAG, TCCGGA, GGCGCC, CTCGAG and GGNCC when the group of bacteria of interest is *Vibrio cholera*; the sequences SEQ ID NO: 122-124, RGCGCY, CGCG, AAGCTT, GCGC, GTYRAC, GTCGAC, CGAG, AGAAA, ACAGC and CGAAT when the group of bacteria of interest is *Haemophilus influenza*; the sequences SEQ ID NO: 97-99, SEQ ID NO: 125-131, GTCGAC, CTCGAG, CTGCAG, GGCGCC, ACGACC and GCCCAG when the group of bacteria of interest is *Pseudomonas aerigunosa*; the sequences SEQ ID NO: 100-102, CCNGG, GCNGC, GGNCC, SEQ ID NO: 132-133 and GCTGA when the group of bacteria of interest is *Staphylococcus aureus*; the sequences SEQ ID NO: 134-135, CTCGAG and GACGAG when the group of bacteria of interest is *Brucella suis*; the sequences SEQ ID NO: 104, CACGCAG and SEQ ID NO: 136 when the group of bacteria of interest is *Mycobacterium tuberculosis*; the sequences SEQ ID NO: 137-140, GTCGAC and ACGAAG when the group of bacteria of interest is *Enterobacter cloacae*; the sequences SEQ ID NO: 141-147, GCNGC, GCSGC, GCWGC, ACGGC, CTCGAG and CACAG when the group of bacteria of interest is *Bacillus cereus*; the sequences SEQ ID NO: 148-152 and GCGGAG when the group of bacteria of interest is *Corynebacterium diphtheria*; the sequences SEQ ID NO: 105-108, CATG and GKAAYG when the group of bacteria of interest is *Campylobacter jejuni*; the sequences SEQ ID NO: 109-110, SEQ ID NO: 112, SEQ ID NO: 153-155, TAGRAG, GTATCC, GTCGAC and ACANNNNCATC when the group of bacteria of interest is *Listeria monocytogenes*; the sequences SEQ ID NO: 156, GGWCC, ACGGC, GCNGC, GGWCC, ACGGC, GCNGC and CACAG when the group of bacteria of interest is *Bacillus thuringiensis*; the sequences GGCGCC, GCGCGC and CCGAG when the group of bacteria of interest is *Yersinia enterocolitica*; the sequences SEQ ID NO: 157-164, CCGG, GTNNAC, CATG, GTAC, TCNNGA, GANTC, TGCA, ACNGT, ACGT, CCATC, CCTC, CTNAG, GAAGA, CCNNGG, GTSAC, GAATTC, GGCC, TCNGA, CCTTC, CTGCAG and TCAG when the group of bacteria of interest is *Helicobacter pylori*; the sequences SEQ ID NO: 165 and ATGCAT when the group of bacteria of interest is *Bacteroides fragilis*; the sequences SEQ ID NO: 166, GCNGC and GCTNAGC when the group of bacteria of interest is *Clostridiium butyricum*; the sequences SEQ ID NO: 167, GGNCC, GGCC and CCGG when the group of bacteria of interest is *Streptococcus agalactiae*; the sequences CAANNNNNNNNTAYG, TNAGCC, CCNGG, GCNGC and CCCGC when the group of bacteria of interest is *Leuconostoc lactis*; the sequences SEQ ID NO: 168-169, CTGCAG, CCNGG, GACGTC, GAATTC and GTCGAC when the group of bacteria of interest is *Shigella sonnei*; the sequences SEQ ID NO: 170-172 and GATATC when the group of bacteria of interest is *Zymomonas mobilis*; the sequence SEQ ID NO: 173 when the group of bacteria of interest is *Treponema denticola*; the sequences SEQ ID NO: 174-75, GGNCC, CTCTTC, GCATC, GCSGC and CGRYCG when the group of bacteria of interest is *Lactobacillus plantarum*; the sequences SEQ ID NO: 176-177, CCGG, CCWWGG and GCWGC when the group of bacteria of interest is *Enterococcus faecium*; the sequences SEQ ID NO: 178-179, ATCGAT, GCWGC, GCNGC, GCGCGC, GGATC and GGGAC when the group of bacteria of interest is *Bacillus liquefaciens*; the sequences SEQ ID NO: 180-182, GGTGA and CCTC when the group of bacteria of interest is *Staphylococcus epidermidis*; the sequences SEQ ID NO: 183-186, GCNGC, CTGCAG, CCCGGG, GCCGC, CCGCGG and CAGAG when the group of bacteria of interest is *Serratia marcescens*; the sequences SEQ ID NO: 187-190 and CGATCG when the group of bacteria of interest is *Citrobacter freundii*; the sequences SEQ ID NO: 191, GGCC, GCGATG, GTCGAC, CCGG and GCNGC when the group of bacteria of interest is *Parvimonas micra*; the sequences SEQ ID NO: 192-200, GGATG and GCCGGC when the group of bacteria of interest is *Prevotella intermedia*; the sequences SEQ ID NO: 201-202, GCWGC, TGATCA and CACAG when the group of bacteria of interest is *Brucella melitensis*; the sequences SEQ ID NO: 203, CTGCAG, CRRTAAG, CCGG, GTCGAC and GCYYGAC when the group of bacteria of interest is *Aeromonas caviae*; the sequences SEQ ID NO: 204-209, GRCGYC, GCWGC, GCSGC, CCGG and GCNGC when the group of bacteria of interest is *Clostridium botulinum*; the sequences SEQ ID NO: 210-211, GCNGC, GGWCC, GTCTC, GGCC, ACGGC and VGACAT when the group of bacteria of interest is *Clostridium perfringens*; the sequences SEQ ID NO: 212-213, CCGG, CCWWGG and GCWGC when the group of bacteria of interest is *Enterococcus faecium*; the sequence SEQ ID NO: 214 when the group of bacteria of interest is *Mycoplasma pneumonia*; the sequences SEQ ID NO: 215-217, GATCAG, CCNGG, CCWWGG and CAGAG when the group of bacteria of interest is *Salmonella typhimurium*; the sequences SEQ ID NO: 218-219, GGNCC, GGATG, CWTCCAG, GCSGC, GTCGAC, GTCGAC and GCATC when the group of bacteria of interest is *Salmonella paratyphi*; the sequences SEQ ID NO: 220, CTGCAG and GCCGGC when the group of bacteria of interest is *Shigella flexnerii*; the sequences SEQ ID NO: 221, CCNGG, CTCTTC and GNAATC when the group of bacteria of interest is *Vibrio parahaemolyticus*; the sequences SEQ ID NO: 222, CTGCAG and CGGAAG when the group of bacteria of interest is *Yersinia pseudotuberculosis*; the sequences SEQ ID NO: 223-230, GAAAGC and CGAGG when the group of bacteria of interest is *Actinobacter baumanii*; the sequences GGCGCC, GCCGGC and CACAG when the group of bacteria of interest is *Bacteroides distasonis*; the sequences GGNCC and GGATG when the group of bacteria of interest is *Clostridium leptum*; the sequences GCWGC, GCTNAGC and CACAG when the group of bacteria of interest is *Brevibacterium lactofermentum*; the sequences CCGG, CCGCGG, GATATC, CGGCCG and CTCGAG when the group of bacteria of interest is *Actinobacillus actinobycetemcomitans*; the sequences GCCGGC, CCGCGG and GAGAG when the group of bacteria of interest is *Selnomonas ruminatium*; the sequences TCTAGA, GGNCC, CCTC, CCATC, GANTC, CCTTC, GCATC and TGAG when the group of bacteria of interest is *Mycoplasma mycoides*; the sequence GGCGCC when the group of bacteria of interest is *Staphilococcus lugdunensis*; the sequence GATATC when the group of bacteria of interest is *Lactobacillus rhamnosus*; the sequences CCGCGG, CTGCAG and GATATC when the group of bacteria of interest is *Lactobacillus casei*; the sequence GGCC when the group of bacteria of interest is *Lactobacillus acidophilus*; the sequences ATCGAT, GRCGYC, GCSGC, CTGCAG, GTCTC, GGATCC, GAGCTC, CTCGAG, CACAG, GAWTC and TAAATC when the group of bacteria of interest is *Bacillus coagulans*; the sequences GTAC and CCGGNAG when the group of bacteria of interest is *Pyrococcus abyssi*; the sequences GGCCGAG and CCGG when the group of bacteria of interest is *Selenomonas nominantium*; the sequence CTRYAG when the group of bacteria of interest is *Streptococcus ferus*; the sequences CCNGG, GCATGC, TTAA, GTAC and CTAG when the group of bacteria of interest is *Streptomyces phaechromo* genes; the sequence GCCGGC when the group of bacteria of interest is *Streptomyces ghanaenis*; the sequences YGGCCR and GGNCC when the group of bacteria of interest is *Enterobacter aerogenes*; the sequences GGNNCC, CGATCG, TGCA and GCSGC when the group of bacteria of interest is *Morganella morganii*; the sequences GGCC, AAGCTT, ATGCAT and GCGC when the group of bacteria of interest is *Fusobacterium nucleatum; the sequences GCAGT, GAGTC and GATATC when the group of bacteria of interest is Porphyromonas endodontalis*; the sequence GAATTC when the group of bacteria of interest is *Porphyromonas gingivalis*; the sequences ACGCGT, GAGCTC and CAGNNNCTG when the group of bacteria of interest is *Micrococcus luteus*; the sequences CTCGAG, GCYYGAC, YAAMGAG and CAGCTG when the group of bacteria of interest is *AEromonas hydrophila*; the sequences RTCAGG and GGWCC when the group of bacteria of interest is *Bacillus anthracis*; the sequence AGTACT when the group of bacteria of interest is *Bartonella henselae*; the sequences GGNCC, CTGCAG, GRCGYC and AGCCGCC when the group of bacteria of interest is *Brodetella pertussis*; the sequence CCGG when the group of bacteria of interest is *Borrelia garinii*; the sequences CCATC, GGCGCC, CTNAG, GGNCC and GCCGGC when the group of bacteria of interest is *Brucella canis*; the sequence SEQ ID NO: 37 when the group of bacteria of interest is *Campylobacter fetus*; the sequences CGATCG, CCCGGG and GCCGGC when the group of bacteria of interest is *Clostridium tetani*; the sequences GGCC and CTGCAG when the group of bacteria of interest is *Francisella tularensis*; the sequences CCDG and GGNCC when the group of bacteria of interest is *Legionella pneumophila*; the sequences GCGC and GGCC when the group of bacteria of interest is *Leptospira interrogans*; the sequences RGATCY, GCWGC, CCATC, GTATCC and CTAG when the group of bacteria of interest is *Leptospira santarosai*; the sequence GTCGAC when the group of bacteria of interest is *Leptospira weilii*; the sequences GGNCC, GCATC and GTCGAC when the group of bacteria of interest is *Mycobacterium leprae*; the sequences SEQ ID NO: 37, CCNGG, GAATTC, GGCC and GGGAC when the group of bacteria of interest is *Shigella dysenteriae*; the sequences GCNGC and ACGT when the group of bacteria of interest is *Staphylococcus saprophyticus*; the sequence GCCGGC when the group of bacteria of interest is *Streptococcus viridans*; the sequences GGWCC, TCGA and GMGAGC when the group of bacteria of interest is *Treponema pallidum*; the sequence GCNGC when the group of bacteria of interest is *Ureaplasma urealyticum*; and the sequences SEQ ID NO: 231-233, AGCAGY and ACCAGG when the group of bacteria of interest is *Propionibacterium acnes*.

10. The method according to claim 1, wherein the vector has been genetically engineered to remove the restriction sites of sequences SEQ ID NO: 1, SEQ ID NO: 2, SEQ ID NO: 4, SEQ ID NO: 3, SEQ ID NO: 36, SEQ ID NO: 37, SEQ ID NO: 34, SEQ ID NO: 80, GGTCTC, ACCACC, GAACC and CACAG when the group of bacteria of interest is *E. coli*; of sequences SEQ ID NO: 6, SEQ ID NO: 1, SEQ ID NO: 37, SEQ ID NO: 34 and SEQ ID NO: 79 when the group of bacteria of interest is *E. coli* STEC; of sequences SEQ ID NO: 81, SEQ ID NO: 82, GGCC, GGNNCC, GGTGA, GCCGGC, SEQ ID NO: 83, RGCGCY, CCGCGG, GCSGC, CCGG, CCACC, and AGAAA when the group of bacteria of interest is *Neisseria gonorrhoeae*, of sequences GGNNCC, GCGCGC, CCGG, RCCGGY, CCTTC, CCAGA, GACGC and ACACC when the group of bacteria of interest is *Neisseria meningitides*; of sequences SEQ ID NO: 84-88, GATCAG, GGWCC, CGGCCG and CAGAG when the group of bacteria of interest is *Salmonella enteritidis*; of sequence TCTAGA when the group of bacteria of interest is *Streptococcus pneumoniae*; of sequences SEQ ID NO: 89-91 when the group of bacteria of interest is *Streptococcus pyogenes*, of sequence SEQ ID NO: 02 when the group of bacteria of interest is *Vibrio cholera*; of sequences RGCGCY, CGCG, AAGCTT, GCGC, GTYRAC, and GTCGAC when the group of bacteria of interest is *Haemophilus influenza*; of sequences SEQ ID NO: 93-96 and CGCATC when the group of bacteria of interest is *Klebsiella pneumoniae*; of sequences SEQ ID NO: 97-99, GTCGAC, CTCGAG, CTGCAG and GGCGCC when the group of bacteria of interest is *Pseudomonas aerigunosa*; of sequences SEQ ID NO: 100-102, CCNGG, GCNGC and GGNCC when the group of bacteria of interest is *Staphylococcus aureus*; of sequence SEQ ID NO: 103 when the group of bacteria of interest is *Vibrio cholera*; of sequences CTCGAG and GACGAG when the group of bacteria of interest is *Brucella suis*; of sequences SEQ ID NO: 104 and CACGCAG when the group of bacteria of interest is *Mycobacterium tuberculosis*; of sequence GTCGAC when the group of bacteria of interest is *Enterobacter cloacae*; of sequences GCNGC, GCSGC, ACGGC and CACAG when the group of bacteria of interest is *Bacillus cereus*; of sequence GCGGAG when the group of bacteria of interest is *Corynebacterium diphtheria*; of sequences SEQ ID NO:

105-108 and GKAAYG when the group of bacteria of interest is *Campylobacter jejuni*; of sequences SEQ ID NO: 109-112, TAGRAG, GTATCC and GTCGAC when the group of bacteria of interest is *Listeria monocytogenes*; of sequence SEQ ID NO: 113 when the group of bacteria of interest is *Campylobacter coli*; of sequences GGWCC and ACGGC when the group of bacteria of interest is *Bacillus thuringiensis*; of sequences GGCGCC and GCGCGC when the group of bacteria of interest is *Yersinia enterocolitica*; of sequences CCGG, GTNNAC, GTAC, CATG, TCNNGA, TGCA, GANTC, ACNGT, ACGT, CCATC, CCTC, CTNAG, GAAGA, GTSAC, CCNNGG, GAATTC, GGCC, TCNGA, CCTTC, CTGCAG and TCAG when the group of bacteria of interest is *Helicobacter pylori*; of sequences SEQ ID NO: 114, CCTTC, GGNNCC, GCGCGC, CCGG, RCCGGY, CCAGA, GACGC and ACACC when the group of bacteria of interest is *Neisseria meningitides*; of sequences SEQ ID NO: 115-121 and TCTAGA when the group of bacteria of interest is *Streptococcus pneumoniae*; of sequences SEQ ID NO: 89-91 and CCNGG when the group of bacteria of interest is *Streptococcus pyogenes*; of sequences SEQ ID NO: 92, CTGCAG, TCCGGA, GGCGCC, CTCGAG and GGNCC when the group of bacteria of interest is *Vibrio cholera*; of sequences SEQ ID NO: 122-124, RGCGCY, CGCG, AAGCTT, GCGC, GTYRAC, GTCGAC, CGAG, AGAAA, ACAGC and CGAAT when the group of bacteria of interest is *Haemophilus influenza*; of sequences SEQ ID NO: 97-99, SEQ ID NO: 125-131, GTCGAC, CTCGAG, CTGCAG, GGCGCC, ACGACC and GCCCAG when the group of bacteria of interest is *Pseudomonas aerigunosa*; of sequences SEQ ID NO: 100-102, CCNGG, GCNGC, GGNCC, SEQ ID NO: 132-133 and GCTGA when the group of bacteria of interest is *Staphylococcus aureus*; of sequences SEQ ID NO: 134-135, CTCGAG and GACGAG when the group of bacteria of interest is *Brucella suis*; of sequences SEQ ID NO: 104, CACGCAG and SEQ ID NO: 136 when the group of bacteria of interest is *Mycobacterium tuberculosis*; of sequences SEQ ID NO: 137-140, GTCGAC and ACGAAG when the group of bacteria of interest is *Enterobacter cloacae*; of sequences SEQ ID NO: 141-147, GCNGC, GCSGC, GCWGC, ACGGC, CTCGAG and CACAG when the group of bacteria of interest is *Bacillus cereus*; of sequences SEQ ID NO: 148-152 and GCGGAG when the group of bacteria of interest is *Corynebacterium diphtheria*; of sequences SEQ ID NO: 105-108, CATG and GKAAYG when the group of bacteria of interest is *Campylobacter jejuni*; of sequences SEQ ID NO: 109-110, SEQ ID NO: 112, SEQ ID NO: 153-155, TAGRAG, GTATCC, GTCGAC and ACANNNNCATC when the group of bacteria of interest is *Listeria monocytogenes*; of sequences SEQ ID NO: 156, GGWCC, ACGGC, GCNGC, GGWCC, ACGGC, GCNGC and CACAG when the group of bacteria of interest is *Bacillus thuringiensis*; of sequences GGCGCC, GCGCGC and CCGAG when the group of bacteria of interest is *Yersinia enterocolitica*; of sequences SEQ ID NO: 157-164, CCGG, GTNNAC, CATG, GTAC, TCNNGA, GANTC, TGCA, ACNGT, ACGT, CCATC, CCTC, CTNAG, GAAGA, CCNNGG, GTSAC, GAATTC, GGCC, TCNGA, CCTTC, CTGCAG and TCAG when the group of bacteria of interest is *Helicobacter pylori*; of sequences SEQ ID NO: 165 and ATGCAT when the group of bacteria of interest is *Bacteroides fragilis*; of sequences SEQ ID NO: 166, GCNGC and GCTNAGC when the group of bacteria of interest is *Clostridiium butyricum*; of sequences SEQ ID NO: 167, GGNCC, GGCC and CCGG when the group of bacteria of interest is *Streptococcus agalactiae*; of sequences CAANNNNNNNNTAYG, TNAGCC, CCNGG, GCNGC and CCCGC when the group of bacteria of interest is *Leuconostoc lactis*; of sequences SEQ ID NO: 168-169, CTGCAG, CCNGG, GACGTC, GAATTC and GTCGAC when the group of bacteria of interest is *Shigella sonnei*; of sequences SEQ ID NO: 170-172 and GATATC when the group of bacteria of interest is *Zymomonas mobilis*; of sequence SEQ ID NO: 173 when the group of bacteria of interest is *Treponema denticola*; of sequences SEQ ID NO: 174-75, GGNCC, CTCTTC, GCATC, GCSGC and CGRYCG when the group of bacteria of interest is *Lactobacillus plantarum*; of sequences SEQ ID NO: 176-177, CCGG, CCWWGG and GCWGC when the group of bacteria of interest is *Enterococcus faecium*; of sequences SEQ ID NO: 178-179, ATCGAT, GCWGC, GCNGC, GCGCGC, GGATC and GGGAC when the group of bacteria of interest is *Bacillus liquefaciens*; of sequences SEQ ID NO: 180-182, GGTGA and CCTC when the group of bacteria of interest is *Staphylococcus epidermidis*; of sequences SEQ ID NO: 183-186, GCNGC, CTGCAG, CCCGGG, GCCGGC, CCGCGG and CAGAG when the group of bacteria of interest is *Serratia marcescens*; of sequences SEQ ID NO: 187-190 and CGATCG when the group of bacteria of interest is *Citrobacter freundii*; of sequences SEQ ID NO: 191, GGCC, GCGATG, GTCGAC, CCGG and GCNGC when the group of bacteria of interest is *Parvimonas micra*; of sequences SEQ ID NO: 192-200, GGATG and GCCGGC when the group of bacteria of interest is *Prevotella intermedia*; of sequences SEQ ID NO: 201-202, GCWGC, TGATCA and CACAG when the group of bacteria of interest is *Brucella melitensis*; of sequences SEQ ID NO: 203, CTGCAG, CRRTAAG, CCGG, GTCGAC and GCYYGAC when the group of bacteria of interest is *Aeromonas caviae*; of sequences SEQ ID NO: 204-209, GRCGYC, GCWGC, GCSGC, CCGG and GCNGC when the group of bacteria of interest is *Clostridium botulinum*; of sequences SEQ ID NO: 210-211, GCNGC, GGWCC, GTCTC, GGCC, ACGGC and VGACAT when the group of bacteria of interest is *Clostridium perfringens*; of sequences SEQ ID NO: 212-213, CCGG, CCWWGG and GCWGC when the group of bacteria of interest is *Enterococcus faecium*; of sequence SEQ ID NO: 214 when the group of bacteria of interest is *Mycoplasma pneumonia*; of sequences SEQ ID NO: 215-217, GATCAG, CCNGG, CCWWGG and CAGAG when the group of bacteria of interest is *Salmonella typhimurium*; of sequences SEQ ID NO: 218-219, GGNCC, GGATG, CWTCCAG, GCSGC, GTCGAC, GTCGAC and GCATC when the group of bacteria of interest is *Salmonella paratyphi*; of sequences SEQ ID NO: 220, CTGCAG and GCCGGC when the group of bacteria of interest is *Shigella flexnerii*; of sequences SEQ ID NO: 221, CCNGG, CTCTTC and GNAATC when the group of bacteria of interest is *Vibrio parahaemolyticus*; of sequences SEQ ID NO: 222, CTGCAG and CGGAAG when the group of bacteria of interest is *Yersinia pseudotuberculosis*; of sequences SEQ ID NO: 223-230, GAAAGC and CGAGG when the group of bacteria of interest is *Actinobacter baumanii*; of sequences GGCGCC, GCCGGC and CACAG when the group of bacteria of interest is *Bacteroides distasonis*; of sequences GGNCC and GGATG when the group of bacteria of interest is *Clostridium leptum*; of sequences GCWGC, GCTNAGC and CACAG when the group of bacteria of interest is *Brevibacterium lactofermentum*; of sequences CCGG, CCGCGG, GATATC, CGGCCG and CTCGAG when the group of bacteria of interest is *Actinobacillus actinobycetemcomitans*; of sequences GCCGGC, CCGCGG and GAGAG when the group of bacteria of interest is *Selnomonas ruminatium*; of sequences TCTAGA, GGNCC, CCTC, CCATC, GANTC, CCTTC, GCATC and TGAG when the group of bacteria of interest is *Mycoplasma mycoides*; of sequence GGCGCC when the group of bacteria of interest is *Staphilococcus lugdunensis*; of sequence GATATC when the group of bacteria of interest is *Lactobacillus rhamnosus*; of sequences CCGCGG, CTGCAG and GATATC when the group of bacteria of interest is *Lactobacillus casei*; of sequence GGCC when the group of bacteria of interest is *Lactobacillus acidophilus*; of sequences ATCGAT, GRCGYC, GCSGC, CTGCAG, GTCTC, GGATCC, GAGCTC, CTCGAG, CACAG, GAWTC and TAAATC when the group of bacteria of interest is *Bacillus coagulans*; of sequences GTAC and CCGGNAG when the group of bacteria of interest is *Pyrococcus abyssi*; of sequences GGCCGAG and CCGG when the group of bacteria of interest is *Selenomonas nominantium*; of sequence CTRYAG when the group of bacteria of interest is *Streptococcus ferus*; of sequences CCNGG, GCATGC, TTAA, GTAC and CTAG when the group of bacteria of interest is *Streptomyces phaechromo* genes; of sequence GCCGGC when the group of bacteria of interest is *Streptomyces ghanaenis*; of sequences YGGCCR and GGNCC when the group of bacteria of interest is *Enterobacter aerogenes*; of sequences GGNNCC, CGATCG, TGCA and GCSGC when the group of bacteria of interest is *Morganella morganii*; of sequences GGCC, AAGCTT, ATGCAT and GCGC when the group of bacteria of interest is *Fusobacterium nucleatum*; of sequences GCAGT, GAGTC and GATATC when the group of bacteria of interest is *Porphyromonas endodontalis*; of sequence GAATTC when the group of bacteria of interest is *Porphyromonas gingivalis*; of sequences ACGCGT, GAGCTC and CAGNNNCTG when the group of bacteria of interest is *Micrococcus luteus*; of sequences CTCGAG, GCYYGAC, YAAMGAG and CAGCTG when the group of bacteria of interest is *AEromonas hydrophila*; of sequences RTCAGG and GGWCC when the group of bacteria of interest is *Bacillus anthracis*; of sequence AGTACT when the group of bacteria of interest is *Bartonella henselae*; of sequences GGNCC, CTGCAG, GRCGYC and AGCCGCC when the group of bacteria of interest is *Brodetella pertussis*; of sequence CCGG when the group of bacteria of interest is *Borrelia garinii*; of sequences CCATC, GGCGCC, CTNAG, GGNCC and GCCGGC when the group of bacteria of interest is *Brucella canis*; of sequence SEQ ID NO: 37 when the group of bacteria of interest is *Campylobacter fetus*; of sequences CGATCG, CCCGGG and GCCGGC when the group of bacteria of interest is *Clostridium tetani*; of sequences GGCC and CTGCAG when the group of bacteria of interest is *Francisella tularensis*; of sequences CCDG and GGNCC when the group of bacteria of interest is *Legionella pneumophila*; of sequences GCGC and GGCC when the group of bacteria of interest is *Leptospira interrogans*; of sequences RGATCY, GCWGC, CCATC, GTATCC and CTAG when the group of bacteria of interest is *Leptospira santarosai*; of sequence GTCGAC when the group of bacteria of interest is *Leptospira weilii*; of sequences GGNCC, GCATC and GTCGAC when the group of bacteria of interest is *Mycobacterium leprae*; of sequences SEQ ID NO: 37, CCNGG, GAATTC, GGCC and GGGAC when the group of bacteria of interest is *Shigella dysenteriae*; of sequences GCNGC and ACGT when the group of bacteria of interest is *Staphylococcus saprophyticus*; of sequence GCCGGC when the group of bacteria of interest is *Streptococcus viridans*; of sequences GGWCC, TCGA and GMGAGC when the group of bacteria of interest is *Treponema pallidum*; of sequence GCNGC when the group of bacteria of interest is *Ureaplasma urealyticum*; and of sequences SEQ ID NO: 231-233, AGCAGY and ACCAGG when the group of bacteria of interest is *Propionibacterium acnes*.

11. The method according to claim 1, wherein the bacterial strains of said group of bacteria of interest are from the same bacterial species.

12. The method according to claim 1, wherein the bacteriophage is selected from the group consisting of IKe, CTX-y, Pfl, Pf2, Pf3, Myoviridae, Siphoviridae, Podoviridae, Tectiviridae, Corticoviridae, Lipothrixviridae, Plasmaviridae, Rudiviridae, Fuselloviridae, Inoviridae, Microviridae, Leviviridae, Cystoviridae, coliphages, B1, ATCC 51477-B1, B40-8, Bf-1, phiHSCO1, phiHSCO2, phiC2, phiC5, phiC6, phiC8, phiCD119, phiCD27, KPO1K2, K11, Kpn5, KP34, JDOO1, phiNM1, 80a1pha, IME-EF1, ENB6, C33, phiKMV, PAK-P1, LKD16, LKA1, delta, sigma-1, J-1, T2, T4, T5, T7, RB49, phiX174, R17, PRD1 bacteriophages, or the phagemid is packaged into the capsid of one of these bacteriophages.

13. The method according to claim 1, wherein phagemid is selected from the group consisting of lambda derived phagemids, P4 derived phagemids, M13-derived phagemids, pBC SK and KS phagemids, pADL and P derived phagemids.

14. The method according to claim 1, wherein said vector comprises a sequence of interest.

15. A method of treating a subject infected with pathogenic or virulent bacteria comprising the administration of a pharmaceutical or veterinary composition of an engineered vector for DNA delivery into a group of bacteria of interest, said engineered vector being an engineered bacteriophage, packaged phagemid, bacteriophage genome or phagemid, which has been genetically engineered to remove, in noncoding regions and optionally in coding regions, at least one restriction site of at least one restriction enzyme which is frequently encoded in said group of bacteria of interest, wherein said at least one restriction site is removed by changing the sequence so as to prevent the recognition by the corresponding restriction enzyme and wherein the efficiency of DNA delivery into the group of bacteria by the engineered vector is increased as compared to DNA delivery into the group of bacteria by the engineered vector prior to removal of the at least one restriction site.

* * * * *